(12) United States Patent
Smyth et al.

(10) Patent No.: US 12,285,590 B2
(45) Date of Patent: Apr. 29, 2025

(54) BIOACTIVE AGENT DISTRIBUTION

(71) Applicant: COCHLEAR LIMITED, Macquarie University (AU)

(72) Inventors: Daniel Smyth, Macquarie University (AU); Jonathon Kirk, Macquarie University (AU); Wolfram Frederik Dueck, Macquarie University (AU); Joris Walraevens, Macquarie University (AU)

(73) Assignee: Cochlear Limited, Macquarie University (AU)

( * ) Notice: Subject to any disclaimer, the term of this patent is extended or adjusted under 35 U.S.C. 154(b) by 1220 days.

(21) Appl. No.: 16/649,861

(22) PCT Filed: Sep. 21, 2018

(86) PCT No.: PCT/IB2018/057336
§ 371 (c)(1),
(2) Date: Mar. 23, 2020

(87) PCT Pub. No.: WO2019/058333
PCT Pub. Date: Mar. 28, 2019

(65) Prior Publication Data
US 2020/0297924 A1    Sep. 24, 2020

Related U.S. Application Data

(60) Provisional application No. 62/562,076, filed on Sep. 22, 2017.

(51) Int. Cl.
*A61M 5/142*    (2006.01)
*A61F 11/00*    (2022.01)
(Continued)

(52) U.S. Cl.
CPC ......... *A61M 5/14248* (2013.01); *A61F 11/00* (2013.01); *A61M 5/14276* (2013.01);
(Continued)

(58) Field of Classification Search
CPC .......... A61M 5/14248; A61M 5/14276; A61M 5/16813; A61M 5/16881; A61M 39/0247;
(Continued)

(56) References Cited

U.S. PATENT DOCUMENTS 4,535,785 A * 8/1985 van den Honert ....... A61B 5/12
600/559
7,815,615 B2  10/2010 Jolly et al.
(Continued)

FOREIGN PATENT DOCUMENTS

| EP | 1441679 A1 | 8/2004 |
|---|---|---|
| JP | 2005518845 A | 6/2005 |
| JP | 2011526619 A | 10/2011 |

OTHER PUBLICATIONS

Lichtenhan, J. T., et al. "Drug delivery into the cochlear apex: improved control to sequentially affect finely spaced regions along the entire length of the cochlear spiral." Journal of neuroscience methods 273 (2016): 201-209. (Year: 2016).*
(Continued)

*Primary Examiner* — Michael J Tsai
*Assistant Examiner* — Neeraja Gollamudi
(74) *Attorney, Agent, or Firm* — Pilloff Passino & Cosenza LLP; Martin J. Cosenza

(57) ABSTRACT

A drug delivery device configured to simultaneously interface with a scala tympani and a scala vestibuli of a cochlea, wherein the device can be configured to deliver drug to the cochlea at least in part via a post introduction non-diffusion based delivery, and wherein the device can be configured to induce complete circuit circulation from the scala tympani to
(Continued)

the scala vestibuli and/or vice versa, thereby distributing drug within the cochlea.

41 Claims, 48 Drawing Sheets

(51) Int. Cl.
*A61M 5/168* (2006.01)
*A61M 39/02* (2006.01)

(52) U.S. Cl.
CPC .... *A61M 5/16813* (2013.01); *A61M 5/16881* (2013.01); *A61M 39/0247* (2013.01); *A61M 2039/0276* (2013.01); *A61M 2039/0282* (2013.01); *A61M 2202/0405* (2013.01); *A61M 2210/0662* (2013.01)

(58) Field of Classification Search
CPC .. A61M 2039/0276; A61M 2039/0282; A61M 2202/0405; A61M 2210/0662; A61F 11/00; A61F 2/18; A61F 11/022
See application file for complete search history.

(56) References Cited

U.S. PATENT DOCUMENTS

| | | | |
|---|---|---|---|
| 7,867,193 B2 * | 1/2011 | McKenna | A61M 31/002 604/93.01 |
| 8,401,674 B2 | 3/2013 | Gibson | |
| 9,327,071 B2 | 5/2016 | Hessler | |
| 2003/0229336 A1 * | 12/2003 | Jacobsen | A61M 5/142 604/890.1 |
| 2005/0256560 A1 | 11/2005 | Lenarz et al. | |
| 2007/0005117 A1 * | 1/2007 | Fritsch | A61N 1/36038 607/56 |
| 2010/0030130 A1 * | 2/2010 | Parker | A61N 1/36038 604/20 |
| 2010/0094380 A1 * | 4/2010 | Dadd | A61N 1/36038 604/20 |
| 2011/0195123 A1 | 8/2011 | Shemi | |
| 2011/0208161 A1 | 8/2011 | Ivri | |
| 2012/0191032 A1 * | 7/2012 | Housley | A61F 11/00 607/57 |
| 2014/0018736 A1 | 1/2014 | Hessler | |
| 2015/0025509 A1 * | 1/2015 | Jolly | A61M 5/14276 604/891.1 |
| 2015/0374964 A1 | 12/2015 | Verhoeven et al. | |

OTHER PUBLICATIONS

International Search Report & Written Opinion for PCT/IB2018/057336, mailed May 14, 2019.
Extended European Search Report for European Patent Application No. 18 858 609.3, mailed May 18, 2021.

* cited by examiner

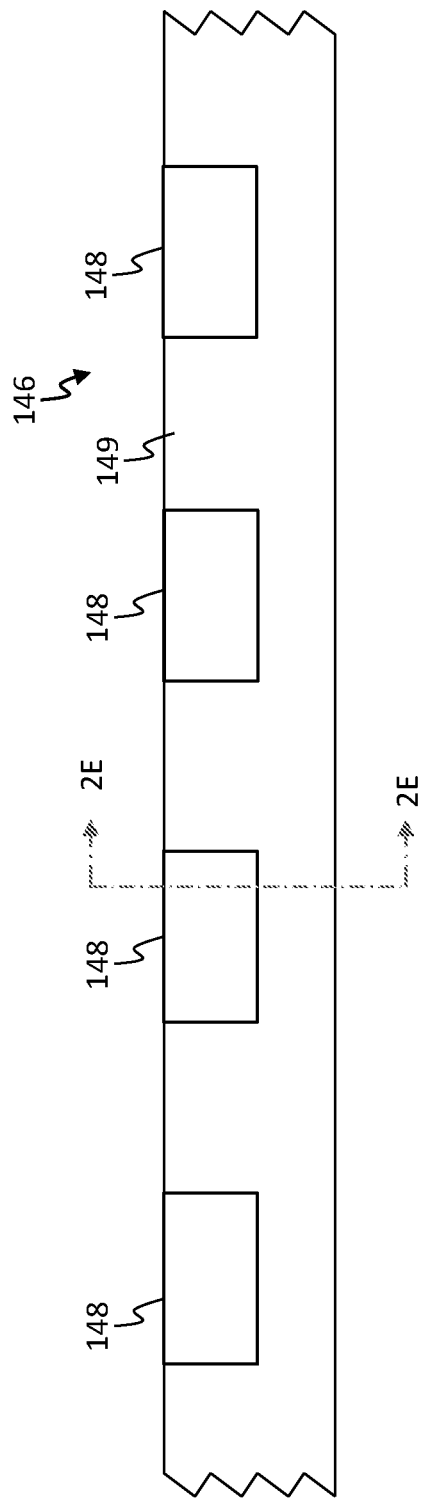
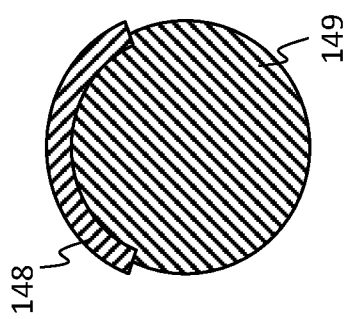
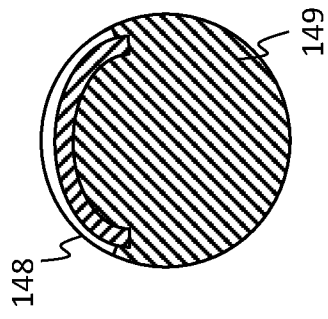
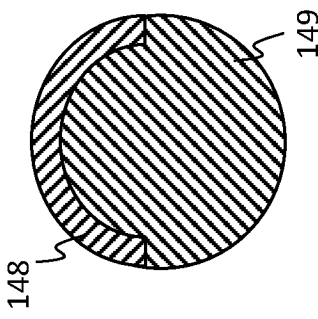
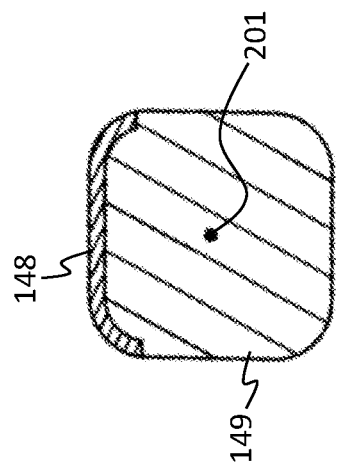

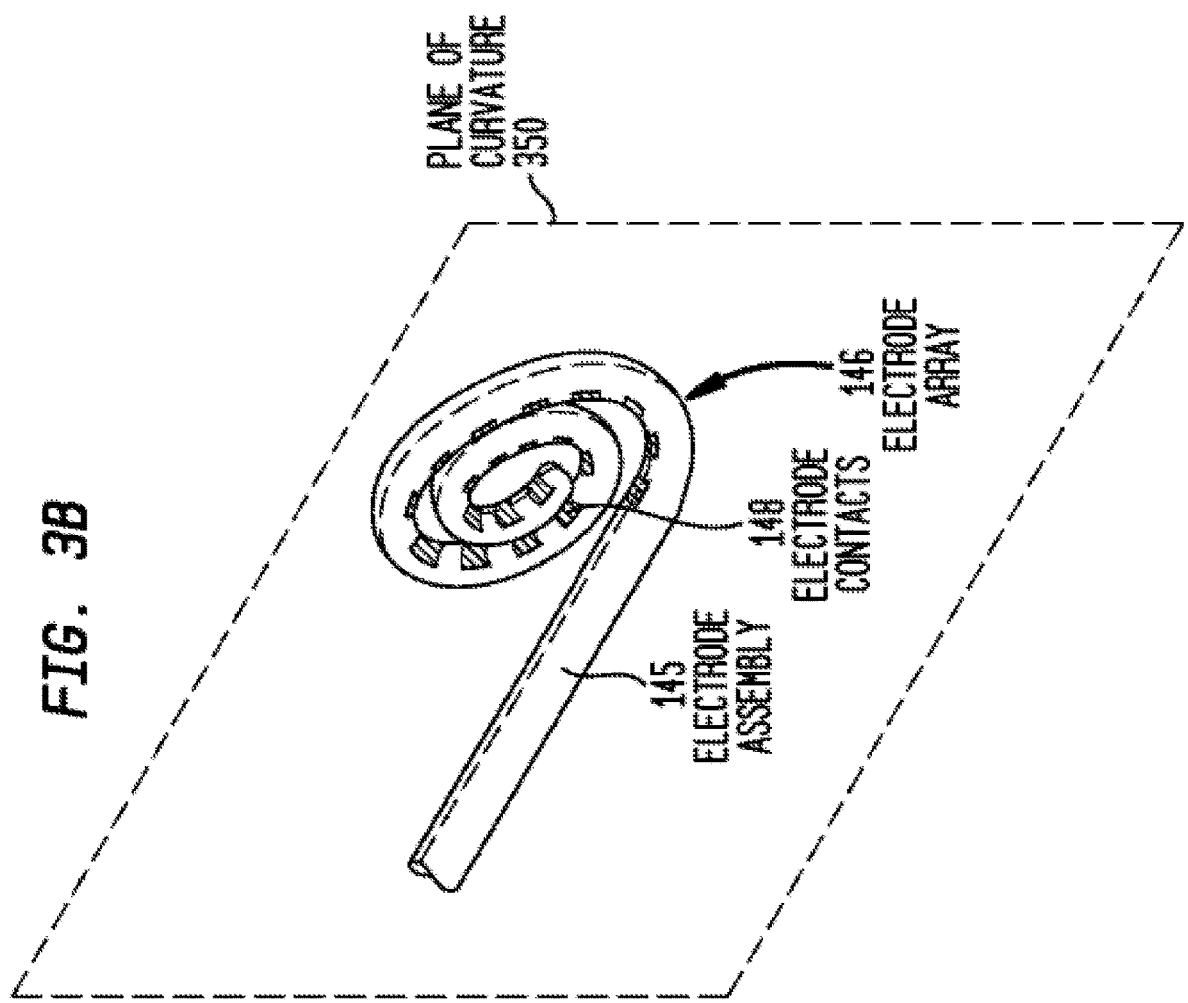

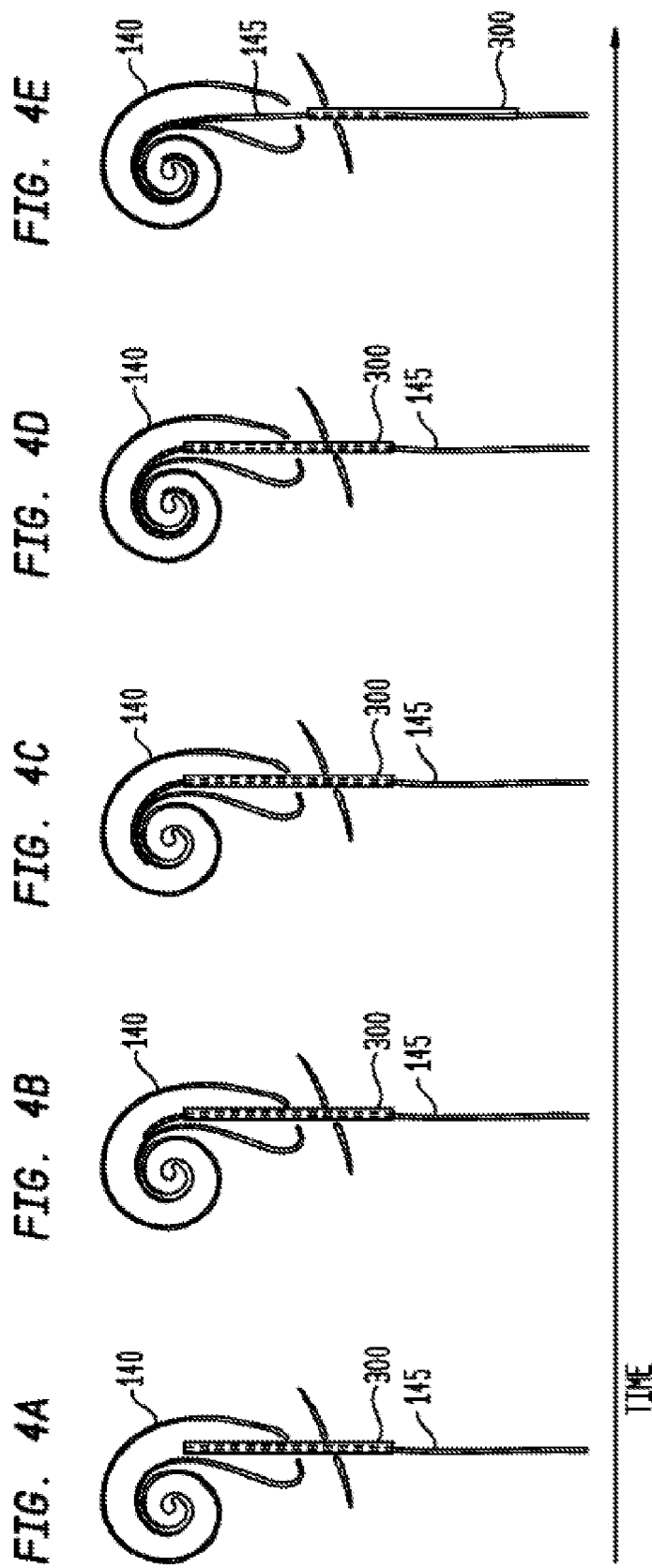

BIOACTIVE AGENT DISTRIBUTION

CROSS-REFERENCE TO RELATED APPLICATIONS

This application claims priority to U.S. Provisional Application No. 62/562,076, entitled T BIOACTIVE AGENT DISTRIBUTION, filed on Sep. 22, 2017, naming Daniel SMYTH of Mechelen, Belgium as an inventor, the entire contents of that application being incorporated herein by reference in its entirety.

BACKGROUND

Hearing loss, which may be due to many different causes, is generally of two types: conductive and sensorineural. Sensorineural hearing loss is due to the absence or destruction of the hair cells in the cochlea that transduce sound signals into nerve impulses. Various hearing prostheses are commercially available to provide individuals suffering from sensorineural hearing loss with the ability to perceive sound. One example of a hearing prosthesis is a cochlear implant.

Conductive hearing loss occurs when the normal mechanical pathways that provide sound to hair cells in the cochlea are impeded, for example, by damage to the ossicular chain or the ear canal. Individuals suffering from conductive hearing loss may retain some form of residual hearing because the hair cells in the cochlea may remain undamaged.

Individuals suffering from hearing loss typically receive an acoustic hearing aid. Conventional hearing aids rely on principles of air conduction to transmit acoustic signals to the cochlea. In particular, a hearing aid typically uses an arrangement positioned in the recipient's ear canal or on the outer ear to amplify a sound received by the outer ear of the recipient. This amplified sound reaches the cochlea causing motion of the perilymph and stimulation of the auditory nerve. Cases of conductive hearing loss typically are treated by means of bone conduction hearing aids. In contrast to conventional hearing aids, these devices use a mechanical actuator that is coupled to the skull bone to apply the amplified sound.

In contrast to hearing aids, which rely primarily on the principles of air conduction, certain types of hearing prostheses commonly referred to as cochlear implants convert a received sound into electrical stimulation. The electrical stimulation is applied to the cochlea, which results in the perception of the received sound.

It is also noted that the electrode array of the cochlear implant generally shows utilitarian results if it is inserted in a cochlea.

SUMMARY

In accordance with an exemplary embodiment, there is a device comprising a drug delivery device configured to simultaneously interface with a scala tympani and a scala vestibuli of a cochlea.

In accordance with another exemplary embodiment, there is a device, comprising a prosthesis configured to circulate perilymph within a cochlea.

In accordance with another exemplary embodiment, there is a device, comprising a means for interfacing with a cochlea and a means for distributing a therapeutic substance within a cochlea.

In accordance with another exemplary embodiment, there is a method, comprising driving an effective amount of a therapeutic substance to an apical region of the cochlea.

BRIEF DESCRIPTION OF THE DRAWINGS

Embodiments are described below with reference to the attached drawings, in which:

FIGS. 2A-2H are views of exemplary electrode arrays to which the teachings detailed herein can be applicable;

FIGS. 3A and 3B are side and perspective views of an electrode assembly extended out of an embodiment of an insertion sheath of the insertion tool illustrated in FIG. 2;

FIGS. 4A-4E are simplified side views depicting an exemplary insertion process of the electrode assembly into the cochlea;

DETAILED DESCRIPTION

Figure 1:
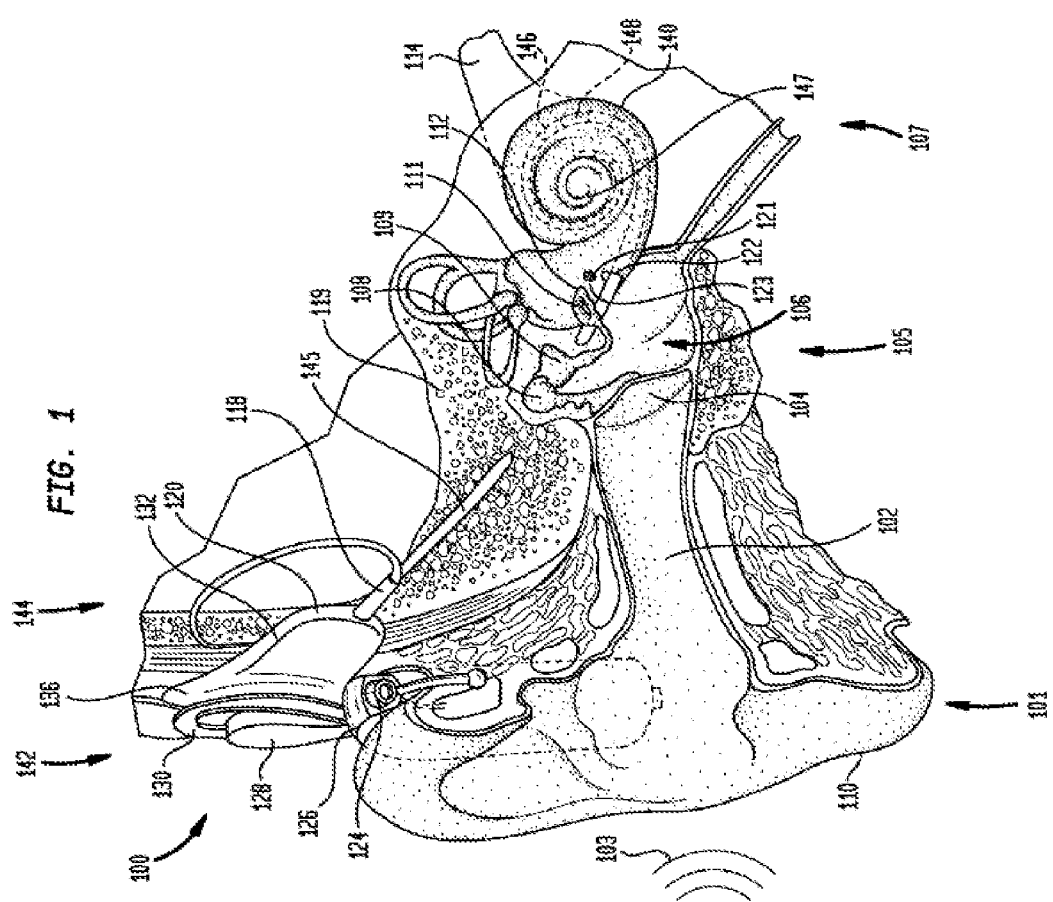
FIG. 1 is a perspective view of an exemplary hearing prosthesis.

FIG. 1 is a perspective view of an exemplary cochlear implant 100 implanted in a recipient having an outer ear 101, a middle ear 105, and an inner ear 107. In a fully functional ear, outer ear 101 comprises an auricle 110 and an ear canal 102. Acoustic pressure or sound waves 103 are collected by auricle 110 and channeled into and through ear canal 102. Disposed across the distal end of ear canal 102 is a tympanic membrane 104 that vibrates in response to sound waves 103. This vibration is coupled to oval window or fenestra ovalis 112 through the three bones of the middle ear 105, collectively referred to as the ossicles 106, and comprising the malleus 108, the incus 109, and the stapes 111. Ossicles 106 filter and amplify the vibrations delivered by tympanic membrane 104, causing oval window 112 to articulate, or vibrate. This vibration sets up waves of fluid motion of the perilymph within cochlea 140. Such fluid motion, in turn, activates hair cells (not shown) inside the cochlea which in turn causes nerve impulses to be generated which are transferred through spiral ganglion cells (not shown) and auditory nerve 114 to the brain (also not shown) where they are perceived as sound.

The exemplary cochlear implant illustrated in FIG. 1 is a partially-implanted stimulating medical device. Specifically, cochlear implant 100 comprises external components 142 attached to the body of the recipient, and internal or implantable components 144 implanted in the recipient. External components 142 typically comprise one or more sound input elements for detecting sound, such as microphone 124, a sound processor (not shown), and a power source (not shown). Collectively, these components are housed in a behind-the-ear (BTE) device 126 in the example depicted in FIG. 1. External components 142 also include a transmitter unit 128 comprising an external coil 130 of a transcutaneous energy transfer (TET) system. Sound processor 126 processes the output of microphone 124 and generates encoded stimulation data signals which are provided to external coil 130.

Internal components 144 comprise an internal receiver unit 132 including a coil 136 of the TET system, a stimulator unit 120, and an elongate stimulating lead assembly 118. Internal receiver unit 132 and stimulator unit 120 are hermetically sealed within a biocompatible housing commonly referred to as a stimulator/receiver unit. Internal coil 136 of receiver unit 132 receives power and stimulation data from external coil 130. Stimulating lead assembly 118 has a proximal end connected to stimulator unit 120, and extends through mastoid bone 119. Lead assembly 118 has a distal region, referred to as electrode assembly 145, a portion of which is implanted in cochlea 140.

Electrode assembly 145 can be inserted into cochlea 140 via a cochleostomy 122, or through round window 121, oval window 112, promontory 123, or an opening in an apical turn 147 of cochlea 140. Integrated in electrode assembly 145 is an array 146 of longitudinally-aligned and distally extending electrode contacts 148 for stimulating the cochlea by delivering electrical, optical, or some other form of energy. Stimulator unit 120 generates stimulation signals each of which is delivered by a specific electrode contact 148 to cochlea 140, thereby stimulating auditory nerve 114.

Figure 2A:
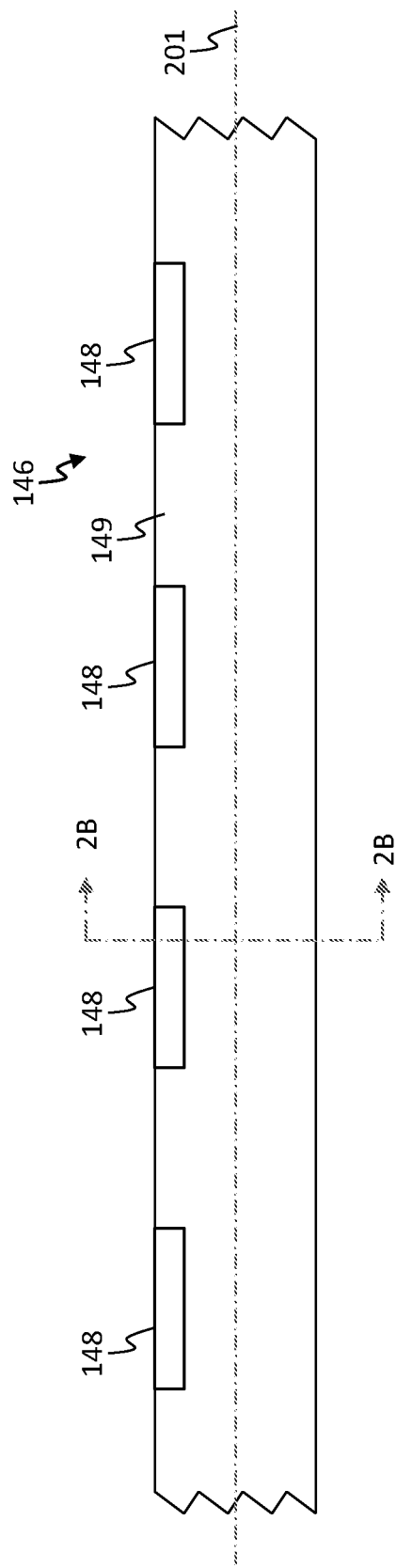
Figure 2C:
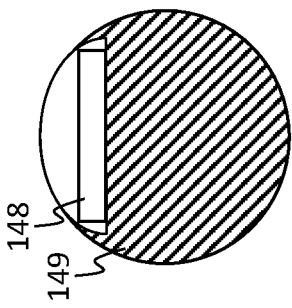
Figure 2B:
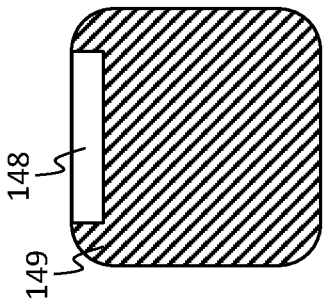

FIG. 2A depicts a conceptual side view of a portion of electrode array 146, depicting four electrode contacts 148 evenly spaced along a longitudinal axis of the electrode array 146. It is noted that in some alternate embodiments, the electrode is not evenly spaced. FIG. 2B depicts a conceptual cross-sectional view through one of the electrode contacts 148, which also depicts the carrier 149 of the electrode contact 148. In an exemplary embodiment, the carrier 149 is made of silicone. Not depicted in the figures are electrical leads and stiffener components that are sometimes embedded in the carrier 149. The embodiment of FIG. 2B represents an electrode array 146 that has a generally rectangular cross-section. FIG. 2C depicts an alternate embodiment where the electrode array 146 has a generally circular cross-section. It is also noted that in some exemplary embodiments, the cross-section is oval shaped. Thus, the embodiment of FIGS. 2A-2C is a species of the genus of an electrode array having a generally continuously curving cross-section. Any electrode array of any cross-section or any configuration can be utilized with the teachings detailed herein.

The electrode contacts 148 depicted in FIGS. 2A-2C are so-called flat contacts. In this regard, the surface of the electrode contact that faces the wall of the cochlea/the faces away from the longitudinal axis of the electrode array 146 is flat. Conversely, as seen in FIGS. 2D-2H, in some alternate embodiments, the electrode contacts 148 are so-called half band electrodes. In some exemplary embodiments, a band of contact material is "smashed" or otherwise compressed into a "half band," as seen in the figures. It is noted that by "half band," this does not mean that the electrode contact must necessarily span half of the outside diameter of the electrode array, as is the case in FIGS. 2G and 2H. The term is directed towards the configuration of the electrode itself as that term has meaning in the art. Any electrode contact that can have utilitarian value according to the teachings detailed herein can be utilized in at least some exemplary embodiments.

As can be seen from FIGS. 2A-2H, the positioning of the electrode contacts relative to the carrier 149 can vary with respect to alignment of the outer surface of the carrier with the outer surface of the contact. For example, FIGS. 2A, 2E, and 2F depict the outer surface of the contacts 148 as being flush with the outer surface of the carrier 149. Conversely, FIGS. 2C and 2G depict the contact 148 as being recessed with respect to the outer surface of the carrier 149, while FIG. 2H depicts the contact 148 as being proud relative to the outer surface of the contact 149. It is noted that these various features are not limited to the specific contact geometry and/or the specific carrier geometry depicted in the figures, and that one or more features of one exemplary embodiment can be combined with one or more features of another exemplary embodiment. For example, while FIG. 2H depicts a half band contact as being proud of the carrier 149 having a generally circular cross-section, a flat electrode such as that depicted in FIG. 2A can be proud of the carrier as well.

Figure 3A:
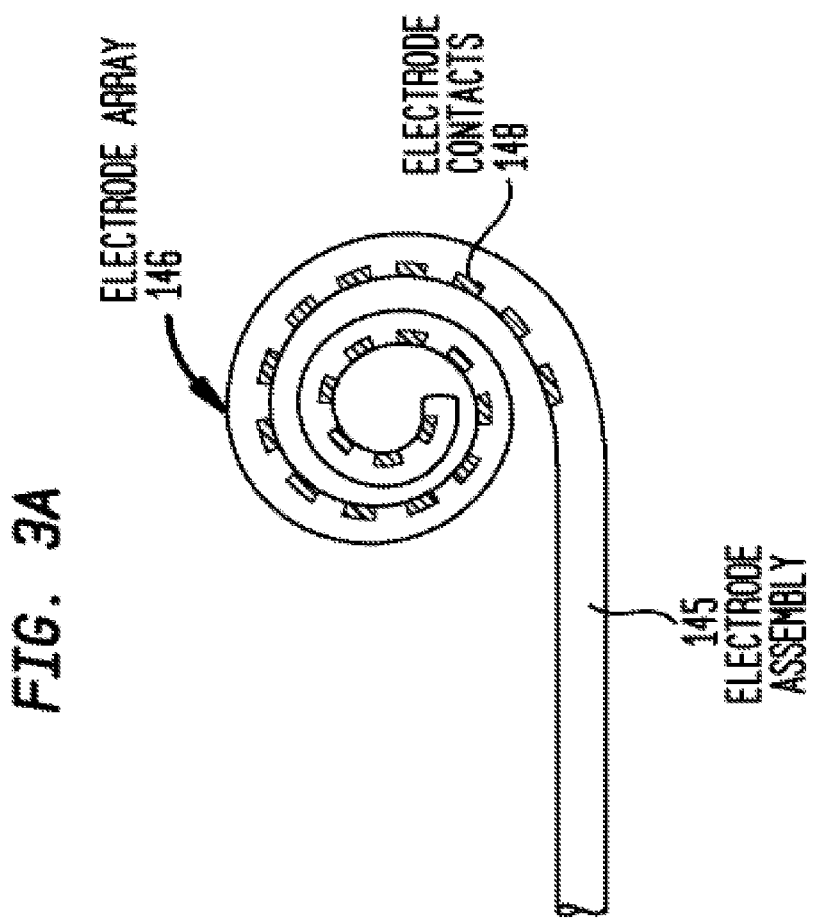

FIGS. 3A and 3B are side and perspective views, respectively, of representative electrode assembly 145. As noted, electrode assembly 145 comprises an electrode array 146 of electrode contacts 148. Electrode assembly 145 is configured to place electrode contacts 148 in close proximity to the ganglion cells in the modiolus. Such an electrode assembly, commonly referred to as a perimodiolar electrode assembly, is manufactured in a curved configuration as depicted in FIGS. 3A and 3B. When free of the restraint of a stylet or insertion guide tube, electrode assembly 145 takes on a curved configuration due to it being manufactured with a bias to curve, so that it is able to conform to the curved interior of cochlea 140. As shown in FIG. 3B, when not in cochlea 140, electrode assembly 145 generally resides in a plane 350 as it returns to its curved configuration. That said, it is noted that the teachings detailed herein and/or variations thereof can be applicable to a so-called straight electrode array, which electrode array does not curl after being free of a stylet or insertion guide tube etc., but instead remains straight. It is noted that when in the cochlea, the electrode assembly 145 takes on a conical shape with respect to plane 350 in that it can be described as winding upward away from the plane 350 about an axis normal thereto, owing to the shape of the cochlea (more on this below).

The perimodiolar electrode assembly 145 of FIGS. 3A and 3B is pre-curved in a direction that results in electrode contacts 148 being located on the interior of the curved assembly, as this causes the electrode contacts to face the modiolus when the electrode assembly is implanted in or adjacent to cochlea 140.

It is also noted that while the embodiments of FIGS. 2A-3B have been presented in terms of a so-called non-tapered electrode array (where the cross-sections of the array on a plane normal to the longitudinal axis at various locations along the longitudinal axis (e.g., in between each electrode (or a majority of the electrodes), in the middle of each electrode (or a majority of the electrodes) etc.) have generally the same cross-sectional area and shape), in an alternate embodiment, the teachings detailed herein can be applicable to a so-called tapered electrode, where the cross-sectional areas on planes taken normal to the longitudinal axis decrease with location towards the distal end of the electrode array.

FIGS. 4A-4E depict an exemplary insertion regime of an electrode assembly according to an exemplary embodiment. As shown in FIG. 4A, the combined arrangement of an insertion guide tube 300 and electrode assembly 145 is substantially straight. This is due in part to the rigidity of insertion guide tube 300 relative to the bias force applied to the interior wall of the guide tube by pre-curved electrode assembly 145.

As noted, in some embodiments, the electrode assembly 145 is biased to curl and will do so in the absence of forces applied thereto to maintain the straightness. That is, electrode assembly 145 has a memory that causes it to adopt a curved configuration in the absence of external forces. As a result, when electrode assembly 145 is retained in a straight orientation in guide tube 300, the guide tube prevents the electrode assembly from returning to its pre-curved configuration. In the embodiment configured to be implanted in scala tympani of the cochlea, electrode assembly 145 is pre-curved to have a radius of curvature that approximates and/or is less than the curvature of medial side of the scala tympani of the cochlea. Such embodiments of the electrode assembly are referred to as a perimodiolar electrode assembly, and this position within cochlea 140 is commonly referred to as the perimodiolar position. In some embodiments, placing electrode contacts in the perimodiolar position provides utility with respect to the specificity of electrical stimulation, and can reduce the requisite current levels thereby reducing power consumption.

As shown in FIGS. 4B-4D, electrode assembly 145 may be continually advanced through insertion guide tube 300 while the insertion sheath is maintained in a substantially stationary position. This causes the distal end of electrode assembly 145 to extend from the distal end of insertion guide tube 300. As it does so, the illustrative embodiment of electrode assembly 145 bends or curves to attain a perimodiolar position, as shown in FIGS. 4B-4D, owing to its bias (memory) to curve. Once electrode assembly 145 is located at the desired depth in the scala tympani, insertion guide tube 300 is removed from cochlea 140 while electrode assembly 145 is maintained in a stationary position. This is illustrated in FIG. 4E.

Figure 5:
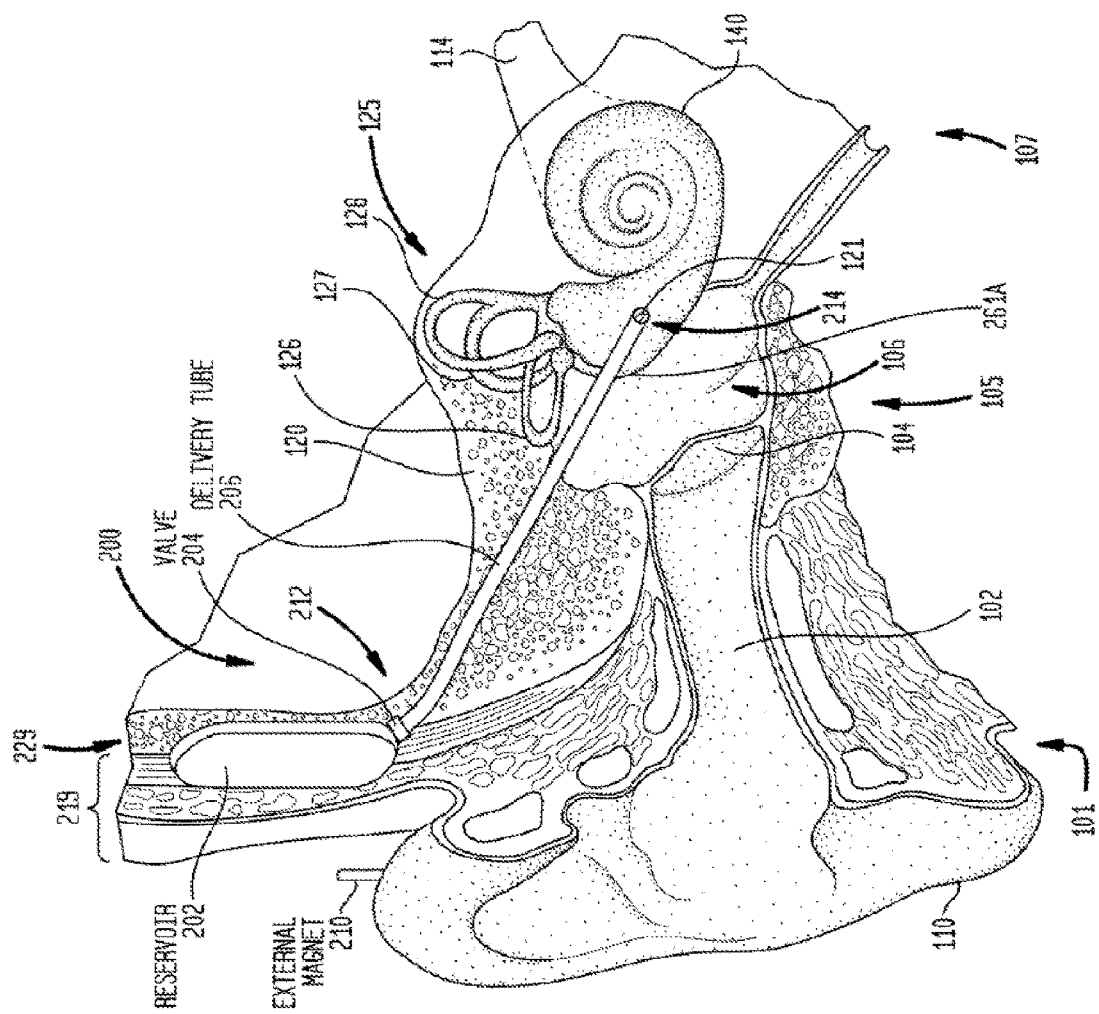
FIGS. 5-7 present an exemplary embodiment of an exemplary therapeutic substance delivery system.

FIG. 5 depicts an exemplary drug delivery device, the details of which will be provided below. It can be utilitarian to have a prompt and/or extended delivery solution for use in the delivery of treatment substances to a target location of a recipient. In general, extended treatment substance delivery refers to the delivery of treatment substances over a period of time (e.g., continuously, periodically, etc.). The extended delivery may be activated during or after surgery and can be extended as long as is needed. The period of time may not immediately follow the initial implantation of the auditory prosthesis. Embodiments of the teachings herein can facilitate extended delivery of treatment substances, as well as facilitating prompt delivery of such substances.

Figure 6:
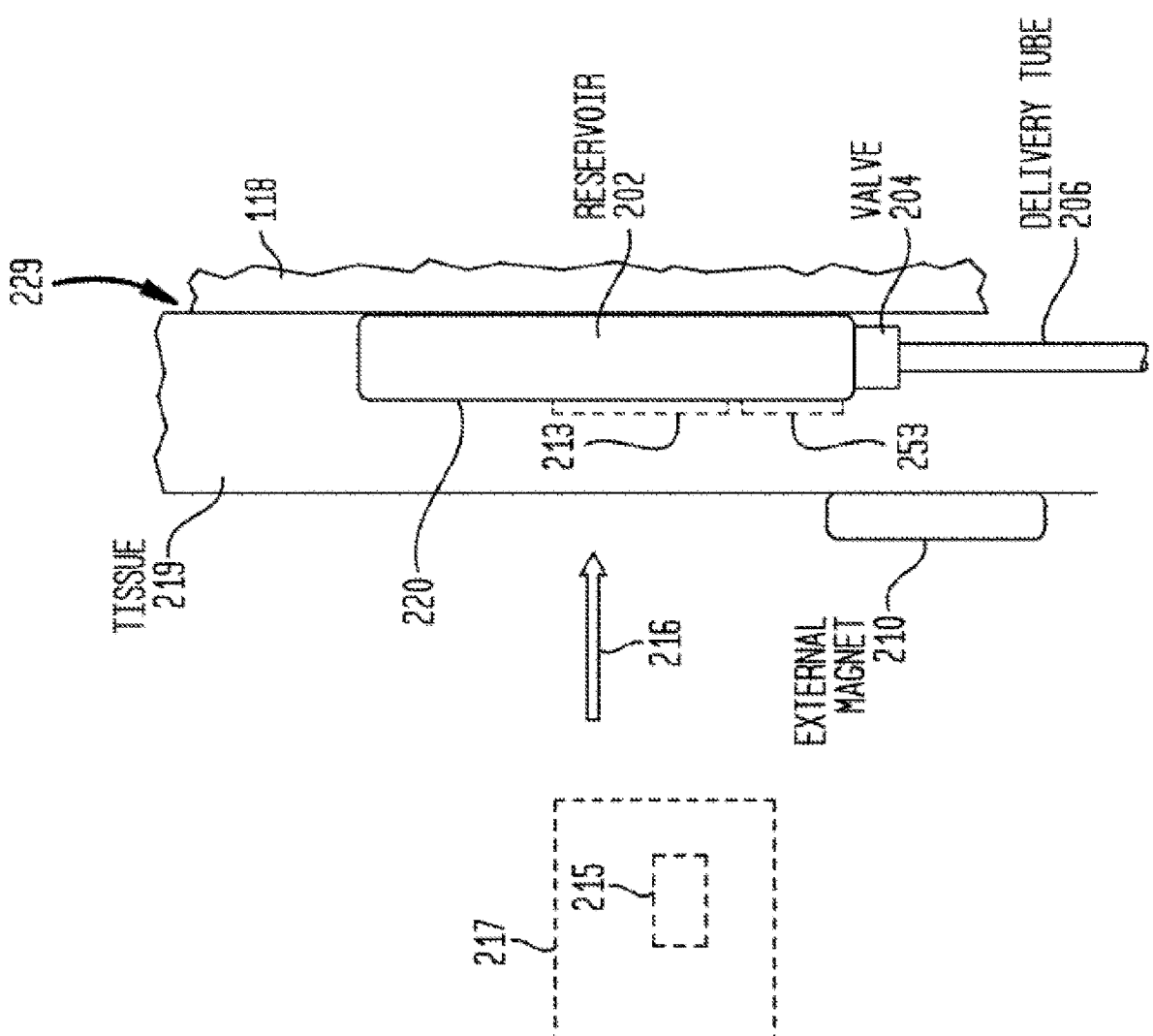

FIG. 5 illustrates an implantable delivery system 200 that can be utilized with the teachings detailed herein, and otherwise modified as detailed by way of example below. The delivery system has a passive actuation mechanism. However, it is noted that the delivery system 200 can also or instead have an active actuation system. The delivery system 200 is sometimes referred to herein as an inner ear delivery system because it is configured to deliver treatment substances to the recipient's inner ear (e.g., the target location is the interior of the recipient's cochlea 140). FIG. 6 illustrates a first portion of the delivery system 200, while FIG. 7 is a cross-sectional view of a second portion of the delivery system 200.

Figure 7:
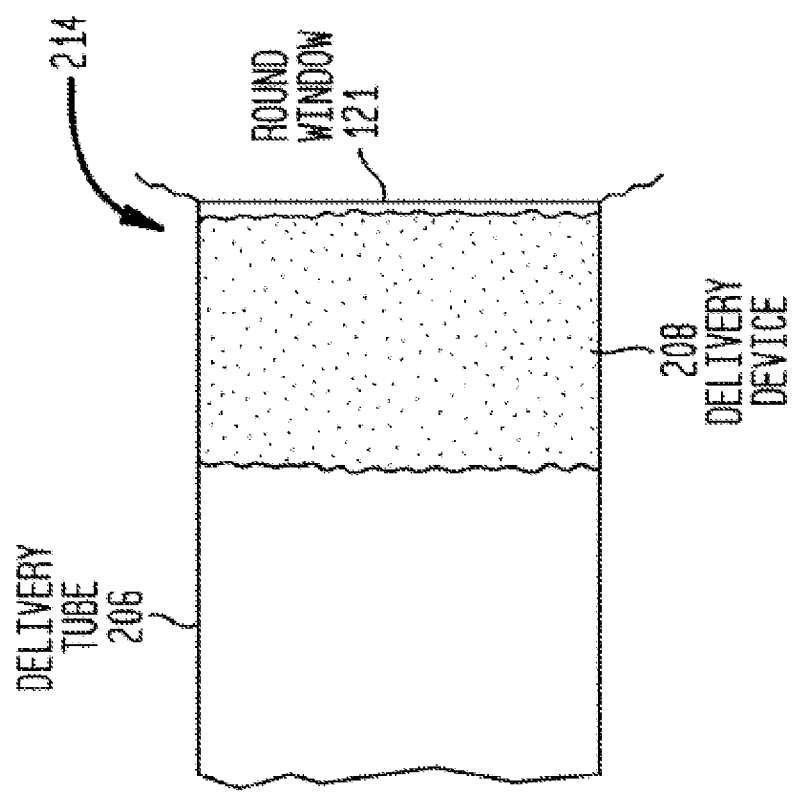

Delivery system 200 of FIGS. 5-7 comprises a reservoir 202, a valve 204, a delivery tube 206, and a delivery device 208 (FIG. 7). For ease of illustration, the delivery system 200 is shown separate from any implantable auditory prostheses. However, it is to be appreciated that the delivery system 200, and any of the other delivery systems detailed herein and/or variations thereof, could be used with, for example, cochlear implants, such as that presented in FIG. 1, direct acoustic stimulators, middle ear implants, bone conduction devices, etc. The implantable components (e.g., reservoir, valve, delivery tube, etc.) of delivery system 200 (or any other delivery system detailed herein) could be separate from or integrated with the other components of the implantable auditory prosthesis. Additionally, the delivery system 200 can include, or operate with, an external magnet 210, which is separate from or part of the implantable auditory prostheses, for purposes of, e.g., controlling operation of valve 204.

The reservoir 202 is positioned within the recipient underneath a portion of the recipient's skin/muscle/fat, collectively referred to herein as tissue 219. The reservoir 202 may be positioned between layers of the recipient's tissue 219 or may be adjacent to a subcutaneous outer surface 229 of the recipient's skull. For example, the reservoir 202 may be positioned in a surgically created pocket at the outer surface 229 (i.e., adjacent to a superior portion 118 of the temporal bone 115).

The reservoir 202 is, prior to or after implantation, at least partially filled with a treatment substance for delivery to the inner ear 107 of the recipient. The treatment substance may be, for example, in a liquid form, a gel form, and/or comprise nanoparticles or pellets. In certain arrangements, the treatment substance may initially be in a crystalline/solid form that is subsequently dissolved. For example, a reservoir could include two chambers, one that comprises a fluid (e.g., artificial perilymph or saline) and one that comprises the crystalline/solid treatment substance. The fluid may be mixed with the crystalline/solid treatment substance to form a fluid or gel treatment substance that may be subsequently delivered to the recipient.

The reservoir 202 includes a needle port (not shown) so that the reservoir 202 can be refilled via a needle injection through the skin. The reservoir 202 may be explanted and replaced with another reservoir that is, prior to or after implantation, at least partially filled with a treatment substance. The reservoir 202 may have a preformed shape and the reservoir is implanted in this shape. The reservoir 202 may have a first shape that facilitates implantation and a second shape for use in delivering treatment substances to the recipient. For example, the reservoir 202 may have a rolled or substantially flat initial shape that facilitates implantation. The reservoir 202 may then be configured to expand after implantation. Such may be used, for example, to insert the reservoir through a tympanostomy into the middle ear or ear canal, through an opening in the inner ear, or to facilitate other minimally invasive insertions. Reservoir 202 may have other shapes as needed to operate with hearing prostheses, as will be detailed below by way of example and not by way of limitation.

The delivery tube 206 includes a proximal end 212 and a distal end 214. The proximal end 212 of the delivery tube 206 is fluidically coupled to the reservoir 202 via the valve 204. As shown in FIG. 7, the distal end 214 of the delivery tube 206 is fluidically coupled to the recipient's round window 121. A delivery device 208 disposed within the distal end 214 of the delivery tube 206 is positioned abutting the round window 121. As described further below, the delivery tube 206 may be secured within the recipient so that the distal end 214 remains located adjacent to the round window 121.

FIGS. 5-7 illustrate a system that utilizes utilize a passive actuation mechanism to produce a pumping action to transfer a treatment substance from the reservoir 202 to the delivery device 208 at the distal end 214 of the delivery tube 206. More specifically, in this system, the reservoir 202 is compressible in response to an external force 216. That is, at least one part or portion of the reservoir 202, such as wall 220 or a portion thereof, is formed from a resiliently flexible material that is configured to deform in response to application of the external force 216. In some implementations of the system of FIG. 5, positioning of the reservoir 202 adjacent the superior portion of the mastoid provides a surface that is sufficiently rigid to counter the external force 216. As a result, a pressure change occurs in the reservoir 202 so as to propel (push) a portion of the treatment substance out of the reservoir through valve 204.

FIGS. 5 and 6 illustrate a specific arrangement in which the reservoir 202 includes a resiliently flexible wall 220. It is to be appreciated that the reservoir 202 can be formed from various resiliently flexible parts and rigid parts. It is also to be appreciated that the reservoir 202 may have a variety of shapes and sizes (e.g., cylindrical, square, rectangular, etc.) or other configurations. For example, the reservoir 202 could further include a spring mounted base that maintains a pressure in the reservoir 202 until the reservoir is substantially empty. Other mechanisms for maintaining a pressure in the reservoir may be used in other arrangements.

External force is applied on the tissue 219 adjacent to the reservoir 202 to create the external force. As will be described below, in some embodiments, an external vibratory device of a passive transcutaneous bone conduction device that vibrates to evoke a hearing percept is pressed onto the soft tissue 219 under which the reservoir 202 is located. The movement (e.g., oscillation/vibration) of the actuator causes deformations the reservoir 202 to create the pumping action that propels the treatment substance out of the reservoir.

Internal and/or external magnets and/or magnetic materials may be used in the arrangements of FIGS. 5 and 6 to ensure that the actuator 217 applies force at an optimal location of the reservoir 202. For example, the reservoir 202 may include a magnetic positioning member 213 located at or near an optimal location for application of an external force from the actuator 217. The actuator 217 may include a magnet 215 configured to magnetically mate with the magnetic positioning member 213. As such, when actuator 217 is properly positioned, the magnet 215 will mate with the magnetic positioning member 213 and the force from the actuator 217 will be applied at the optimal location.

A remote control, remotely placed actuator (subcutaneous or otherwise) may be alternatively used. For example, in a further arrangement, the implant includes implanted electronics 253 (shown using dotted lines in FIG. 6). These implanted electronics 253 may be configured to, for example, control the valve 204 and/or include an actuation mechanism that can force treatment substance from the reservoir 202. The implanted electronics 253 may be powered and/or controlled through a transcutaneous link (e.g., RF link). As such, the implanted electronics 253 may include or be electrically connected to an RF coil, receiver/transceiver unit, etc.

The implanted electronics 253 may include or be connected to a sensor that is used, at least in part, to assist in control of delivery of the treatment substance to the recipient. For example, a sensor (e.g., a temperature sensor, a sensor to detect infection or bacteria growth, etc.) may provide indications of when a treatment substance should be delivered and/or when delivery should be ceased for a period of time. A sensor may also be configured to determine an impact of the treatment substance on the recipient (e.g., evaluate effectiveness of the treatment substance).

As noted, the treatment substance (sometimes herein referred to as therapeutic substance) is released from the reservoir 202 through the valve 204. The valve 204 may be a check valve (one-way valve) that allows the treatment substance to pass therethrough in one direction only. This assures that released treatment substances do not back-flow into the reservoir 202. The valve 204 is a valve that is configured to open in response to the pressure change in the reservoir 202 (e.g., a ball check valve, diaphragm check valve, swing check valve or tilting disc check valve, etc.). The valve 204 may be a stop-check valve that includes an override control to stop flow regardless of flow direction or pressure. That is, in addition to closing in response to backflow or insufficient forward pressure (as in a normal check valve), a stop-check value can also be deliberately opened or shut by an external mechanism, thereby preventing any flow regardless of forward pressure. The valve 204 may be a stop-check value that is controlled by an external electric or magnetic field generated by, for example, the external magnet 210, an electromagnet, etc. In the system of FIGS. 5 and 6, the valve is responsive to a magnetic field generated by external magnet 210. As such, the valve 204 will open when the external magnet 210 is positioned in proximity to the valve 204 and will close when the external magnet 210 is removed from the proximity of the valve 204. Variable magnet strengths of external magnets may be used to control the dosage of the treatment substance. Additionally, an electromagnet may be used in place of the external magnet 210.

The use of a stop-check valve can prevent unintended dosing of the treatment substance when, for example, an accidental external force acts on the reservoir 202. The reservoir 202 is formed such that an increase in pressure of the reservoir 202 without an accompanying treatment substance release will not damage (i.e., rupture) the reservoir.

The use of a magnetically activated stop-check valve is merely exemplary and that other types of valves may be used. For example, the valve 204 may be actuated (i.e., opened) in response to an electrical signal (e.g., piezoelectric valve). The electrical signal may be received from a portion of an auditory prosthesis (not shown) that is implanted with the delivery system 200 or the electrical signal may be received from an external device (e.g., an RF actuation signal received from an external sound processor, remote control, etc.). In some instances, manually applied (e.g., finger) force be also able to open the valve 204.

Once the treatment substance is released through valve 204, the treatment substance flows through the delivery tube 206 to the delivery device 208. The delivery device 208 operates as a transfer mechanism to transfer the treatment substance from the delivery tube 206 to the round window 121. The treatment substance may then enter the cochlea 140 through the round window 121 (e.g., via osmosis). The delivery device 208 may be, for example, a wick, a sponge, permeating gel (e.g., hydrogel), etc.

The reservoir 202 may include a notification mechanism that transmits a signal or notification indicating that the reservoir 202 is substantially empty and/or needs refilled. For example, one or more electrode contacts (not shown)

may be present and become electrically connected when the reservoir is substantially empty. Electronic components associated with or connected to the reservoir 202 may accordingly transmit a signal indicating that reservoir needs filled or replaced.

FIGS. 5-7 illustrate a specific example in which the round window 121 is the target location. As noted above, the round window 121 is an exemplary target location and other target locations are possible. FIGS. 5-7 also illustrate that the reservoir 202 is positioned adjacent to the outer surface 229 of the recipient's skull so that an external force may be used to propel the treatment substance from the reservoir.

Figure 8:
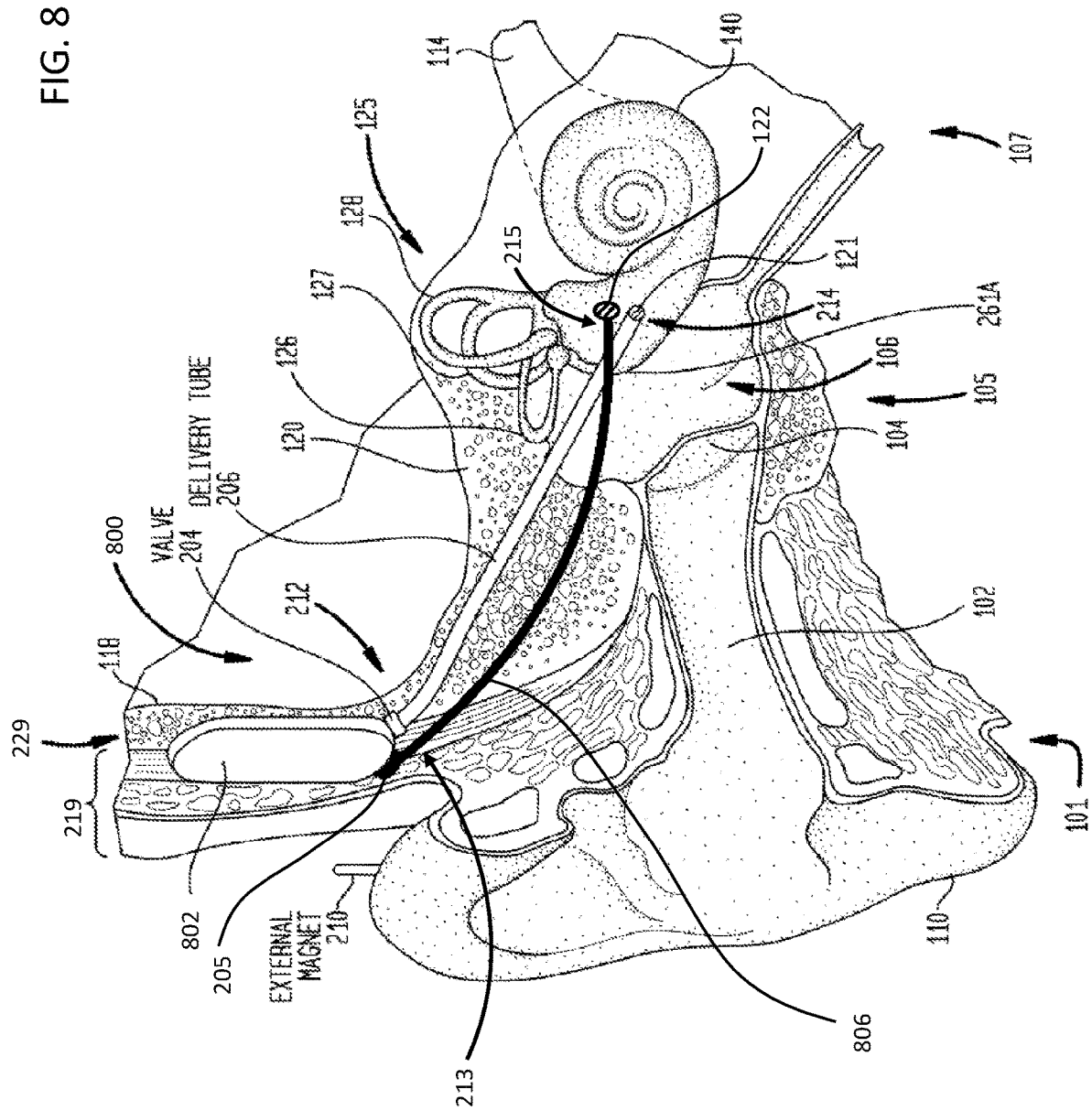
FIG. 8 presents another exemplary embodiment of an exemplary therapeutic substance delivery system.

FIG. 8 illustrates an implantable delivery system 800 that is different than system 200 in at least one way in that the delivery system 800 circulates fluid into and out of the cochlea 140 so as to disperse a therapeutic substance therein. As with system 200, system 800 can utilize a passive or an active actuation system. Any device, system, and/or method that will induce circulation of the fluid into and out of the cochlea can be utilized in at least some embodiments. Here, the system 800 includes a mixer housing 802, some more specific features of which will be described in greater detail below. As can be seen, a delivery tube 206 and a return tube 806 extend from the mixer housing 802. Like reference numbers will be utilized with respect to system 200. A valve 205 alternately opens and closes fluid communication between the proximal end 213 of return tube 806. In an exemplary embodiment, an impeller system is utilized to generate the circulatory flow. By way of example only and not by way of limitation, located in housing 802 can be an impeller driven by electric motor that drives fluid into delivery tube 206 and/or located in housing 802 can be an impeller driven by electric motor that drives fluid out of tube 806. Some additional details of these features will be described in greater detail below.

In the embodiment of FIG. 8, the housing 802 positioned within the recipient underneath a portion of the recipient's skin/muscle/fat, collectively referred to herein as tissue 219, and can be positioned as reservoir 202 is positioned above. As will be detailed below, the housing 802 can be positioned elsewhere, and, with respect to a modified embodiment of the housing 802, the housing 802 can be positioned in the middle ear.

Any treatment substance as detailed above with respect to reservoir 202 can be utilized or otherwise contained in housing 802 for mixing with the perilymph from the cochlea. Indeed, any one or more features detailed above with respect to reservoir 202 can be present with respect to housing 802 in at least some embodiments (and vice versa).

As seen, the proximal end 213 of the return tube 806 is fluidically coupled to the housing 802 via the valve 205, which can correspond to valve 204 and have the same functionality thereof or different functionality (e.g., preventing flow out of the housing 802 instead of into the housing 802). In an alternate embodiment, there is no valve 205, and the tube is directly connected to the housing and/or the valve 205 is away from the housing (there are two tube segments, with the valve in the middle). As shown in FIG. 8, the distal end 215 of the return tube 806 is fluidically coupled to the recipient's oval window 122. Unlike the embodiment of FIG. 5, there is no delivery device 208 disposed within the distal end 214 of the delivery tube 206 which is positioned abutting the oval window 122. Instead, the delivery tube 206 is in fluid communication with the interior of the cochlea. As described further below, the return tube 806 may be secured within the recipient so that the distal end 215 remains located adjacent to the oval window 122.

In some embodiments, as will be described in greater detail below, the distal ends of the tubes can be configured to penetrate through the oval and round windows into the cochlea to establish fluid communication between the respective ducts of the cochlea and the respective tubes by way of direct fluid flow (as opposed to, for example, osmosis or diffusive flow). Accordingly, in an exemplary embodiment, the delivery devices at the ends of the tubes are valves or the like and/or are flanged ports that couple to the cochlea. In some embodiments, the delivery devices extend through the round and oval windows in a manner that seals the round and oval windows between the inner circumference thereof and the delivery devices. Again, additional features of such will be described in greater detail below. That said, it is noted that while some embodiments are directed towards the utilization of intrusive mechanical coupling devices to secure the delivery system to the cochlea, in some alternate embodiments, nonintrusive coupling devices, such as clamps, glues, etc. can be utilized. It is noted that in some embodiments, the tubes are intentionally positioned to avoid contact with any structure of the cochlea or even the human at the tip of the tubes and/or along their length back to the opening into the cochlea. That is, the tube extends like a quasi-cantilever beam in the cochlea, supported by the opening into the cochlea/wall between the middle ear and the inner ear. This can have utilitarian value with respect to minimizing any deleterious effect on hearing (e.g., due to contact with the membranes and/or walls in the cochlea duct(s)—thus, in an exemplary embodiment, the method of insertion avoids the aforementioned insertion as well—that it, the tip and the length behind the tip never contacts the inside of the cochlea—in some embodiments, no part of the device in the cochlea contacts the tissue therein save for the location at the opening, for at least 1, 2, 3, 4, 5, 6, 7, 8, 9, 10, 15, 20, 25, 30, 40, 50, 60, 70, 80, 90, 100 days, weeks, months or years).

The embodiment of FIG. 8 permits the circulation of a fluid into and out of the cochlea, where, a therapeutic substance is entrained or otherwise mixed into the fluid that is circulated into and out of the cochlea. Additional details of the entrainment/mixing of the therapeutic substance are detailed below. However, for the moment, focus will be upon the circulation of fluid, where it is to be understood that in at least some exemplary embodiments, the circulation of fluid can include the therapeutic substance therein, while in other embodiments, the circulation of fluid does not include the therapeutic substance therein (i.e., it is at least substantially all perilymph) and/or the circulation of fluid may include a therapeutic substance therein, but at the particular time frame of interest, there is no therapeutic substance being added to the fluid.

It is noted that in an exemplary embodiment, the system is configured to be located in part, in the middle ear and, in part, at a retroaurical position (e.g., the reservoir can be located at that position), and/or, in part, in the cochlea.

Figure 9:
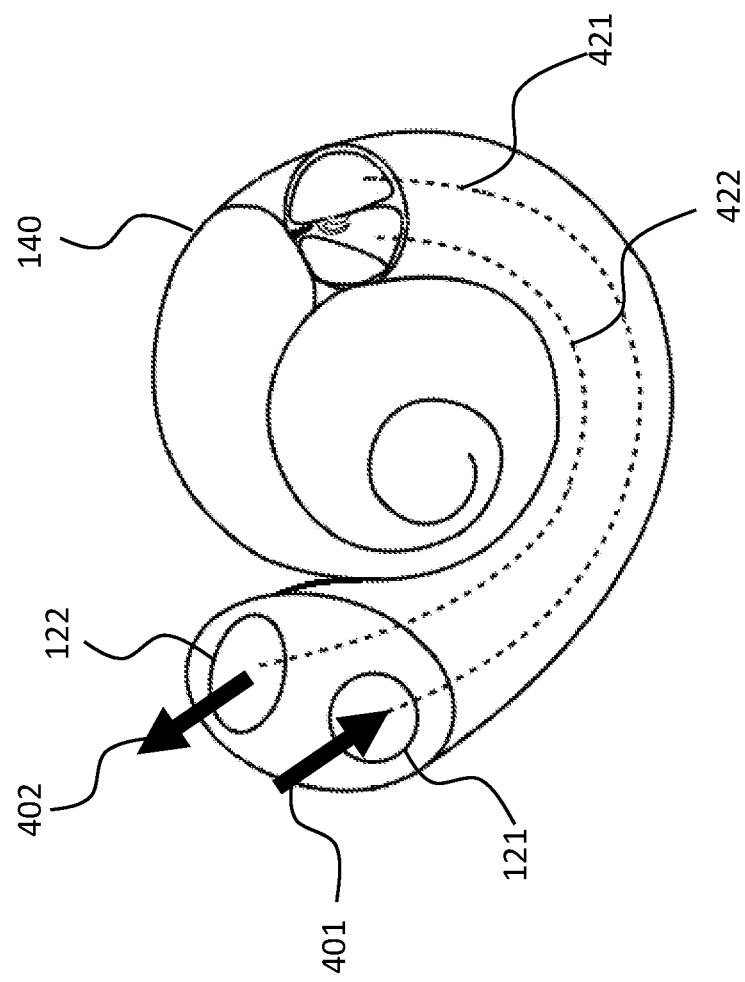
FIGS. 9-12 functionally depict a principle of operation according to an exemplary embodiment.

With respect to the circulation of fluid, FIG. 9 depicts a high-level conceptual view of this concept, where arrow 401 represents fluid flow from tube 206 through the round window 121 into the cochlea in general, and into the tympanic duct in particular. The fluid travels along fluid flow path 421 until it reaches the apical portion of the cochlea, and then transitions into the vestibular duct (e.g., for example, at the heliotrema) and then travels along fluid flow path 422 and then exits through the oval window 122, and thus into tube 806, as represented by arrow 402.

Figure 10:
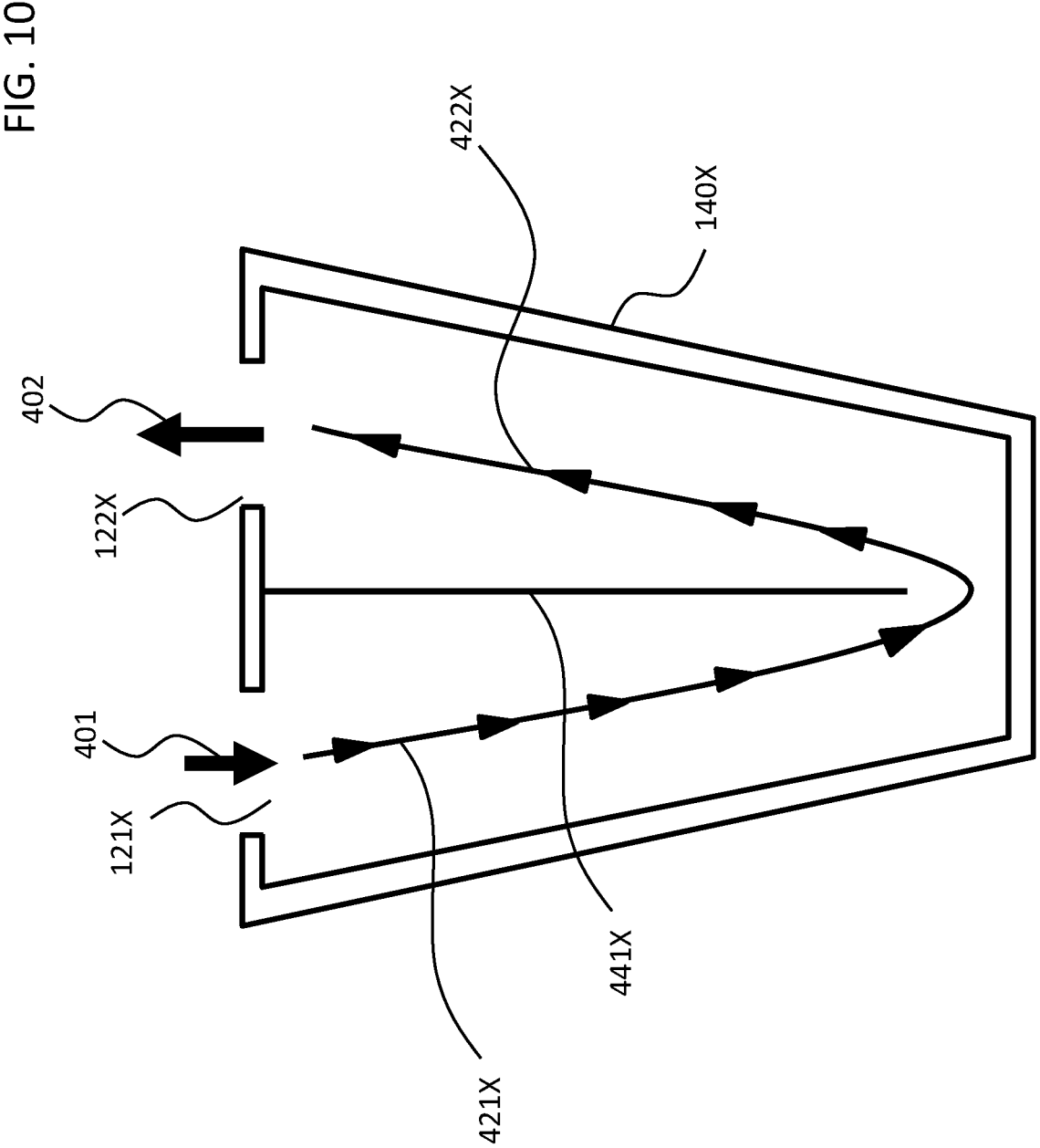

FIG. 10 presents a functional conceptual view of the principle of operation of the circulation of fluid through the cochlea, with respect to a functional view of a cochlea, 140X. In FIG. 10, the delivery tube 206 delivers fluid, which can include the active substances detailed herein or does not include such substances. The delivery of fluid into the cochlea is represented by arrow 401, which represents fluid being directed through the round window 121X. The fluid flow in the cochlea constitutes two parts. The first being the fluid flow in the tympanic duct 421X, and the second being the fluid flow in the vestibular duct 422X. These flows being bifurcated by structure of the cochlea that bifurcates these two ducts, conceptually represented by 441X. As can be seen, once the fluid flow reaches the apical portion of the cochlea, the fluid begins its return trip back to the delivery system 800. The fluid exits the cochlea 140X at the oval window 122X, as represented by arrow 402.

Figure 11:
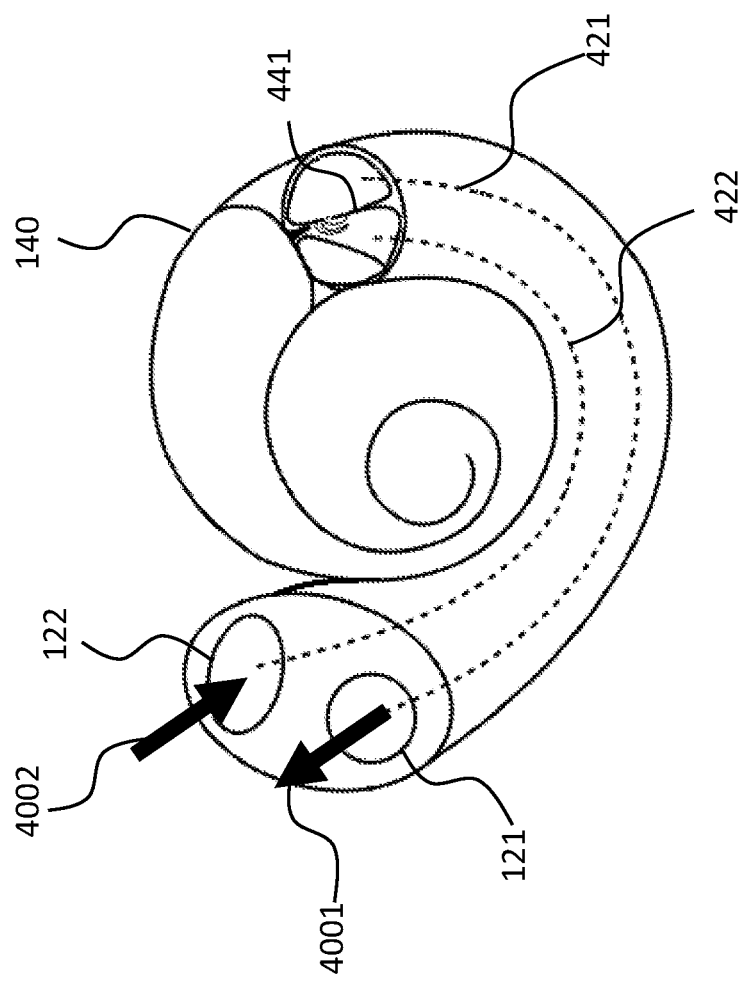
Figure 12:
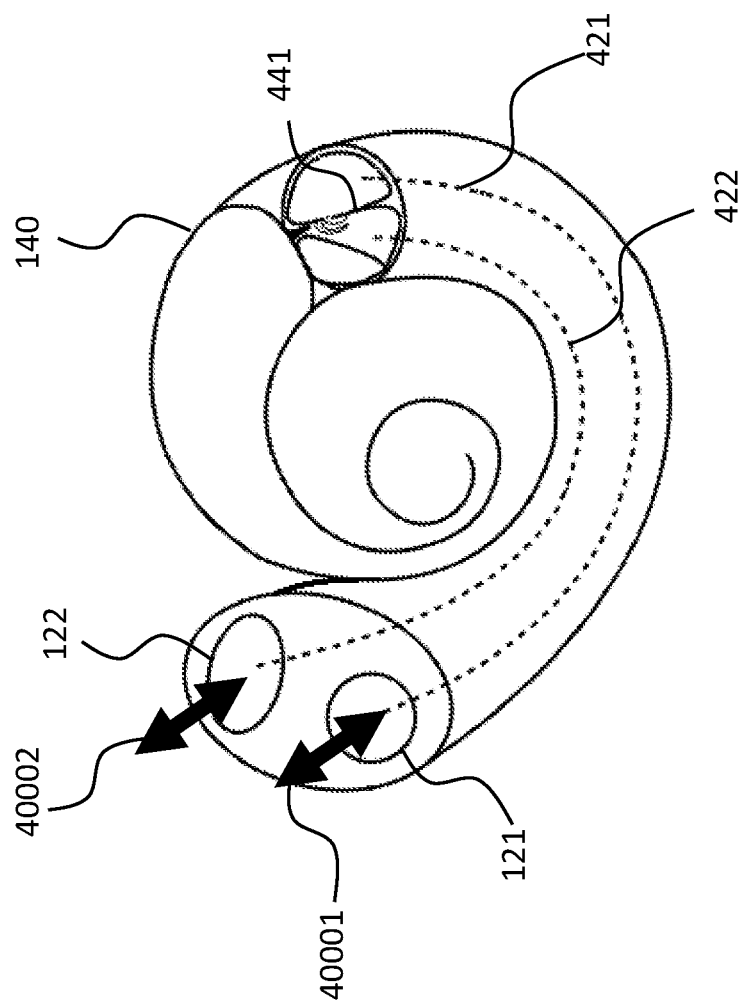

It is briefly noted that while the embodiments presented above have focused upon fluid flow where the fluid enters the cochlea at the round window and exits the cochlea at the oval window, in an alternative embodiment, this is reversed. In this regard, tube 206 can be utilized to deliver fluid through the oval window 122 and tube 806 can be utilized as the return of fluid through round window 121, as respectively represented by arrows 4002 and 4001 in FIG. 11. Note further that in some exemplary embodiments, the system 800 is configured to reverse the direction of fluid flow through the respective tubes, depending on the temporal period of use of the system. In this regard, FIG. 12 conceptually represents a scenario where the direction of fluid flow is reciprocally changed over time, as represented by arrows 40001 and 40002. In this regard, tube 206 can be a delivery tube in some instances, and a return tube in other instances, and tube 806 can be a return tube in some instances, and a delivery tube and other instances. It is noted that this reversal of fluid can occur after a period of, for example, at least after 1 minute, 1.5 minutes, 2 minutes, 2.5 minutes, 3 minutes, 3.5 minutes, 4 minutes, 5 minutes, 6 minutes, 7 minutes, 8 minutes, 9 minutes, 10 minutes, 11 minutes, 12 minutes, 13 minutes, 14 minutes, 15 minutes, 20 minutes, 25 minutes, 30 minutes, 40 minutes, 50 minutes, 60 minutes, 70 minutes, 80 minutes, 90 minutes, 100 minutes, 110 minutes, 120 minutes, 2.5 hours, 3 hours, 3.5 hours, 4 hours, 5 hours, 6 hours, 7 hours, 8 hours, 9 hours, 10 hours, 11 hours, 12 hours, 15 hours, 20 hours, 24 hours, or more, of fluid flow in one direction. In at least some exemplary embodiments, the reversal of flow occurs in a cyclic period that does not evoke a hearing percept or otherwise did not evoke a distracting hearing percept in the recipient to the extent that the recipient retains any residual hearing.

In some embodiments, fluid entering the cochlea, unless a flow is created, will be moved through cochlea by diffusion only, rather than by a traditional concept of flow. By way of example, if a molecule is placed in the base of tympani, the movement of the molecule will be random, but it may eventually find the way to the base of vestibuli. If one places a statistically significant number of molecules therein, some of them will arrive at vestibuli base at some point, but the arrival time will still be random. If there is a concentration gradient, this will eventually be removed, by the process of diffusion. Some embodiments utilize diffusion, while others use flow, while others use a combination of such.

Figure 13:
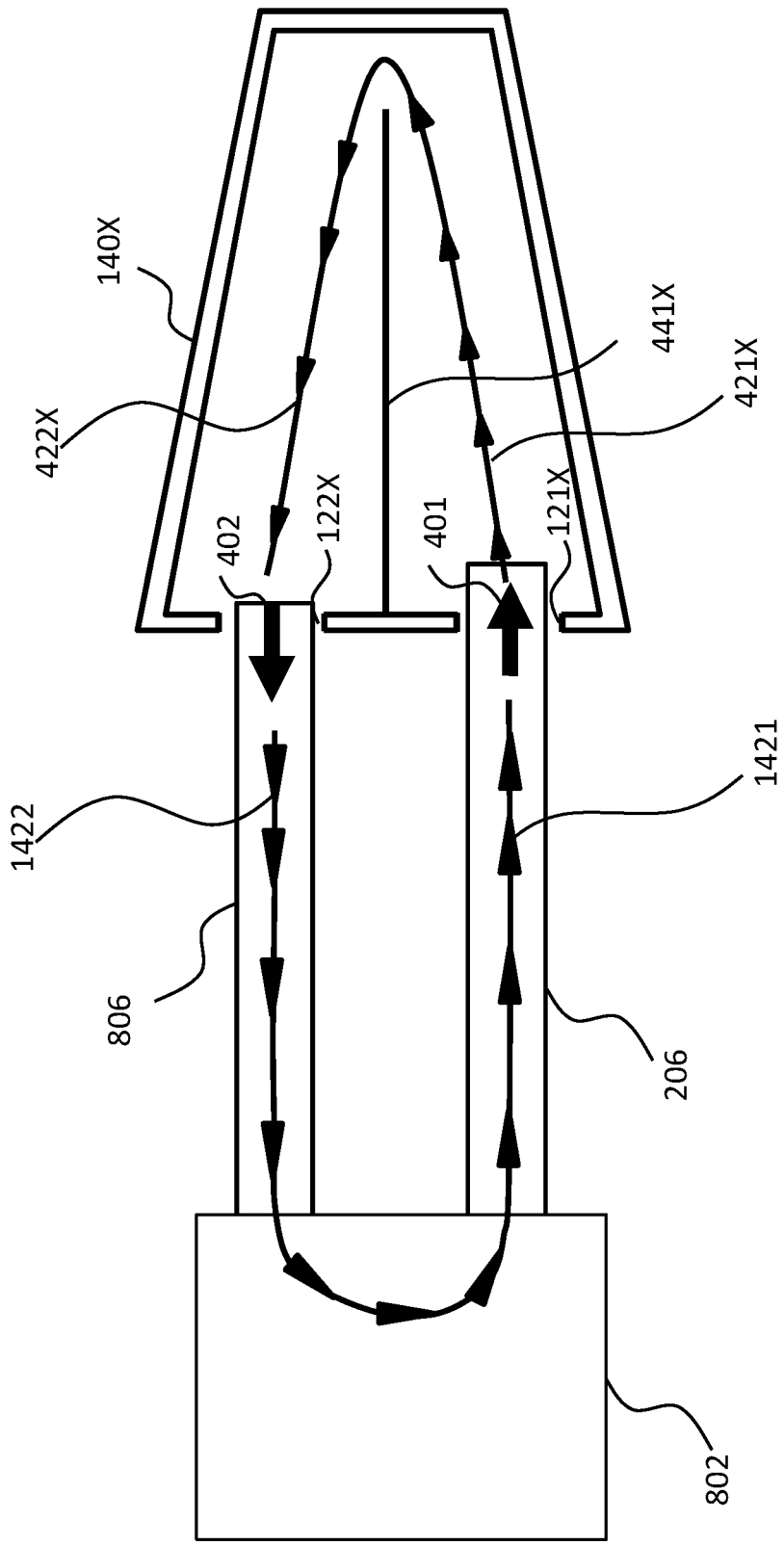
FIG. 13-19 functionally conceptually depict exemplary usage of an exemplary embodiment.

It is noted that some embodiments include a surgical technique where, in the event that cochlea fluid has escaped, CSF is replaced in the cochlea. As will be explained in greater detail below, the CSF can be removed and replaced with cochlea fluid, which might have been captured at the escape time (the escape could have been controlled, and guided into a temporary container). Also, the introduction of CSF can create a longitudinal flow between the cochlea aqueduct and the site of the perforation FIG. 13 presents an exemplary functional somatic of fluid circulation into and out of the cochlea and into and out of system 800 according to an exemplary embodiment. As can be seen, in this embodiment, tubes 206 and 806 extend into the cochlea. In this regard, in an exemplary embodiment, there is no discrete interfacing component per se. In this exemplary embodiment, the tubes 806 and 206 are sized and dimensioned so as to fill the space of the oval and round windows and/or the space of the hole therein (which may not take up the entire space of the oval and round window—it is the surgical opening that is filled) so that the fluid in the cochlea cannot escape or otherwise does not leak out in substantial amounts. That is, while the embodiment of FIG. 13 depicts an opening between the tubes 806 and 206 and the structure of the cochlea 140X, in at least some exemplary embodiments, there is no opening. However, as will be described in greater detail below, in some embodiments, separate interfacing components are located at the distal ends of the tubes that interface with the cochlea and provide a seal between the windows and the components of the delivery system. Any arrangement that can enable utilitarian fluid circulation into and out of the cochlea can be utilized in at least some exemplary embodiments.

It is also noted that while the embodiment of FIG. 13 and the embodiments depicted so far present utilization of the round and oval windows as the entry and exit ports, in some alternate embodiments, one or more cochleostomys are utilized to provide fluid communication between the delivery system 800 and the cochlea. By way of example only and not by way of limitation, in an exemplary embodiment, the round window is utilized to place the delivery system into fluid communication with the tympanic duct, and a cochleostomy to the vestibular duct is utilized so as to maintain the oval window membrane. Alternatively, by way of example only and not by way of limitation, the oval window is utilized to place the delivery system into fluid communication with the vestibular duct, and a cochleostomy to the tympanic duct is utilized so as to maintain the round window membrane. Still further, by way of example only and not by way of limitation, respective cochleostomys to the tympanic duct and the vestibular duct are utilized to respectively bypass the round and oval windows and maintain the membranes thereof in place. Any arrangement that can be utilized to access the inside of the cochlea to establish fluid flow herein can be utilized in at least some exemplary embodiments.

Still with reference to FIG. 13, it can be seen that the fluid flow out of the cochlea from the oval window becomes fluid flow 1422 and travels down the return tube 806 to the housing 802. The fluid flow then reverses direction and becomes fluid flow 1421 and travels out of the housing 802 and then travels down delivery tube 2062 to the cochlea, where the fluid flow becomes 421X upon reintroduction into the cochlea.

In an exemplary embodiment, mixing housing 802 can include a powered pump or the like that induces the circulation flow. Accordingly, in at least some exemplary embodiments, the system is an active system. Some additional details of this will be described below. That said, in an alternative embodiment, the system is a passive system, where the circulation is established via any one or more of the scenarios detailed above with respect to system 200. By way of example only and not by way of limitation, housing 802 can include a flexible portion where the recipient can repeatedly press thereupon so as to pump the fluid into and out of the cochlea. Again, some additional details will be described below. It is noted that in some embodiments, there is a flow limiting device, such as a flow limiting valve, that limits flow into the cochlea and/or out of the cochlea to a safe and/or utilitarian level. In an exemplary embodiment, the flow limiter limits flow to a rate of no more than 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.25, 2.5, 2.75, 3, 3.5, 4, 4.5, 5, 5.5, 6, 6.5, 7, 7.5, 8, 8.5, 9, 9.5, 10, 11, 12, 13, 14, 15, 16, 17, 18, 19 or 20 µl/hour, at least for embodiments where there is no replacement fluid being affirmatively introduced (e.g., something more than natural diffusion/introduction of CFS). In an exemplary embodiment, the device is configured to limit flow into and/or out of the cochlea to ensure that the difference between the normal amount and the actual amount of fluid therein, for a 25 to 75 percentile human factors engineering human of the age of which the implant is provided, which human can be a citizen of the United States, the EU, UK, the Federal Republic of Germany, the Republic of France, the Republic of Italy, and/or Japan and/or the People's Republic of China, to a flow rate that would reduce and/or increase the volume of fluid at any given time by no more than 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.25, 2.5, 2.75, 3, 3.5, 4, 4.5, 5, 5.5, 6, 6.5, 7, 7.5, 8, 8.5, 9, 9.5, 10, 11, 12, 13, 14, 15, 16, 17, 18, 19 or 20 percent of that which was present before the commencement of flow.

Figure 14:
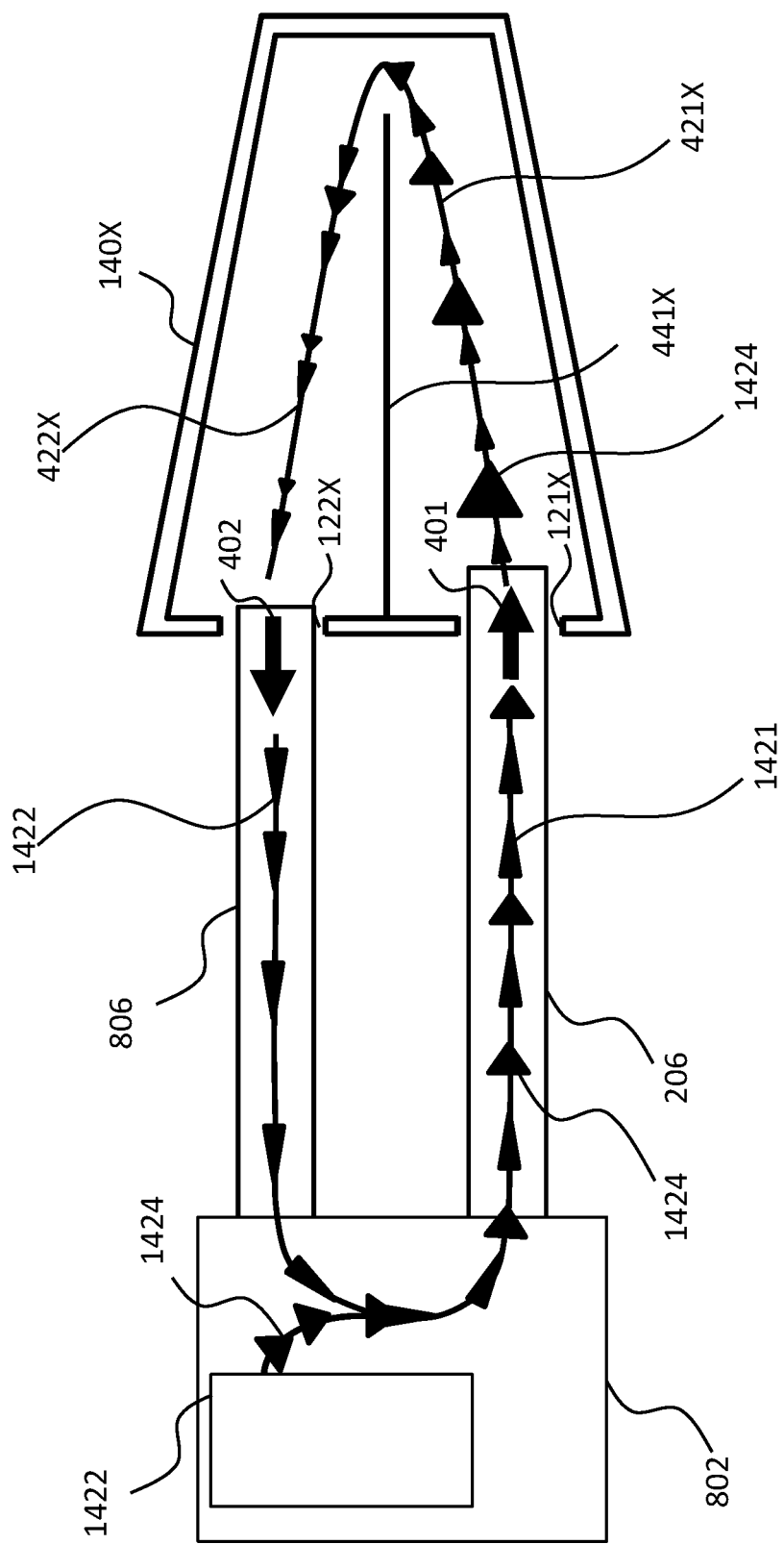

There can be utilitarian value with respect to simply circulating fluid into and out of the cochlea, irrespective of whether the fluid contains therein a therapeutic substance, such as an active drug. That said, in some embodiments, there is utilitarian value with respect to circulating a fluid through the cochlea that includes an active drug or other therapeutic substance. In this regard, FIG. 14 depicts an exemplary embodiment where an active therapeutic substance 1422 is entrained or otherwise injected into the fluid flow flowing into and out of the cochlea. More specifically, in the embodiment of FIG. 14, mixing housing 802 includes a reservoir and mixing system 1422 that releases an active substance 1424 into the fluid flow flowing into and out of the cochlea. In an exemplary embodiment, reservoir and mixing system 1422 includes a reservoir and a piston and valve arrangement that meters one or more doses of therapeutic substance out of the reservoir and mixing system 1422 into the fluid flow, and thus the mixing system 1422 can be considered an injection system. In an alternate embodiment, the reservoir and mixing system 1422 entails a porous chamber containing an active substance and the system 1422 permits the active substance to leach out of the system 1422 into the fluid flow. In alternative embodiment, the reservoir and mixing system 1422 entails a porous chamber containing an active substance, but the system 800 is configured such that the fluid flow flows into and out of the system 1422, at least a portion of the active substance dissolves into the fluid flow, which then leaves the system 1422 and exits out housing 802 into tube 206 for delivery to the cochlea. In an alternative embodiment, the reservoir and mixing system 1422 is a system that mechanically dispenses solid pellets containing an active substance out of a housing via a conveyor belt into the fluid flow stream, where the pellets dissolve while in fluid flow 1421 while in tube 206. Any arrangement of introducing an active substance into the fluid flow circulating into and out of the cochlea can be utilized in at least some exemplary embodiments. It is noted that this is but an example, and other embodiments can utilize a different delivery regime.

Still with reference to FIG. 14, it can be seen that the active substance 1424 is entrained or otherwise next with the circulating fluid flow in housing 802. The active substance 1424 travels down tube 206 with flow 1421. The former is represented by the wide triangles, and the latter is represented by the long triangles. FIG. 14 conceptually depicts how the active substance gradually is removed from the fluid flow as the fluid flow travels through the cochlea. As can be seen, the wide triangles progressively become smaller and smaller with distance from the introduction point into the cochlea. This represents the tissue of the cochlea absorbing the therapeutic substance as the fluid flow travels through the cochlea. In at least some exemplary embodiments, the ratio of therapeutic substance to the non-therapeutic or otherwise non-active substance of the fluid flow is such that by the time the fluid exits the cochlea or otherwise enters return tube 806, there is little to no therapeutic substance left in the fluid flow because it has been absorbed by the tissue. In an exemplary embodiment, the absorption is uniform such that all areas of the cochlea absorb about the same amount of therapeutic substance. That said in some alternate embodiments, the absorption is not uniform such that some areas of the cochlea absorb more of the therapeutic substance than other areas. By way of example only and not by way of limitation, in an exemplary embodiment, such as where an electrode array of a cochlear implant has been inserted into the tympanic duct, and/or where the actuator of a direct acoustic cochlear stimulator (DACS) has been inserted into the tympanic duct, more therapeutic substance can be absorbed at those locations than in the vestibular duct. That said, in some alternate embodiments of the aforementioned implant regimes, the absorption of the therapeutic substance is uniform.

Figure 15:
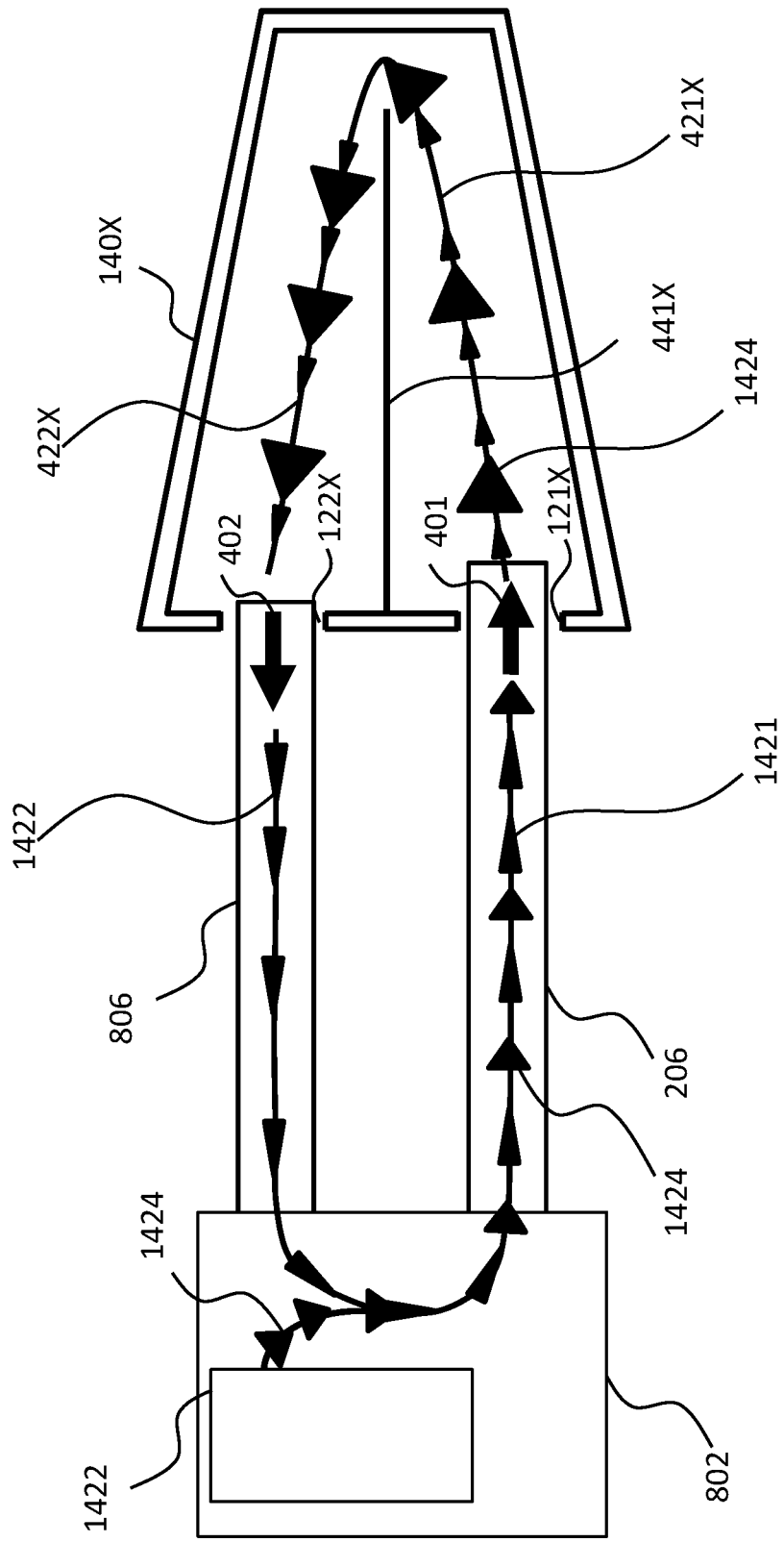
Figure 16:
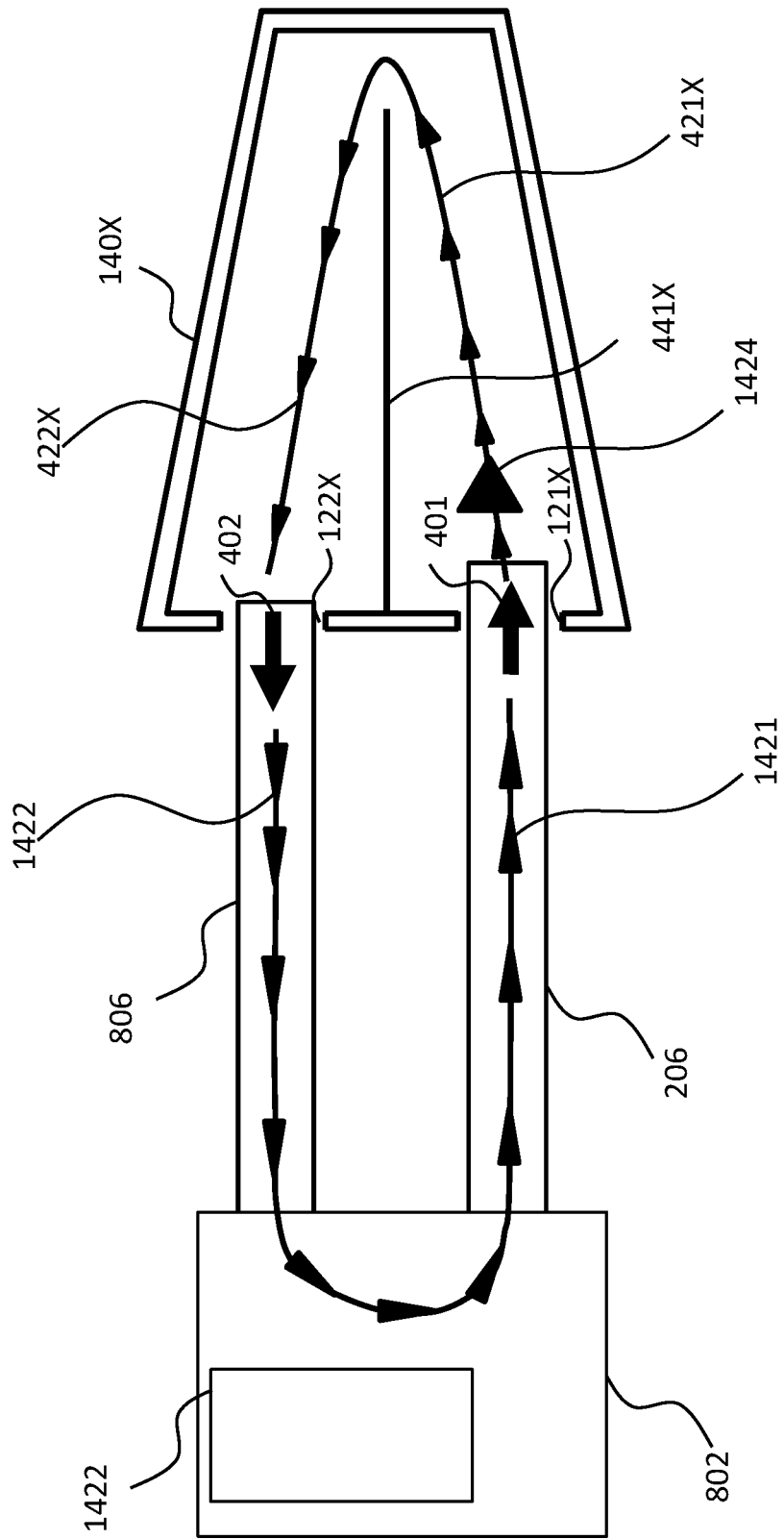
Figure 17:
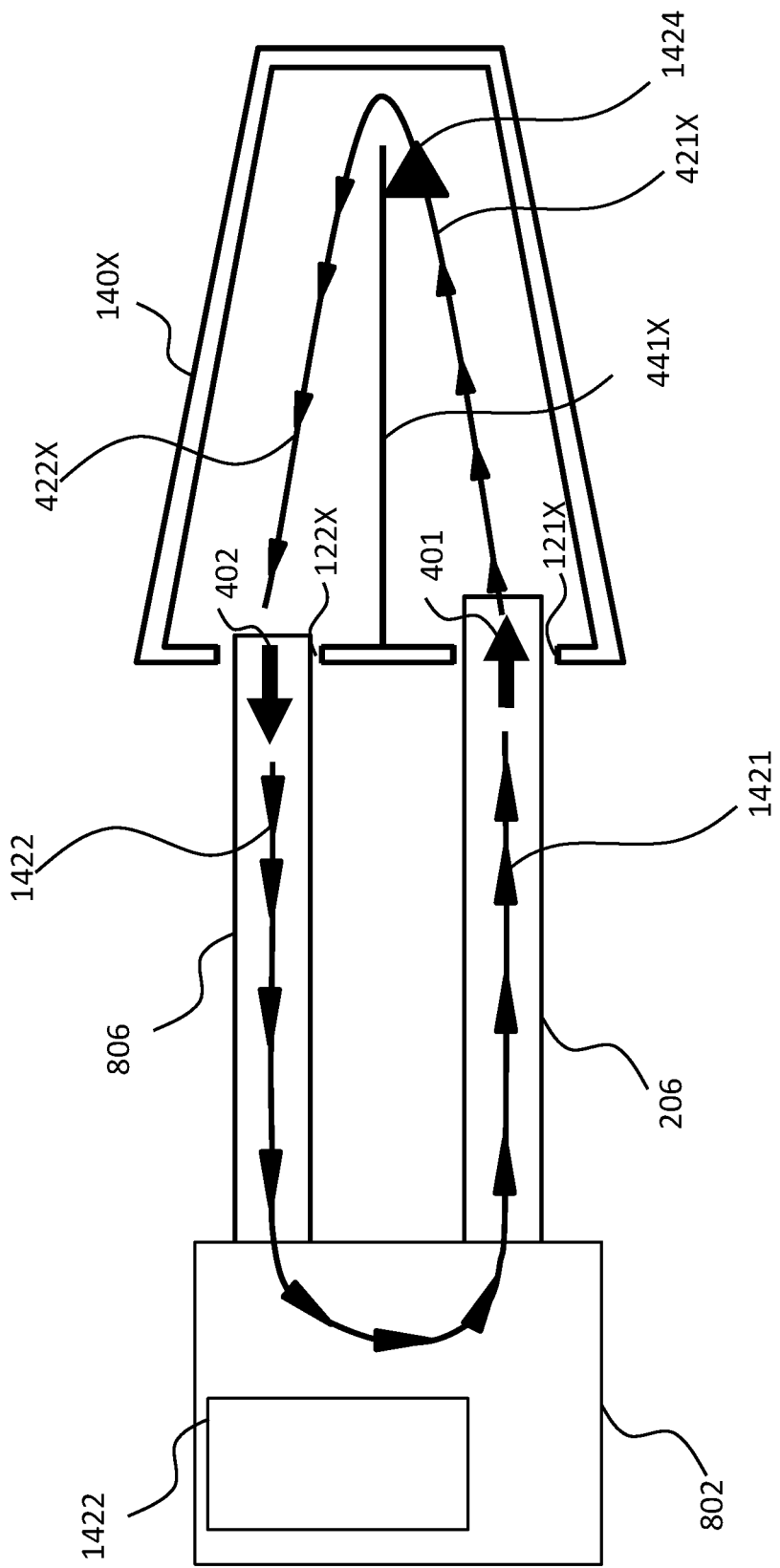
Figure 18:
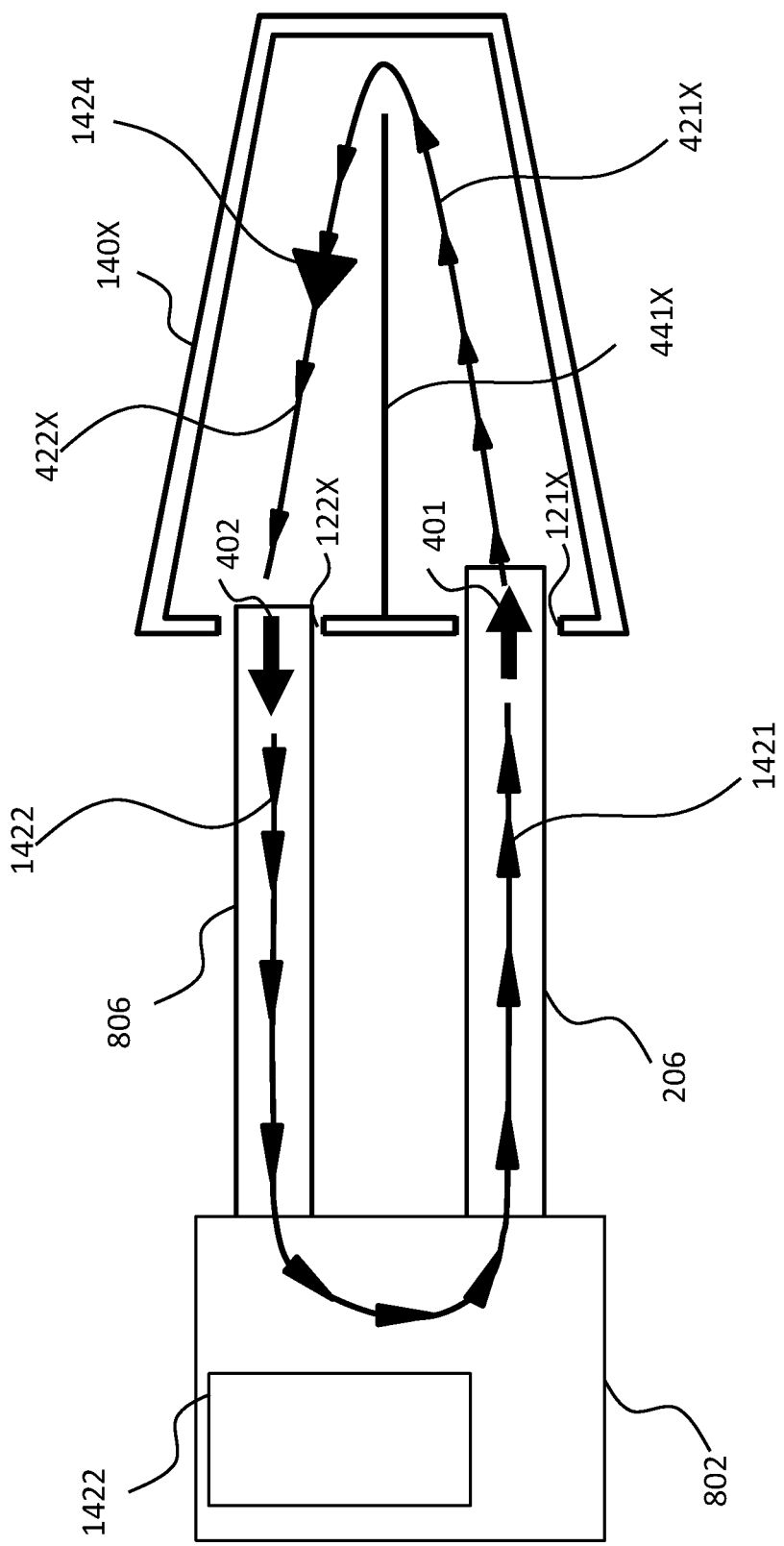
Figure 19:
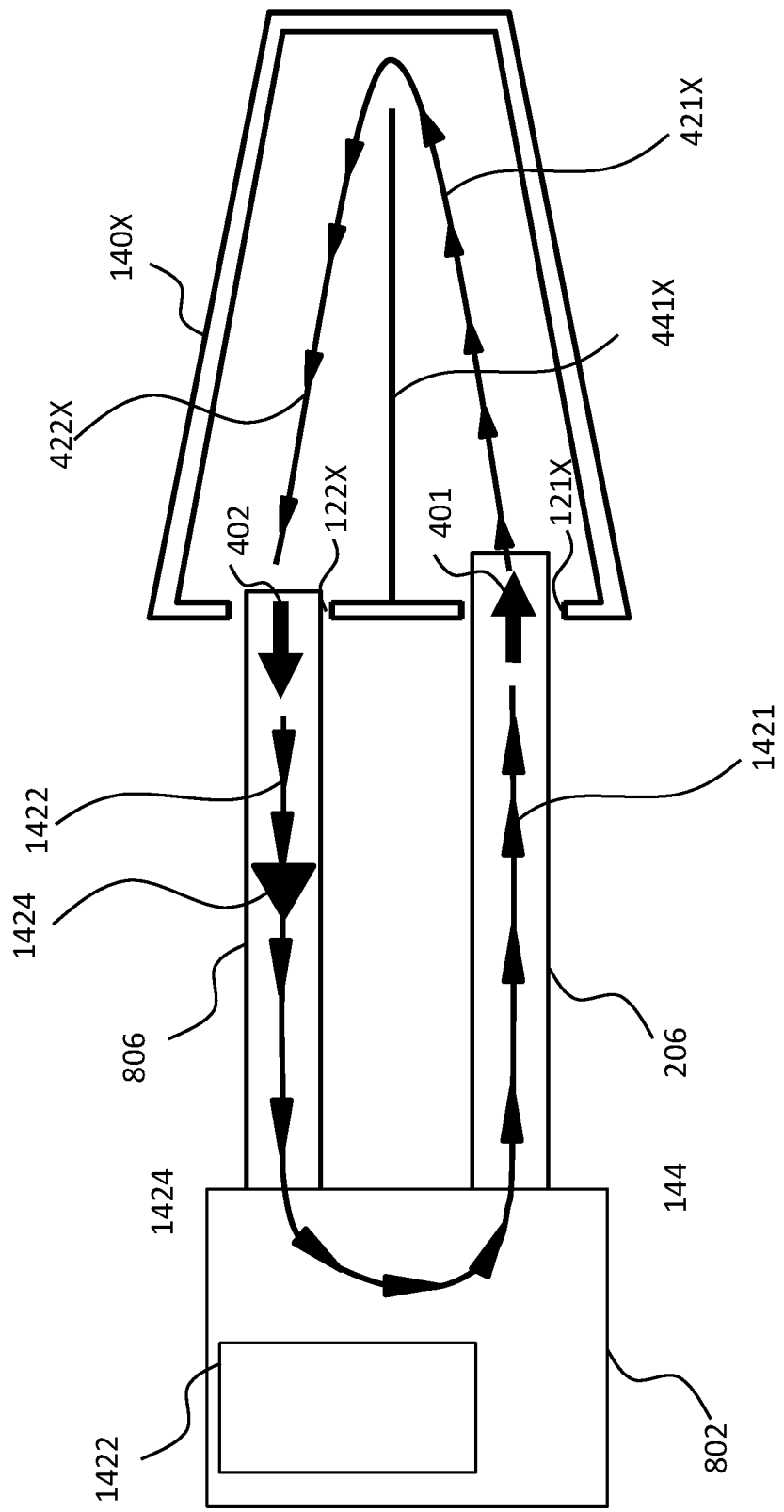

It is also noted that in at least some exemplary embodiments, the amount of therapeutic substance that is introduced into the fluid flow is such that the ratio of therapeutic substance to the non-therapeutic substance/non-active substances of the fluid flow remains substantially unchanged over the single circulation into and out of the cochlea. In this regard, in an exemplary embodiment, the amount of therapeutic substance that is added to the fluid flow is so large that for a given circulation, the tissue of the cochlea can only absorb so much of the therapeutic substance. Such an exemplary scenario is depicted in FIG. 15, where the sizes of the wide arrows do not change. This is not to say that the ratio does not change with respect to the single circulation into and out of the cochlea. The ratio does change because the tissue does absorb some of the drug, but only a relatively small amount relative to the amount of drug in the fluid.

Note also that while the embodiments detailed above have been directed towards the ratio of therapeutic substance to non-therapeutic substance/non-active substance in the fluid flow, in an exemplary embodiment, the ratio may not change because the tissue absorbs both the therapeutic substance and the non-therapeutic substance that creates the fluid flow. Alternatively, and/or in addition to this, the ratio may change but only because the amount of active substance that is absorbed is different than the amount of an active substance that is absorbed.

With respect to the embodiment of FIG. 15, in at least some exemplary scenarios, the fluid flow is circulated a number of times (this concept can be also applicable to the embodiment of FIG. 14 as well). Each time that the fluid flow is circulated, a certain amount of the therapeutic substance is absorbed by the tissue of the cochlea. Thus, each circulation can provide a new "dose" of therapeutic substance to the tissue. Indeed, in this regard, the depiction of FIG. 15 can represent a "slug" of therapeutic substance that is only located in a portion of the total fluid flow, where the slug moves into and out of the cochlea with circulation. In this regard, in an exemplary embodiment, with respect to a single circulation, the slug may only be present in the cochlea for half the time, three quarters of the time, one quarter of the time, etc. It is noted that by the term "slug," it is not meant a solid object. Instead, it is analogous to, for example, a dye marker in the ocean or the like. That said, in some alternate embodiments, the slug can be a solid object. Any arrangement of providing a therapeutic substance in a limited amount with respect to the overall fluid flow can utilize in at least some exemplary embodiments.

FIGS. 16, 17, 18, and 19 conceptually depict movement of a limited slug through the cochlea with respect to a given partial circulation. As can be seen, the slug of therapeutic substance 1424 moves through the cochlea with fluid circulation to the cochlea. In at least some exemplary embodiments, as the slug of therapeutic substance 1424 travels in the cochlea, the local tissue of the cochlea absorbs some of the therapeutic substance.

In an exemplary embodiment, the circulation occurs only partially, at least with respect to a given temporal period. By way of example only and not by way of limitation, in an exemplary embodiment, the circulation can begin so that the slug is moved out of tube 206 into the cochlea, and then out of the cochlea into tube 806. In an exemplary embodiment, the circulation continues until the slug again reaches housing 802. At this point, in an exemplary embodiment, the circulation is stopped for a given period of time. In an exemplary embodiment, the given period of time is a period of time for the efficacy of the therapeutic substance that has been absorbed by the tissue to be lowered so that another dose of therapeutic substance has utilitarian value. By way of example only and not by way of limitation, six hours after the slug has been passed through the cochlea, and the circulation has been shut down, the circulation is reactivated, and the slug is again passed to the cochlea, thus treating the tissue, and upon the slug returning to the housing 802, the circulation is shut down again for another period of time and so on.

It is noted that in an exemplary embodiment, the system 800 can be such that the slug can be recaptured by reservoir and mixing system 1422 and thus taken out of the fluid flow. In an exemplary embodiment, this can have utilitarian value with respect to embodiments where the fluid flow continues even without the therapeutic substance in the fluid. That said, in an exemplary embodiment, this can have utilitarian value with respect to embodiments where, for example, not all of the slug has mixed with the fluid, but some of the slug has mixed with the fluid, and some of the slug that has mixed with the fluid has not been absorbed by the tissue. In this regard, the slug can be recaptured by system 1422 and removed from the fluid flow, such that additional therapeutic substance is no longer being imputed into the fluid flow, but the fluid flow is continued to be circulated such that the therapeutic substance that has been dissolved or otherwise mixed with the fluid flow can be repeatedly circulated through the cochlea. In an exemplary embodiment, whether by sensor or by estimation or by empirical analysis, or by statistical analysis, upon a determination that the therapeutic substance that was mixed with the fluid flow has been substantially absorbed by the cochlea and/or otherwise the amount of therapeutic substance mixed with the fluid flow is no longer sufficient for efficacy, the slug can then be again introduced into the fluid flow and then removed, but the fluid flow can continue circulating. Corollary to this is that in an exemplary embodiment, instead of a slug per se, the system 1422 periodically releases an active substance into the fluid flow, which would not necessarily result in a discrete slug, but would instead result in a quasi-uniform distribution of therapeutic substance into the fluid flow, and then halts the release of active substance in the fluid flow while the fluid flow continue circulating into and out of the cochlea. This can have utilitarian value with respect to metering or otherwise providing control doses of the active substance. Any arrangement of introducing or otherwise managing the amount of therapeutic substance in the fluid flow can be utilized at least some exemplary embodiments.

Figure 20:
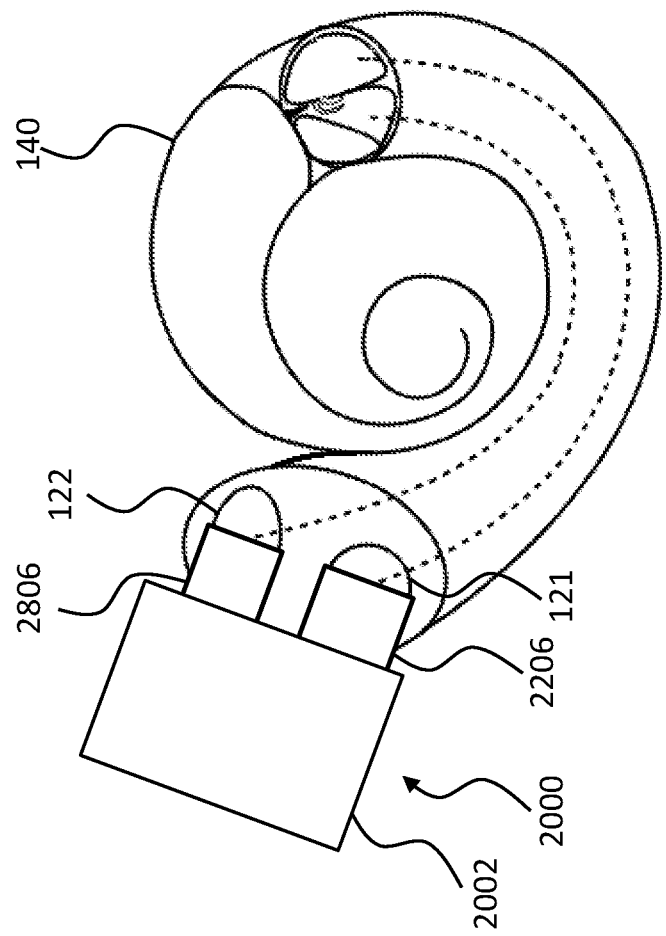
FIGS. 20-21 depict another exemplary embodiment.

As noted above, some exemplary embodiments of the therapeutic substance delivery system can correspond to a device that is configured so as to fit entirely into the middle ear and/or into the middle and inner ear. FIG. 20 depicts such an exemplary embodiment, where delivery system 2000 is a compact device that includes a housing 2002 having inlet and outlet ducts 2806 and 2206 respectively (or vice versa, or, in embodiments where the flow can be reversed, inlet/outlet ducts 2806 and 2206). In an exemplary embodiment, the components of the delivery system 2000 that are located outside of the cochlea proper (where the outer surface of the cochlea that faces the middle ear is part of the cochlea) are all configured to be located entirely in the middle ear cavity. In this regard, instead of the elongate and/or flexible tubes of the system 800 detailed above, here, the ducts of the system 2000 are relatively short (0.1-20 mm in length) and/or relatively stiff. As with the embodiments of the system 800 above, the ducts 2806 and/or 2206 can be placed in fluid communication with the oval and round windows respectively or variously can be placed into fluid communication with the cochlea via separate cochleostomys associated with the respective ducts.

Accordingly, in an exemplary embodiment, the device is configured to be entirely located, collectively, in a middle ear and/or an inner ear of an adult human.

Figure 21:
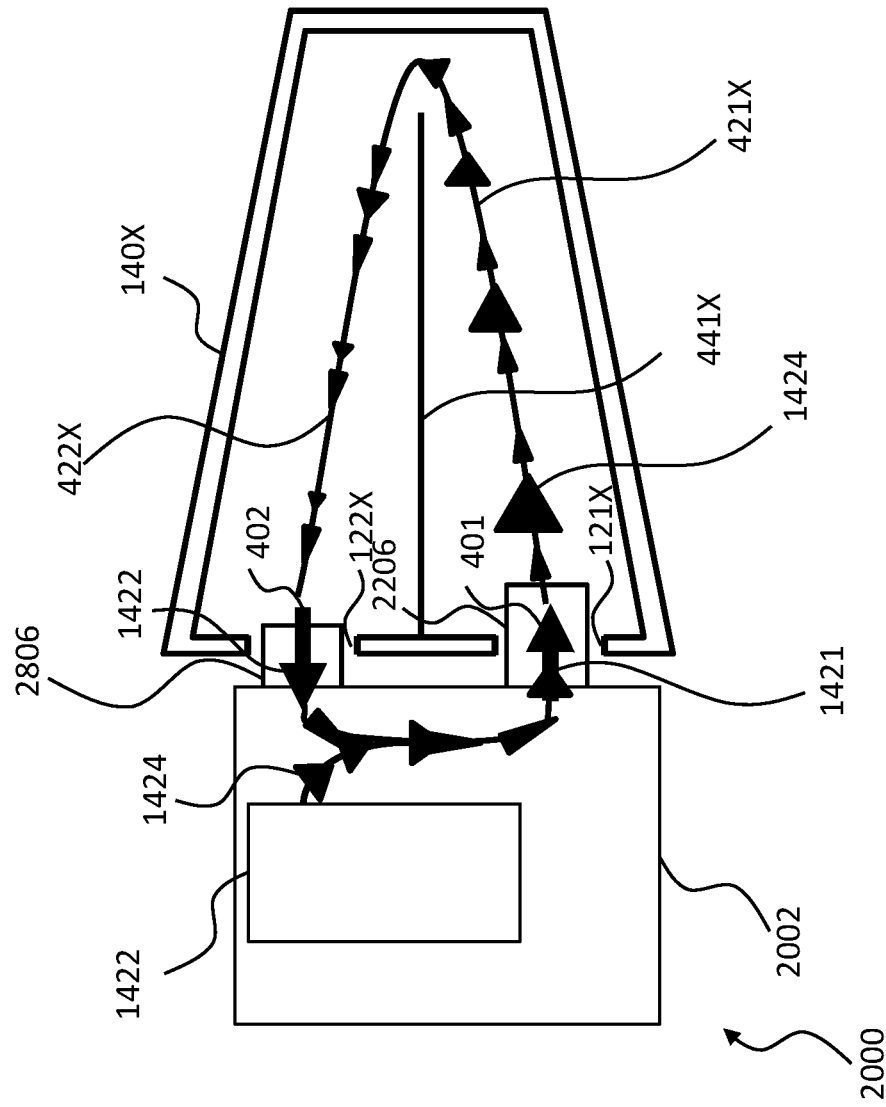

FIG. 21 functionally depicts system 2000 interfacing with cochlea 140X, and also the fluid flow resulting from operation of the system 2000, along with the entrainment of the therapeutic substance 1424 in housing 2002.

Figure 22:
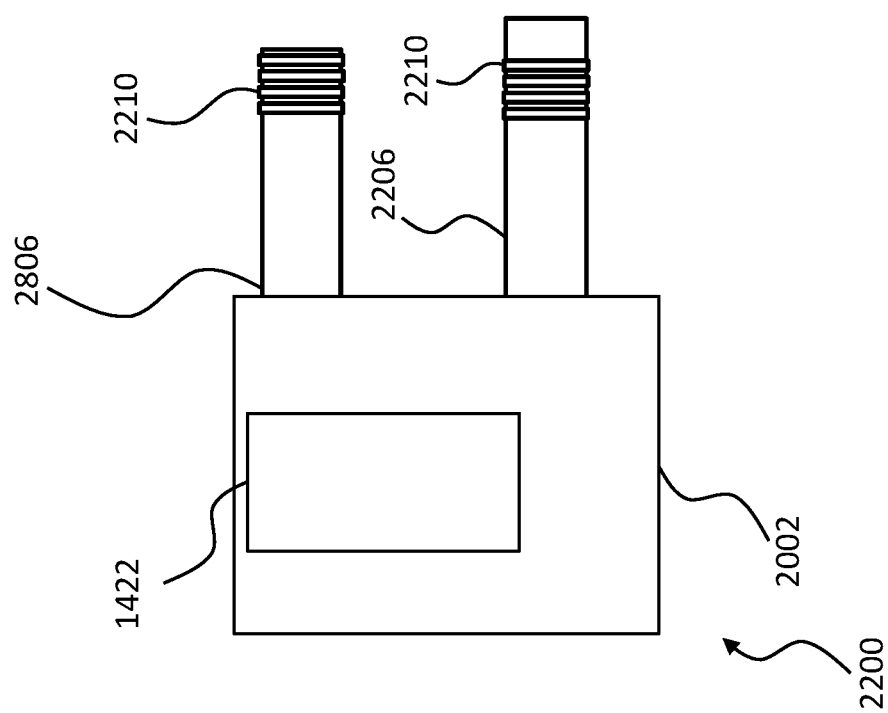
FIGS. 22-26 variously depict other exemplary embodiments.

As noted above, there can be utilitarian value with respect to the therapeutic substance delivery systems being able to close the openings into the cochlea. In this regard, FIG. 22 depicts an exemplary embodiment of a delivery system 2200, which includes a series of O-rings 2210 extending about ducts 2806 and 2206. In an exemplary embodiment, the O-rings are compressible and fill up the holes through the wall of the cochlea through which tubes 2806 and 2206 extend, thereby establishing a leak-proof or at least a substantially leak-proof seal between the system 2200 and the wall of the cochlea. In an exemplary embodiment, the O-rings 2210 are sized and dimensioned to completely fill the round window and/or the oval window. In an alternate exemplary embodiment, the O-rings 2210 are sized and dimensioned to completely fill the holes established via a cochleostomy.

Figure 23:
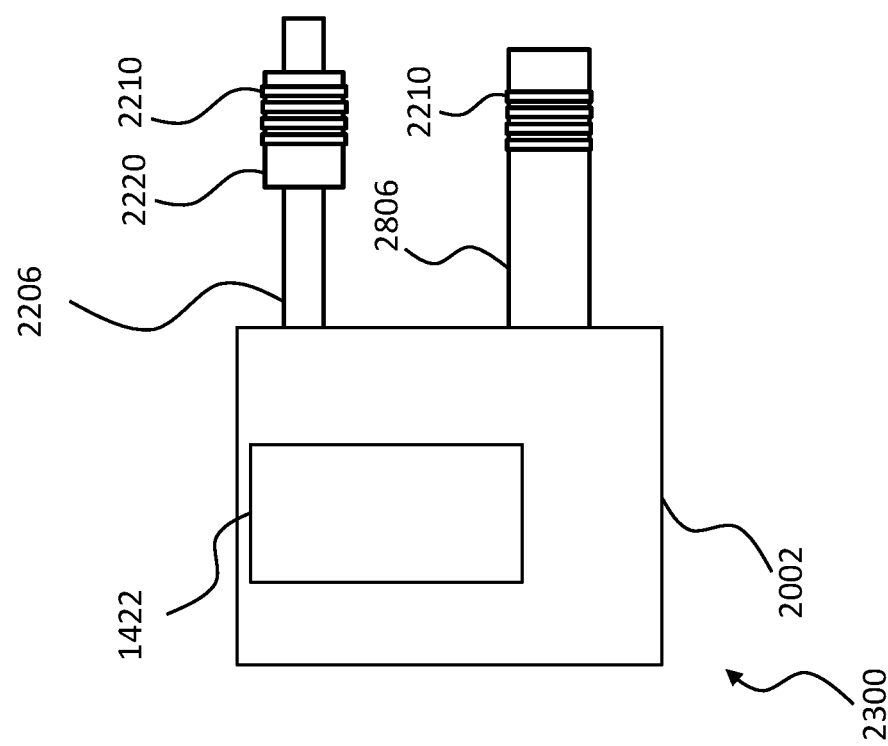

FIG. 23 depicts an exemplary embodiment of a delivery system 2300 which utilizes an adapter 2220 to take up a space between the outer diameter of the tube 2206 and the wall of the cochlea through which tube 2206 extends. In this regard, the outer diameter of 2206 is relatively small relative to the passageway into the cochlea (e.g. through the round or oval window or through the resulting cochleostomy). At least some exemplary embodiments of O-rings 2210 do not have sufficient size to completely fill the hole between the tube 2206 and the wall of the cochlea. Accordingly, adapter 2220 takes up the difference in the space. The embodiment of FIG. 23 makes clear that different connections can be utilized with respect to the same delivery system. FIG. 23 also makes clear that different size tubes can be utilized. In the embodiment of FIG. 23, it can be seen that the return 2806 has a larger diameter than the input tube 2206. This can have utilitarian value with respect to ensuring that the limiting factor to fluid flow is the input path into the cochlea as opposed to the output path out of the cochlea, thus decreasing the possibility of a deleterious pressure rise within the cochlea. That said, in some alternate embodiments, the diameter of the input to can be larger than the diameter of the output tube. Any arrangement that can have utilitarian value with respect to coupling the delivery system to the cochlea and/or establishing fluid flow through the cochlea in a utilitarian and safe manner can be utilized in at least some exemplary embodiments.

Figure 24:
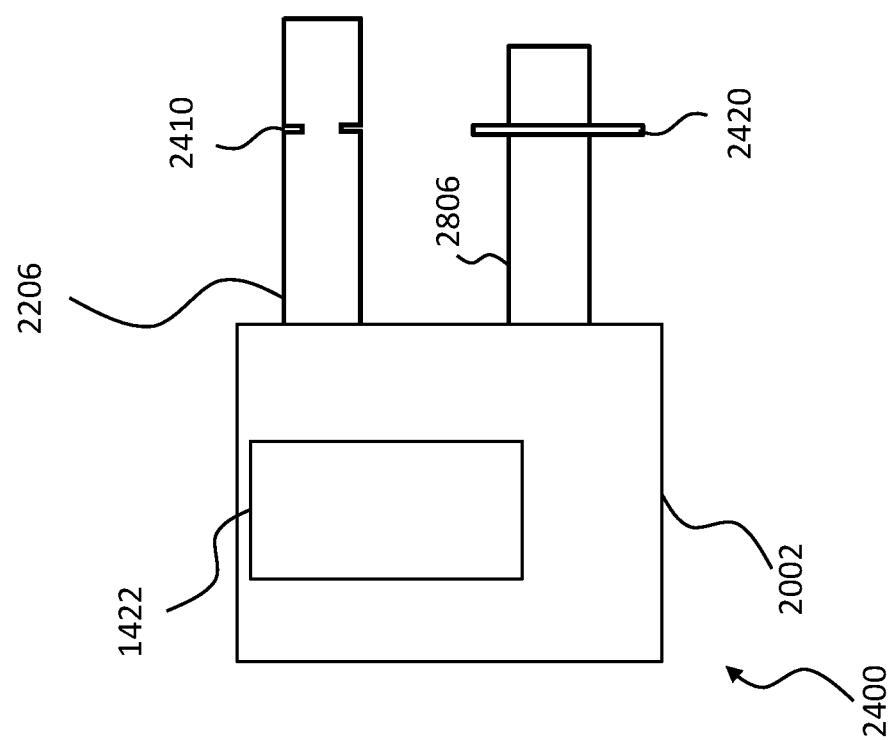

FIG. 24 presents an alternate embodiment of a delivery system, delivery system 2400, that utilizes a flange 2420 that abuts the outside of the cochlea. In an exemplary embodiment, flange 2420 includes an adhesive that bonds to the outside of the cochlea and thus establishes a seal between the cochleostomy and/or the window and the middle ear. In an exemplary embodiment, the flange 2420 remains entirely outside the cochlea. That said, in an alternate embodiment, the flange 2420 can be of a configuration where the flanged can be collapsed or otherwise deformed to fit inside the cochlea and then expand inside the cochlea and thus abut the inside wall of the cochlea to establish a seal. Still further, in an exemplary embodiment, there can be an outer flange and an inner flange which sandwich the wall of the cochlea to establish a seal on the inside and the outside. In an exemplary embodiment, this can be an interference fit vis-à-vis the flanges. Indeed, in this regard, the tubes 2806 and/or 2206 can be interference fitted through the holes through the cochlea to establish a seal. The embodiment of FIG. 24 also provides an alternative embodiment that seals the tubes relative to the cochlea. In this regard, groove 2410 is located on tube 2206. In an exemplary embodiment, groove 2410 is sized and dimensioned so as to essentially snapfit into the hole into the cochlea. Owing to the resiliency of the material of tube 2206, the groove 2410 establishes a seal between the inside of the cochlea and the middle ear. In a sense, groove 2410 operates based on a similar principle of operation of the dual flanges 2420 just described above, except where is the flange extends outward away from the tube, the groove 2410 extends inward from the outer surface of the tube.

Figure 25:
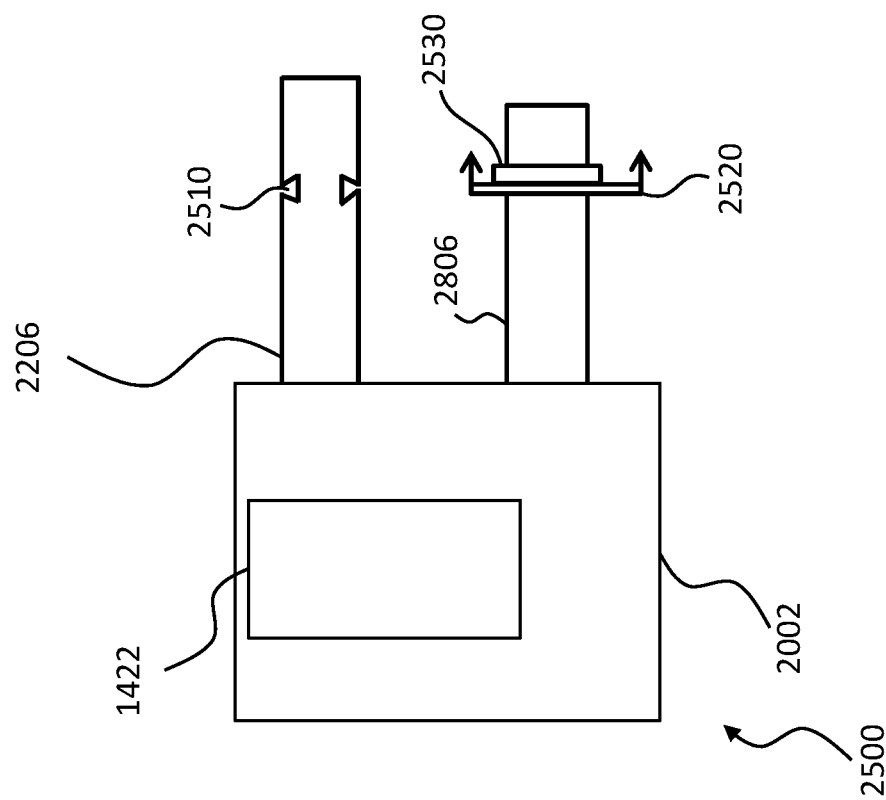

FIG. 25 presents yet another alternate embodiment of a seal arrangement. Here, there is groove 2510. In this embodiment, groove 2510 is configured such that there are relatively sharp edges or otherwise pointed edges at the outer radial position of tube 2206, this owing to the fact that the width of the groove 2510 grows larger with respect to distance from the outer circumference of tube 2206. Because the relatively sharp edges or otherwise pointed edges at the outer periphery of the groove 2510, the outer periphery of group 2510 digs into the tissue that establishes the cochlea wall through which tube 2206 extends. In an exemplary embodiment, the groove 2510 is sized and dimensioned so as to establish a seal. Note further that in an exemplary embodiment, an O-ring can be located in groove 2510 or groove 2410 for that matter, which O-ring can be resilient, which can further enhance sealing.

As can be seen, system 2500 further includes an alternate embodiment of a flanged 2520 that includes spiked anchors at the outer periphery thereof. In an exemplary embodiment, the spikes dig into the wall of the cochlea that separates the cochlea from the middle ear so as to dig in or otherwise hold the flange 2520 against the outer wall of the cochlea. It is noted that in an exemplary embodiment, an O-ring 2560 can be located inboard of the flange 2520 which can abut the outer wall of the cochlea and/or or fit in the hole through which tube 2806 extends to further seal the cochlea (the ring 2530 can be a stepped ring so that a portion thereof fits into the hole, and a portion thereof fits outside the hole on the outer surface of the outside wall the cochlea. It is also noted that while the embodiment of FIG. 25 depicts the anchors facing inboard, alternatively and or in addition to this, the anchors can face outboard, such as in the embodiment where the collapsible flange expands after being inserted in the cochlea, and then the system 2500 is pulled back a bit so that the anchors can dig into the outer wall of the cochlea from the inside.

It is noted that the embodiment of FIG. 25 along with some of the other embodiments just detailed depicts different embodiments for the respective tubes to establish the respective seals. It is noted that in some embodiments, both tubes can utilize the same seals while in other embodiments the tubes can utilize different seals. Any of the seals can be mixed and matched or any of the features of the seals can be mixed and matched and otherwise combined providing that such is enabled by the art and such has utilitarian value.

Thus, in an exemplary embodiment, the device is configured to extend from an outside of the cochlea to at least an interior of the cochlea and secure itself to the cochlea at a location proximate the location of extension to the at least an interior of the cochlea. By way of example only and not by way limitation, barbed spikes on flange 2520 can be located within 1, 2, 3, 4, 5, 6, 7, 8, 9, or 10 millimeters of the cochleostomy (from the geometric center or the geometric edge).

Figure 26:
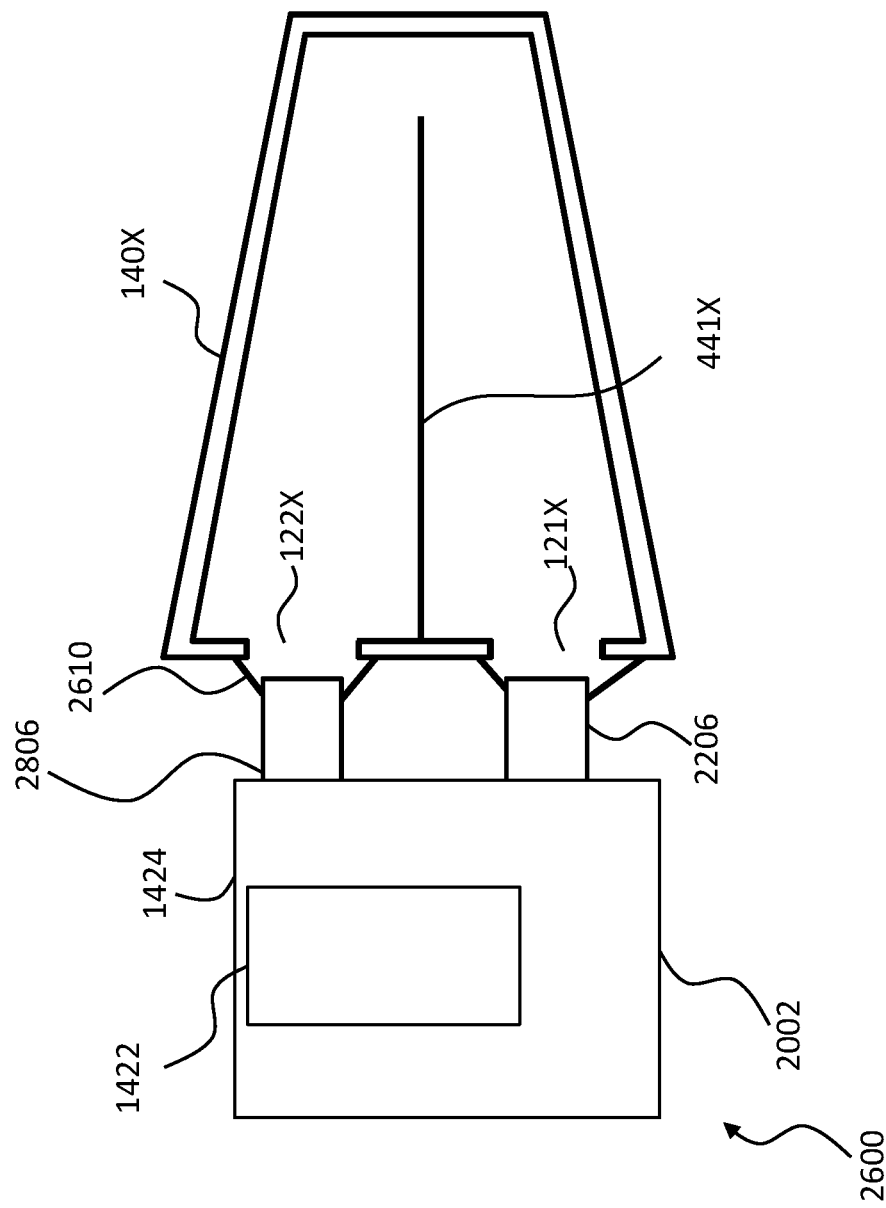

FIG. 26 depicts yet an alternate embodiment of a delivery system 2600 that utilizes a shroud 2610 extends about the respective tubes. As can be seen, no part of the system 2600 extends into the cochlea. In an exemplary embodiment, an adhesive or the like is located on the outer edges of the shrouds 2610. Thus, in an exemplary embodiment, the device is configured to extend from an outside of the cochlea to at least a location proximate an opening into an interior of the cochlea and secure itself to the cochlea at a location at or proximate the location into an interior of the cochlea.

In view of the above, it can be seen that in an exemplary embodiment, there is a device, such as a prosthesis, that includes a drug delivery device, such as by way of example only and not by way of limitation, systems 800, 2000, 2200, 2300, 2400, 2500, and/or 2600 configured to simultaneously interface with a scala tympani and a scala vestibuli of a cochlea. Still further, it can be seen that in some embodiments, the device is configured to induce complete circuit circulation from the scala tympani to the scala vestibuli and/or vice versa, thereby distributing drug within the cochlea. In this regard, it is noted that in at least some exemplary embodiments of the delivery system 200 detailed above, in some instances, the therapeutic drug or other therapeutic substance delivered to the cochlea congregate or otherwise pool at the basal portion of the cochlea, or at least a substantial amount thereof, relative to the amount that reaches the apical portion. In this regard, with respect to the turns of the cochlea, it is possible that in at least some exemplary scenarios, the amount of drug that reaches the area after the X° turn of the cochlea with respect to the given duct into which the therapeutic substance is initially delivered may be Y less than that which reaches tissue before the X° turn. In an exemplary embodiment, X is 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 325, 350, 375, 400, 425, 450, 475, or 500. In an exemplary embodiment, Y is 5, 10, 15, 20, 25, 30, 35, 40, 45, 50, 55, 60, 65, 70, 75, 80, 85, 90, 95, 96, 97, 98, 99, or 100%. Thus, it can be understood that in at least some exemplary embodiments, Y can be very much. This can have less than maximum utilitarian results in that portions of the cochlea may not be efficaciously treated by the therapeutic substance, such as the portions beyond the X° turn.

Alternatively, with respect to the embodiments herein that utilize circulation or otherwise induce circulation, because the therapeutic substance is driven with the fluid flow, at least partially, much more of the substance can be delivered to the more apical portion of the cochlea. Moreover, much more of the therapeutic substance can be delivered to the opposite duct relative to the duct into which the therapeutic substance is directly introduced (e.g., if the drug is introduced into the vestibular duct, the duct receiving deficient or otherwise less therapeutic substance would be the tympanic duct, and vice versa). Indeed, in some exemplary scenarios of utilization of the system 200, little to no therapeutic substance will reach the opposite duct.

In at least some of the exemplary embodiments utilizing the circulation, the amount of drug that reaches the area after the X° turn of the cochlea with respect to the given duct into which the therapeutic substance is initially delivered is more than A of that which reaches tissue before the X° turn. In an exemplary embodiment, A is 50, 55, 60, 65, 70, 75, 80, 85, 90, 95, 96, 97, 98, 99, or 100%. Thus, it can be understood that in at least some exemplary embodiments, the amount of drug that reaches the area after the turn at issue is substantially or otherwise effectively the same as that which reaches the portion of the cochlea before the turn. Thus, in at least some exemplary embodiments, the teachings herein utilizing circulation can deliver about the same amount of drug to all areas of the cochlea regardless of location, or at least with respect to the area between the inlet and the egress of the fluid flowing into and out of the cochlea. In any event, in at least some embodiments where the device is a therapeutic substance delivery device, the device is configured to drive the therapeutic substance to a juncture of the scala tympani and the scala vestibuli. In an exemplary embodiment, the device is configured to drive the therapeutic substance to a juncture of the scala tympani and the scala vestibuli in an amount that is at least about or is about 99, 98, 97, 96, 95, 94, 93, 92, 91, 90, 89, 88, 87, 86, 85, 84, 83, 82, 81, 80, 75, 70, 65, 60, 55, or 50% of the amount that first enters the cochlea or any value or range of values therebetween in 0.1 percent increments. In an exemplary embodiment, the device is configured to drive the therapeutic substance to a juncture of the scala tympani and the scala vestibuli in an amount that is an effective amount with respect to treating tissue at that juncture. In an exemplary embodiment, the driving starts at the basal region of the cochlea, such as, by way of example only and not by way limitation, at a location at or proximate the round window and/or the oval window.

As can be seen above, such as with respect to systems 800, 2000, 2100, 2600, etc., the device can include a fluid inlet and a fluid outlet respectively configured to be placed into fluid communication with, respectively, the scala tympani or the scala vestibuli, and/or vice versa. Also as can be seen by these exemplary embodiments, the device can be configured to permanently simultaneously interface with a scala tympani and a scala vestibuli of a cochlea so as to enable, respectively, ingress and egress and/or vice versa of perilymph from/to the cochlea during the period of permanent interfacing. By way of example only and not by way of limitation, it is noted that in an exemplary embodiment, the systems detailed herein are configured to "tap" the cochlea to enable the natural perilymph to be flowed out of the cochlea and into the system. In this regard, the fluid flow to which the therapeutic substances are added can be a fluid flow of perilymph. In at least some exemplary embodiments, it is a natural perilymph that is utilized. That said, in some alternate embodiments, the fluid flow can be a combination of a natural perilymph and a perilymph equivalent that is a non-active substance. Any arrangement of fluid that can be combined with an active or otherwise therapeutic substance to enable the teachings detailed herein can be utilized at least some exemplary embodiments. In this regard, by way of example only and not by way of limitation, in an exemplary embodiment, the systems detailed herein can be configured with a reservoir of active substance and separate reservoir of a non-active substance. The reservoir of non-active substance can be utilized to provide additional fluid of the fluid flow, and the reservoir of active substance can be utilized to provide the active substance that is entrained into the fluid flow. In an exemplary embodiment, the system can be configured so as to separately access the separate reservoirs when there is utilitarian value with respect to adding additional non-active substance and/or active substance. In an exemplary embodiment, the system is configured such that the active substance can be mixed with the non-active substance prior to introduction of the mixture into the fluid flow. Alternatively, in some alternate embodiments, the system is configured such that the active substance is mixed directly with the fluid flow and the non-active substance is separately mixed with the fluid flow. Alternatively, in some alternate embodiments, the system is configured such that the active substance and the non-active substance can be mixed simultaneously with the fluid flow.

Thus, in an exemplary embodiment, the aforementioned device can be configured to extract perilymph from the cochlea, mix the drug with the extracted perilymph, and insert the mixture into the cochlea. Also, in an exemplary embodiment, the device is configured to move a non-perilymph substance from external to the cochlea to inside the cochlea via the circulation. As noted above, in at least some exemplary embodiments, the non-perilymph substance can be a therapeutic substance such as, by way of example only and not by way of limitation, a drug. That said, in some alternate embodiments, the non-perilymph substance can also be a non-therapeutic substance.

Figure 27:
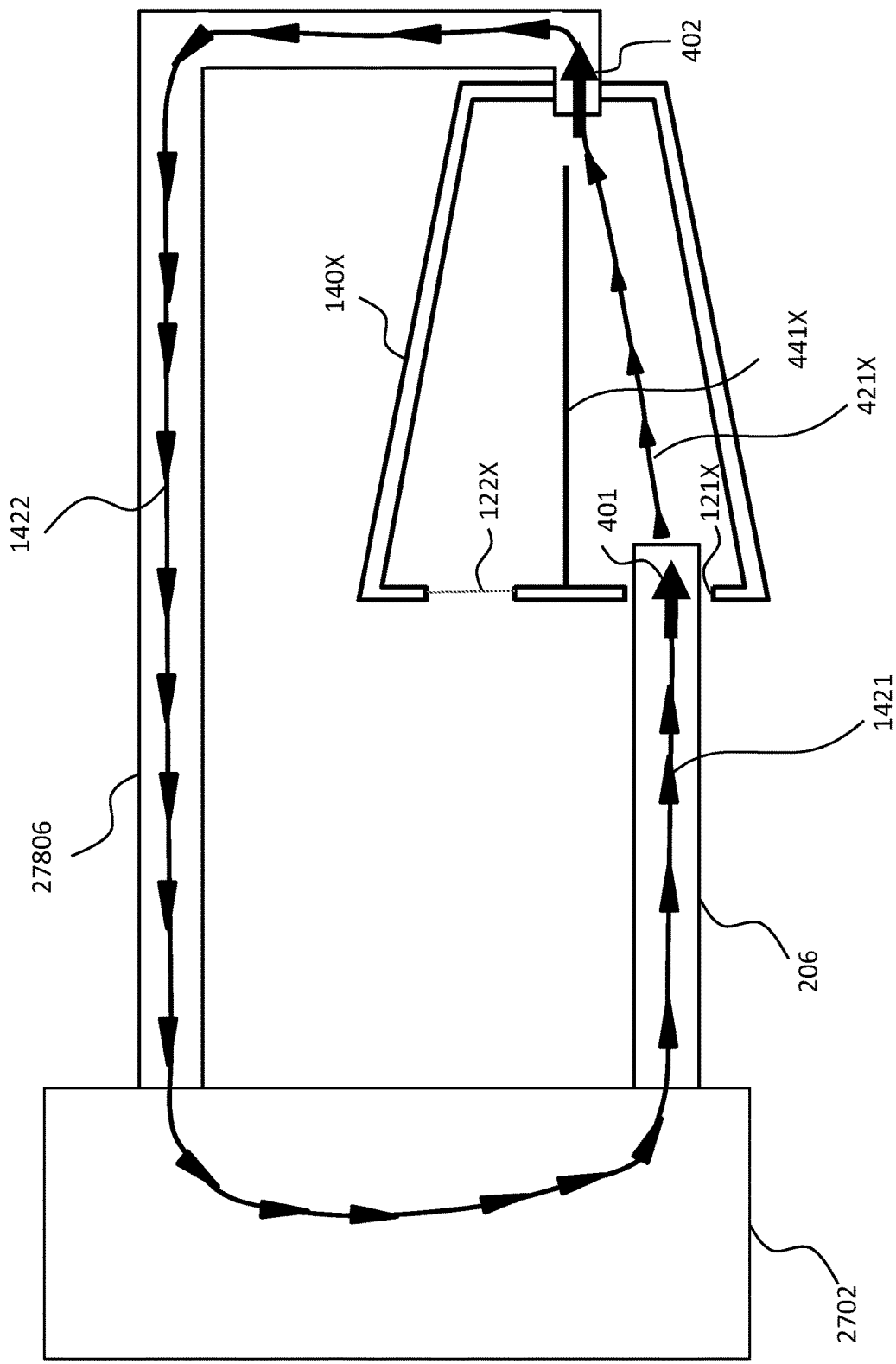
FIGS. 27 and 28 variously depict other exemplary embodiments in use.

It is noted that while the embodiments above have focused on a system that delivers a fluid flow to the cochlea and removes the fluid flow from the cochlea at the basal portion of the cochlea, in an alternative embodiment, the removal and/or delivery can be located at another location. In this regard, FIG. 27 depicts an exemplary delivery system where the delivery tube 206 extends through the round window 121X such that flow 421X extends through only one duct of the cochlea (the tympanic duct in this embodiment, where in alternative embodiments, it could be the vestibular duct). As can be seen, tube 27806 interfaces with the apical portion and/or helicotremaof the cochlea such that the fluid flow exits the cochlea at arrow 402 and becomes fluid flow 1422, wherein tube 27806 extends to the housing 2702, which housing can functionally correspond to the housing 802 detailed above, etc. Accordingly, fluid is circulated through the cochlea, but only a portion thereof. It is noted that while the embodiment of FIG. 27 depicts the tube 27806 interfacing at the apical portion of the cochlea (where, in some embodiments, that tube can be a return tube while in other embodiments, that tube can be a delivery tube), in an alternate embodiment, tube 27806 can interface at a another location of the cochlea prior to the apical portion (i.e., between, with respect to the spiral of the cochlea, the basal portion and the apical portion with respect to a given duct) or after the apical portion. By way of example only and not by way of limitation, in an exemplary embodiment, tube 27806 can interface with the cochlea, such as via a cochleostomy, at a location at about at the turn Z°, where, in an exemplary embodiment, Z is 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 325, 350, 360, 375, 400, 425, 450, 475, 500, 525, 550, 575, 600, 625, 650, 675, 700, 725, 750, 775, 800, 810, 820, 830, 840, 850, 860, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, or 900, 901, 902, 903, 904, 905, 906, 907, 908, 909, 910, 911, 912, 913, 914, 915, 916, 917, 918, 919, 920, 925, 930, 935, 940, 945, 950, 955, 960, 965, 970, 975, 980, 990, 1000, 1050, 1100, 1150, 1200 degrees or any value or range of values therebetween in 0.25° increments (e.g., 48.5°, 92°, 56 to 293 degrees, etc.—it is noted that on average, there are 2.5 turns of the cochlea, but that is just an average).

In an exemplary embodiment, the second cochleostomy where tube 27806 interfaces with the cochlea can be at any location between the apical portion and the basal portion of the cochlea with respect to any of the ducts. In an exemplary embodiment, the second cochleostomy can be located at any location of about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 325, 350, 375, 400, 425, 450, 475, 500, 525, 550, 575, 600, 625, 650, 675, 700, 725, 750, 775, 800, 810, 820, 830, 840, 850, 860, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, or 900 degrees from the apical portion of the cochlea to the basal portion of the cochlea or any value or range of values therebetween in 0.25° increments (e.g., 77.25°, 92°, 56 to 293.75 degrees, etc.).

Accordingly, in an exemplary embodiment, one or more of a first turn and/or second turn cochleostomy can be utilized to access the cochlea. It is also noted that in an exemplary embodiment, utilization of an access location of the cochlea at a location away from the basal location can utilize the fact that the fluid flow can flow downstream or otherwise downward with respect to gravity, corollary to this is that in at least some exemplary embodiments, some scenarios of use and thus some embodiments can include devices to enable at least partial removal of perilymph of fluid from the cochlea and then the introduction of fluid at a "higher" location, and because there is less perilymph in the cochlea, including no perilymph or substantially no perilymph, the fluid introduced at the higher location with the therapeutic substance will flow downward. Accordingly, in an exemplary embodiment, there is a method that includes at least partially reducing or otherwise removing perilymph from the cochlea, including emptying the cochlea of perilymph, and then introducing/reintroducing the perilymph including the therapeutic substance into the cochlea at a higher location and allowing the fluid containing the therapeutic substance to flow downward, thus exposing various locations of the cochlea to the therapeutic substance.

In any event, in at least some exemplary embodiments, flow can be achieved via a single port. By way of example only and not by way of limitation, in a modified embodiment of system 200, the delivery tube 206 can be both a delivery tube and a return tube. In an exemplary embodiment, modified system 200 can be configured to suck perilymph out of the cochlea. In an exemplary embodiment, the perilymph is partially or completely sucked out of the cochlea or otherwise removed from the cochlea, then entrained with a therapeutic substance, and then reintroduced into the cochlea, where the therapeutic substance is generally evenly dispersed within the fluid that is reintroduced into the cochlea, or at least otherwise contains an effective distribution of therapeutic substance such that most if not all of the portions of the cochlea will be treated with a therapeutic substance.

In an exemplary embodiment, there is of a reservoir that is part of the device that receives perilymph that is extracted from the cochlea. In an exemplary embodiment, the implant is configured to extract perilymph from the cochlea at a relatively low rate, that permits the backfill through natural introduction of CFS (cerevial spinal fluid). Upon taking a desired amount of perilymph out of the cochlea, and entraining or otherwise mixing the therapeutic substance therein, the cochlea is then refilled with the perilymph from the reservoir, and the CFS is thus expelled, in whole or in part, from the cochlea. In an exemplary embodiment, the inflow of perilymph at one end of the cochlea can expel the CFS out the other end. The end result may be that at the end of the reinsertion of the perilymph, 70, 75, 80, 85, 90, or 95 percent of the fluid in the cochlea is perilymph, and the remaining is CFS (so as to reduce the likelihood that the perilymph will be expelled out the exit). That is, in an exemplary embodiment, perilymph is siphoned from the cochlea, and then replaced in the cochlea. That said, in an exemplary embodiment, CFS can be the medium that is introduced into the cochlea, such as in a scenario where the perilymph has been depleted (e.g., a so called "gusher" occurs during surgery). That is, in an exemplary embodiment, CFS in what is used to refill the cochlea. Indeed, in an exemplary embodiment, CFS can be affirmatively introduced to the cochlea, as opposed to relying on natural diffusion. This can enable an increase in the flow rates of perilymph into and/or out of the cochlea beyond those detailed above.

It is also noted that in some embodiments, the tube 206 can also interface the cochlea at a location other than the basal portion. In an exemplary embodiment, any of the aforementioned turns can be a location where a cochleostomy can be present and the tube 206 can interface there with. Any location of accessing the cochlea that can enable the circulation can be utilized in at least some exemplary embodiments.

Thus, in view of the above, the aforementioned device can be configured to interface with at least one of the scala tympani or the scala vestibuli at a location at or above a first turn, a 1.25 turn, a 1.5 turn, a 1.75 turn, a second turn, a 2.25 turn or a 2.5 turn of the cochlea.

With respect to the teachings detailed herein with respect to a prosthesis configured to circulate perilymph within a cochlea, in an exemplary embodiment, such a prosthesis can be as seen above, a drug delivery system or the like. It is briefly noted that in at least some exemplary embodiments, the prosthesis can also include components configured to evoke a hearing percept, such as by way of example only and not by way limitation, a cochlear implant and/or a direct acoustic cochlear stimulator, etc. Some additional details of such will be described in greater detail below.

Still consistent with the teachings detailed above, in an exemplary embodiment, the prosthesis includes a device that is configured extract perilymph from the cochlea, mix a non-perilymph substance with the extracted perylimph (e.g., a therapeutic substance, such as by way of example only and not by way of limitation, a perilymph soluble drug), and insert the mixture into the cochlea.

As noted above, in at least some exemplary embodiments, the circulation systems detailed herein can include a pump configured to drive the circulation of the perilymph. In an exemplary embodiment, this can be an impeller. In an exemplary embodiment this can be a turbine. In an exemplary embodiment, these components can be driven by an electrical source of the like. In an exemplary embodiment, these components can be driven by manual force input along the lines of that detailed above with respect to system 200. In an exemplary embodiment, these components can be driven via a magnetic field or the like along the lines of that detailed above with respect to system 200. Any device, system and/or method that will enable the circulation can be utilized at least some exemplary embodiments.

It is noted that the embodiment of FIG. 20 can have utilitarian value with respect to limiting or otherwise minimizing the amount of perilymph that is removed from the cochlea at any given time. In this regard, the embodiments of system 800 can require or otherwise result in more perilymph being removed from the cochlea than that of the embodiment of system 2000. In this regard, by way of example, this is because tubes 806 and 206 are substantially longer than ducts 2806 and 2206. Indeed, in an exemplary embodiment, the device is configured such that when the device is attached to a cochlea, the device establishes a fluid path from the scala vestibuli to the scala tympani outside the cochlea in at least substantially the shortest path possible.

By way of example only and not by way of limitation, in an exemplary embodiment, the fluid path from a first opening into the cochlea to a second opening into the cochlea is no more than 2, 3, 4, 5, 6, 7, 8, 9, 10, 11, 12, 13, 14, 15, 16, 17, 18, 19, 20, 21, 22, 23, 24, 25, 26, 27, 28, 29, or 30 mm.

That said, at least some embodiments are such that the system expands a perilymph containing volume within the recipient beyond that established by the cochlea. In an exemplary embodiment, the volume is expanded by amount of B, where B is about 1, 2, 3, 4, 5, 6, 7, 8, 9, 10, 11, 12, 13, 14, 15, 16, 17, 18, 19, 20, 25, 30, 35, 40, 45, 50, 55, 50, 55, 60, 65, 70, 75, 80, 85, 90, 95, 100, 105, 110, 115, 120, 125, 130, 135, 140, 145, 150, 155, 160, 165, 170, 175, 180, 190, 200, 210, 220, 230, 240, or 250%. In an exemplary embodiment, the volume is expanded by no more than amount of B. In an exemplary embodiment, the volume is expanded by more than an amount of B. It is noted that while this embodiment is disclosed in relation to embodiments that provide therapeutic substance into the cochlea, in some alternate embodiments, such can be utilized independent of such a feature, such as, by way of example only and not by way of limitation, to simply reduce and/or increase pressure inside the cochlea and/or to enable an artificial hearing percept to be evoked utilizing a hearing prostheses.

To be clear, embodiments can include a means for interfacing with a cochlea, and a means for distributing a therapeutic substance within a cochlea. In some embodiments, the means for interfacing with the cochlea includes a means for establishing separate fluid communication between the scala tympani and an outside of the cochlea and a scala vestibuli and the outside of the cochlea. In at least some embodiments, the means for distributing the therapeutic substance within the cochlea is also a means for distributing the therapeutic substance effectively equally within the cochlea. In at least some embodiments, the device includes a shunt that establishes fluid communication from the scala tympani to the scala vestibuli of the cochlea. In an exemplary embodiment, the device induces fluid flow from the scala tympani to the scala vestibuli, and/or vice versa, of the cochlea.

Figure 28:
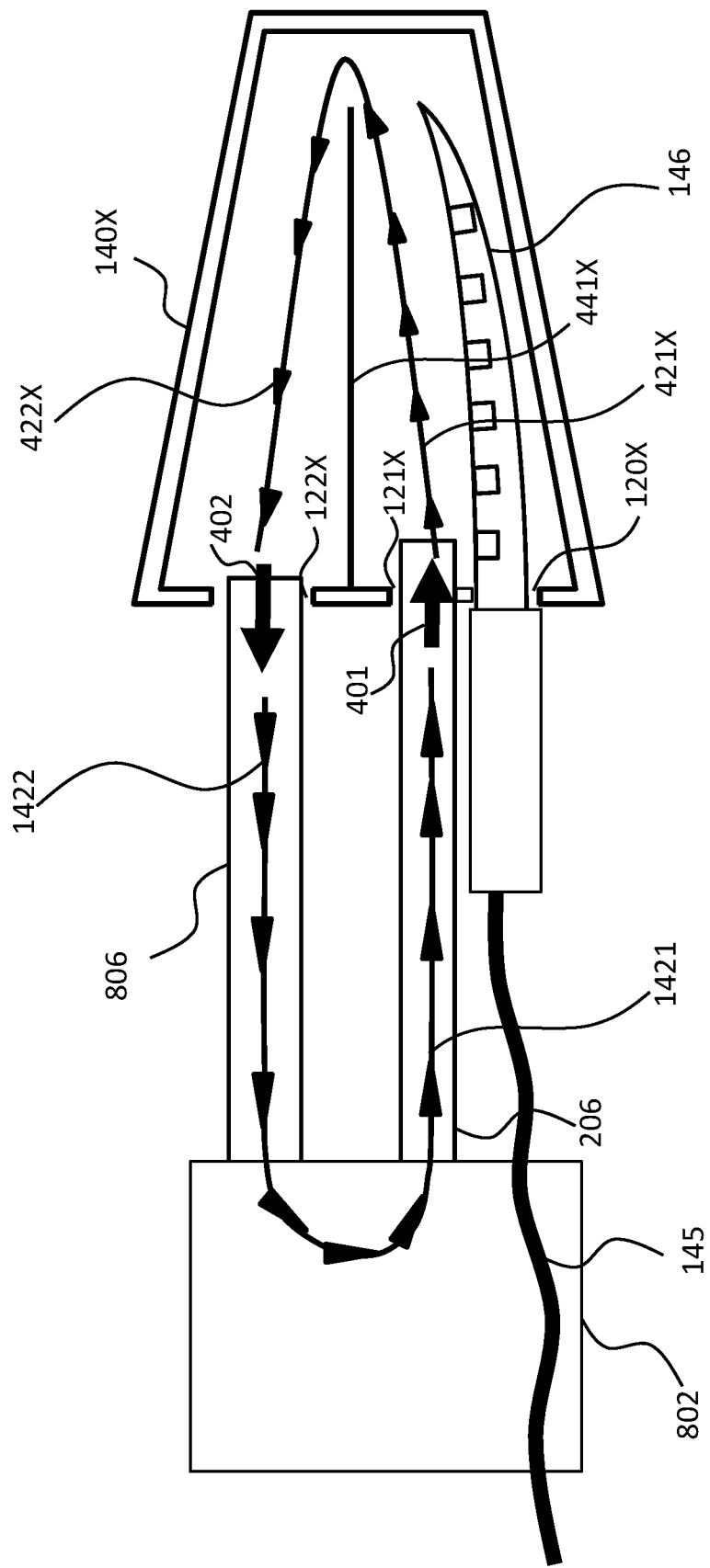
Figure 29:
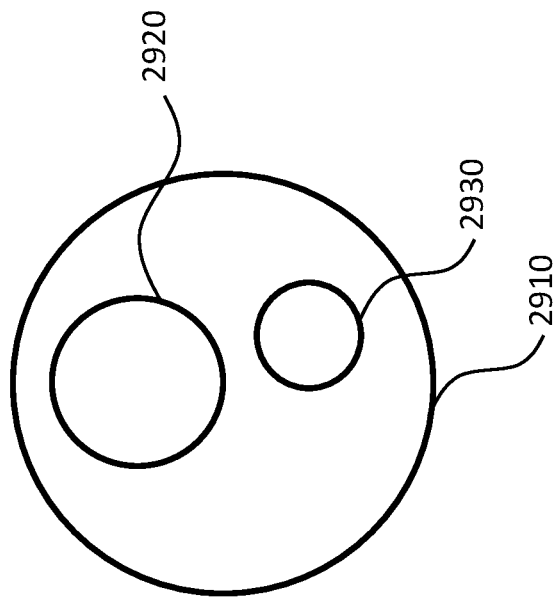
FIGS. 29-31 variously depict other exemplary embodiments.

As noted above, at least some exemplary embodiments of the therapeutic substance delivery systems described herein and/or variations thereof can be utilized in conjunction with a hearing prosthesis. In this regard, FIG. 28 functionally depicts an exemplary scenario where the delivery system 800 is utilized in conjunction with a cochlear implant, as represented by lead 145 and electrode array 146 being located in cochlea 140X. In this exemplary embodiment, a separate cochleostomy 120X is provided in the cochlea to access the scala tympani. This separate cochleostomy is separate from the round window 121X, as can be seen. That said, in an exemplary embodiment, the same access port can be utilized for both the delivery system 800 and the cochlear implant. In an exemplary embodiment, a seal arrangement and/or coupling arrangement can be provided that separately seals tube 206 relative to the access port and electrode array 146 or related component relative to the access port. FIG. 29 depicts an exemplary embodiment of a seal-coupling component 2910 in the form of a circular disk, although in other embodiments, the component 2910 approaches a cylindrical like depth (into/out of the page), and in other embodiments, the component 2910 has a cylindrical depth. In an exemplary embodiment, the component 2910 is fit into a circular cochleostomy that provides an access port to the tympanic duct or the vestibular duct. The component 2910 is configured to seal against the cochlea wall with respect to the outer circumference thereof. As can be seen, component 2910 includes two holes 2920 and 2930 which extend completely through the component 2910. In an exemplary embodiment, holes 2920 and 2930 provide access for the particular tube of the delivery system and the array of the cochlear implant. In an exemplary embodiment, those components have seals that seal the insides of the holes 2920 and 2930 and/or the component 2910 has a seal that seals the holes when the tubes and the array interface therewith or otherwise are placed proximate therewith. In an exemplary embodiment, component 2910 also provides an anchor or the like for the particular tube of the delivery system and/or the cochlear implant.

Figure 30:
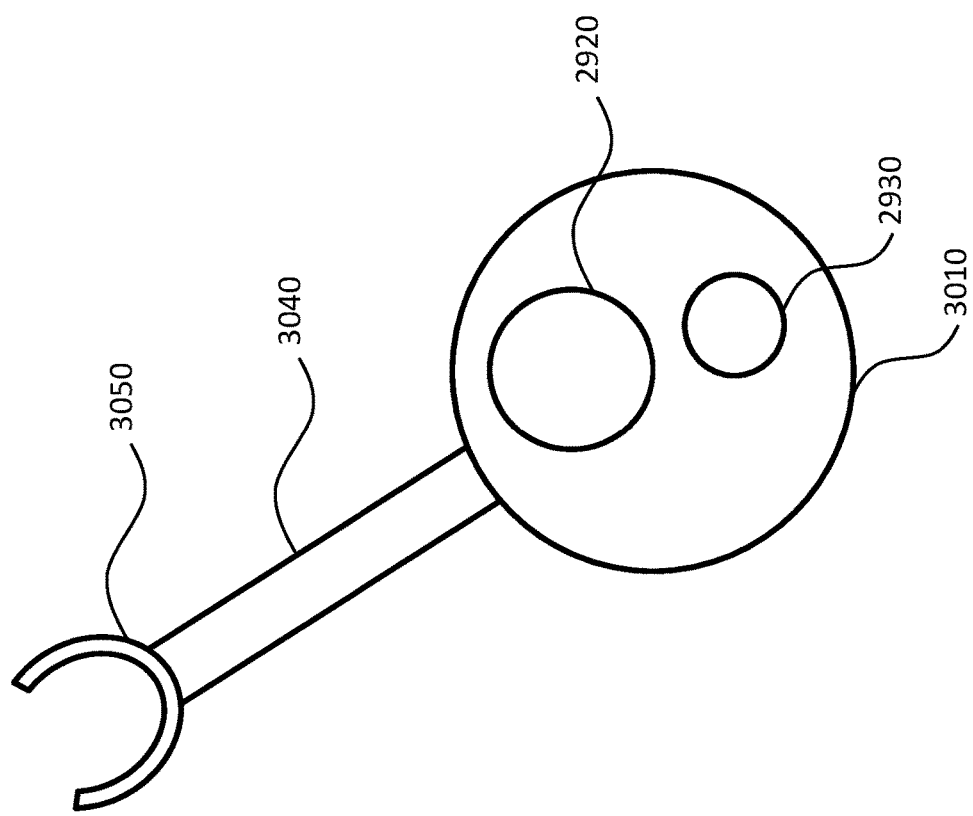
Figure 31:
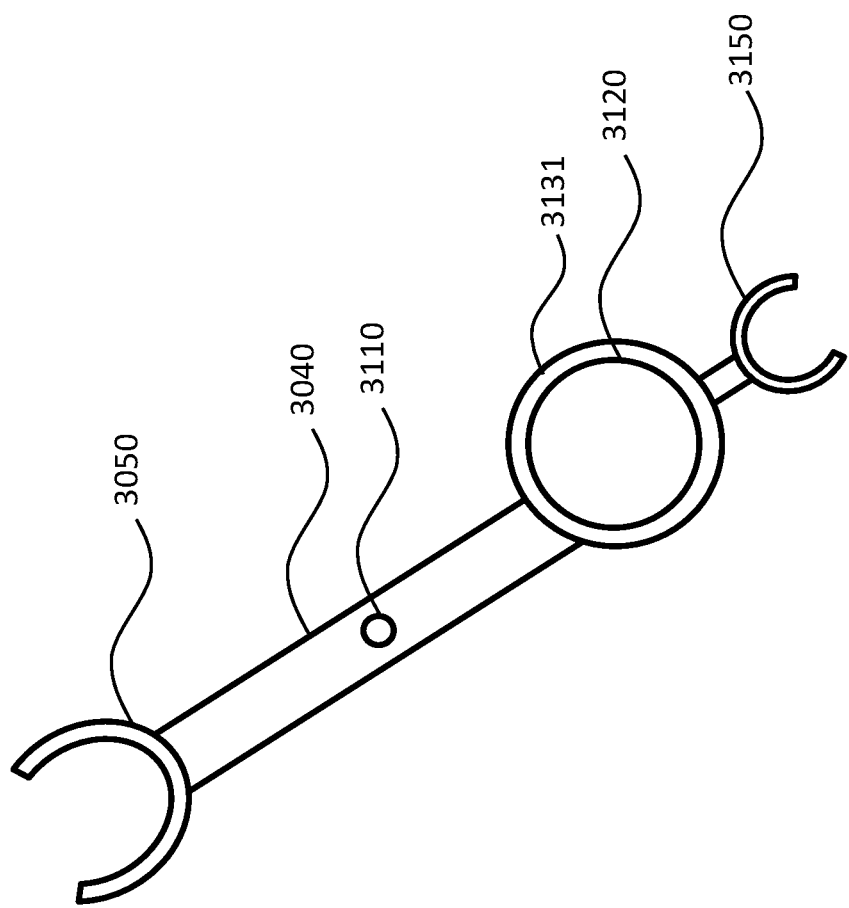

Note also that in an exemplary embodiment, there can be an apparatus that holds both tubes in place and/or also holds the cochlear implant electrode array and/or provides seals for the respective tubes. FIG. 30 depicts an exemplary embodiment of such an apparatus 3010. Apparatus 3010 can include the aforementioned disk and/or cylinder and or partial cylinder as noted above, and can also include arm 3040 which extends therefrom to clip 3050 which is configured to hold the other tube in place. In this embodiment, the interference fit established by the disk/cylinder is utilized to hold the apparatus 3010 in place. In an alternate embodiment, a bone screw or the like is utilized with respect to arm 3040. Moreover, in an exemplary embodiment, there can be a component that is configured to simply hold the tubes and or the electrode array in place, where the sealing features of the respective tubes and/or the associated components therewith and/or the sealing features of the electrode array and/or the associated components therewith are utilized to seal the cochlea. FIG. 31 depicts such an exemplary embodiment. Here, clip 3050 is connected to an arm 3040 which is configured to be connected to the outer wall of the cochlea via bone screw 3110. Arm 3040 is also connected to boss 3131 through which hole 3120 is located, through which a tube of the delivery system extends. In this exemplary embodiment, the boss 3131 interference fits with the tube to hold the tube relative to the fixation component. Also as can be seen, a clip 3150 attached to an arm that extends from boss 3131 is also present, which clip can be utilized to hold the cochlear implant electrode array in place. In some embodiments, one or more of these features may not necessarily be present, and in other embodiments, some of the features are substituted for some of the other features (e.g., clips are utilized to hold all components, etc.).

Figure 32:
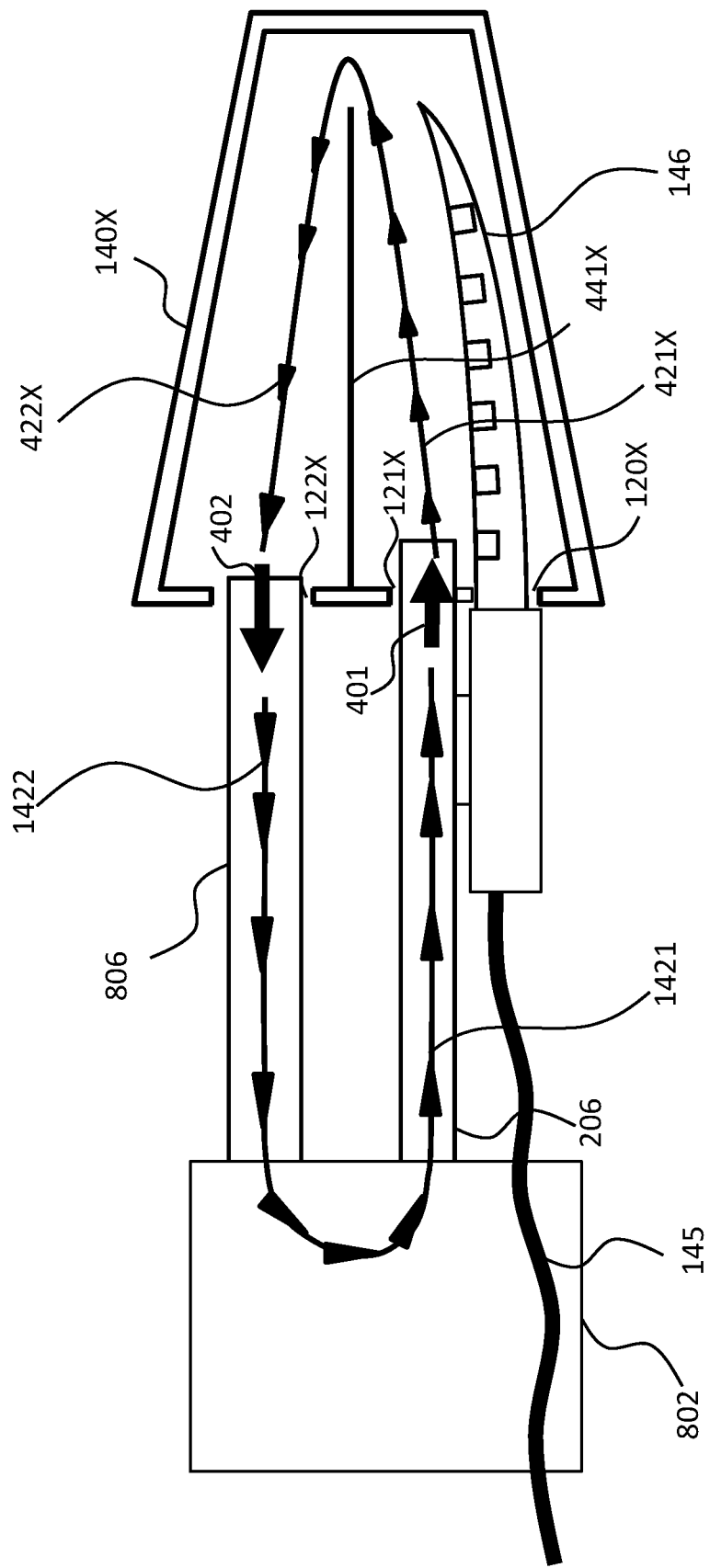
FIGS. 32-36 variously depict other exemplary embodiments.

While the embodiments detailed above have focused upon the delivery system being a separate component/separate system from the hearing prostheses system, in an exemplary embodiment, the two systems are instead subsystems of a system that includes both. In this regard, FIG. 32 depicts the cochlear implant electrode array extra-cochlear portion physically attached to the tube 206. In an exemplary embodiment, both subsystems are implanted at the same time.

Figure 33:
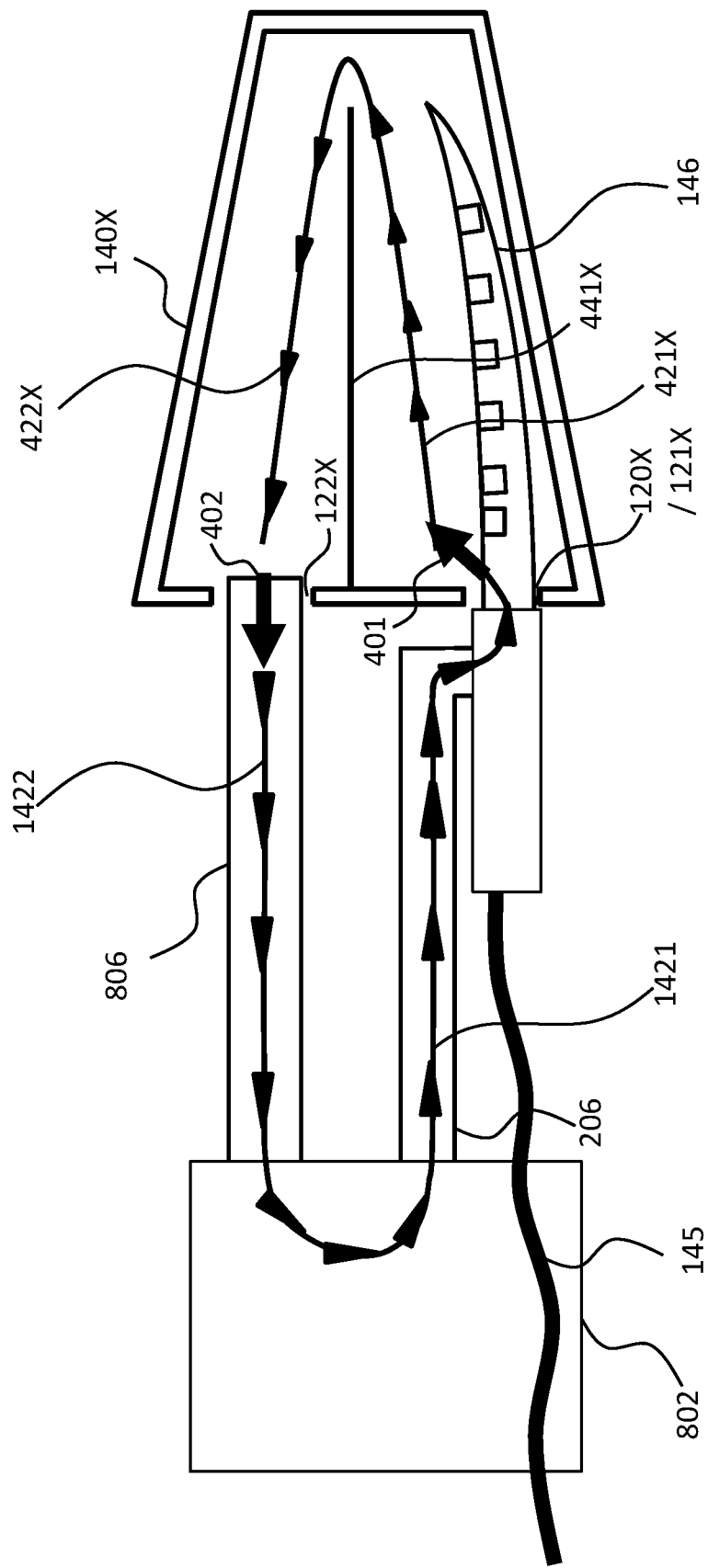

Note also that while the embodiments detailed above have focused on separate ports into the cochlea to access the cochlea for the respective tubes and the cochlear implant electrode array, an alternate embodiment, the cochlear implant electrode array and the delivery system are combined in a manner that enables access into the cochlea through a single port. FIG. 33 depict such an exemplary embodiment, where tube 206 is in fluid communication with a conduit within the electrode array 146 (not shown) that extends into the cochlea with the electrode array 146, which electrode array 146 includes an orifice on a side of the electrode array so as to enable fluid communication between the tube 206 and the tympanic duct.

In view of the above, it is to be understood that in at least some exemplary embodiments, there is a method, which includes driving an effective amount of a therapeutic substance to an apical region of the cochlea. In an exemplary embodiment of this method action, by way of example only and not by way of limitation, such can be executed utilizing system 800 as detailed above, where the circulation of fluid containing the therapeutic substance into the tympanic duct or into the vestibular duct, to the apical region, and then into the other of vestbular duct or the tympanic duct, can result in an effective amount of the therapeutic substance being driven thereto. This as opposed to a scenario where, for example, the therapeutic substance is provided into one of the ducts via system 200, for example, where the therapeutic substance may pool or otherwise remain at the basil portion of the given duct, or, in some alternative scenarios, where natural or even man-made fluid flow resulting from the introduction of the therapeutic substance into the cochlea may drive or otherwise bring a modicum of the therapeutic substance to the apical region, but such will not be an effective amount.

In an exemplary embodiment, the action of driving the effective amount of the therapeutic substance to the apical region is executed in a number of times. By way of example and only and not by way of limitation, such is executed with each circulation, where the circulation can occur H times, where H can be one, two, three, four, five, six, seven, eight, nine, 10, 11, 12, 13, 14, 15, 16, 17, 18, 19, 20, 21, 22, 23, 24, 25, 26, 27, 20, 29, 30, 35, 40, 45, 50, 55, 60, 65, 70, 75, 80, 85, 90, 95, 100, 110, 120, 130, 140, 150, 160, 170, 180, 190, or 200, or 225, or 250, or 275, 300, 350, 400, 450 or 500 or more times or any value is a range of values therebetween in 1 increment. It is noted that in an exemplary embodiment, the aforementioned number of circulations can be based on a single dose. That is, in an exemplary embodiment, by way of example only and not by way of limitation, the reservoir and mixing system can "inject" or otherwise entrain a dose of a therapeutic substance into the fluid flow, and then the fluid is circulated H number of times, and then another dose is injected or otherwise entrained into the fluid flow. This can be repeated H number of times in some embodiments.

Note also that in some exemplary embodiments, the therapeutic substance can ultimately become diffused evenly or otherwise substantially evenly in the fluid flow, or otherwise can be diffused such that all parts are substantially all parts of the fluid flow contain an amount of therapeutic substance that will be effective in treating the tissue. In an exemplary embodiment, the circulation can occur for a given period of time until the therapeutic substance is effectively distributed in the fluid flow, at which point the circulation can be halted. In an exemplary embodiment, such can be based on empirical and/or statistical data. In this regard, in an exemplary embodiment, a sensor can be provided that can sense the presence and/or determine the amount of therapeutic substance in the fluid flow. Moreover, in an exemplary embodiment, the amount of time it takes for the fluid to completely circulate through the system and through the cochlea can be known, based on, statistical and/or empirical data (e.g., markers can be projected or otherwise entrained into the flow), and the amount of therapeutic substance can be metered so as to evenly distribute or otherwise effectively evenly distribute the amount of therapeutic substance into the flow. Upon a determination that the therapeutic substance is evenly distributed or otherwise effectively distributed within the cochlea, the circulation is shut down.

It is also noted that the aforementioned circulation(s) can occur within a given temporal period. Accordingly, in an exemplary embodiment, there is a method that entails circulating fluid through the cochlea H number of times within 1, 2, 3, 4, 5, 6, 7, 8, 9, 10, 11, 12, 13, 14, 15, 16, 17, 18, 19, 20, 21, 22, 23, 24, 25, 26, 27, 20, 29, 30, 35, 40, 45, 50, 55, 60, 65, 70, 75, 80, 85, 90, 95, 100, 110, 120, 130, 140, 150, 160, 170, 180, 190, 200, 225, 250, or 275, 300, 350, 400, 450, or 500 seconds or minutes or hours, depending on the utility and the enablement and the efficacy of doing such.

Corollary to the above, it can be understood that in an exemplary embodiment, there is a method that includes the method actions of tapping a cochlea at a first location, which first location can be at the round window, at the oval window, or at a cochleostomy at the basil portion of the cochlea, or a cochleostomy at a location away from the basil portion of the cochlea, such as any of the locations detailed herein or other locations that can have utilitarian value. The method further includes the action of tapping the cochlea at a second location away from the first location, which can include, for example, tapping the cochlea at the other of the round or oval window, or at a cochleostomy according to any of the teachings detailed herein or other locations that can have utilitarian value. It is noted that the first location and the second location can be a location that both leads to the tympanic duct or the vestibular duct. The method further includes inserting a component of a prostheses, such as electrode array of a cochlear implant or a mechanical stimulator of a DACS, etc., into the cochlea at the first tapped location. The method also includes the action of at least one of inputting drug or another type of therapeutic substance into the cochlea or removing drug or the another type of therapeutic substance out of the cochlea using fluid flow through the second tapped location. In an exemplary embodiment of the aforementioned method, the tapped location where the drug or other therapeutic substance is inputted and/or removed can be a location away from a basal end of the cochlea, such as, for example, at the second turn, the 1.5 turn, or in any of the angular locations detailed herein or other locations that can have utilitarian value.

As will be understood as detailed herein, in an exemplary embodiment, the tapped location where the drug or other therapeutic substance inputted is a location away from a basal end of the cochlea. It is also to be understood that in some exemplary embodiments, a third tapping can be executed at a third location away from the first and second locations. This third tapping can be for the return of the fluid circulated out of the cochlea. That said, as detailed above, such as where a single tap is utilized for both the hearing prosthesis and the delivery and/or return of fluid, in an exemplary embodiment, there are only two locations that are tapped. (To be clear, the embodiment of FIG. 33, for example, which depicts the electrode array as being utilized to deliver the fluid into the cochlea, can be used, in an alternate embodiment as the return of fluid from the cochlea (or both, with respect to the embodiments where the fluid flow can be reversed)).

While the embodiments detailed above have typically focused on circulating perilymph or another fluid into and out of the cochlea, in at least some alternative embodiments, the utilitarian value associated with fluid circulation is executed without the fluid leaving the cochlea. That said, in at least some exemplary embodiments, while embodiments detailed above with respect to circulating a fluid flow into and out of the cochlea of focused on circulating the fluid from the tympanic duct and then out of the cochlea and then to the vestibular duct or vice versa, in some embodiments, fluid is flown out of the tympanic duct into the middle ear, and then flown back into the tympanic duct and then into the vestibular duct and then into the middle ear and/or then back into the vestibular duct and then into the tympanic duct and then into the middle ear and then back into the tympanic duct and so on, and this can be repeated a number of times.

In an exemplary embodiment, there is a therapeutic substance delivery system configured to artificially flow perilymph within the cochlea from the scala tympani to the scala vestibuli and then back from the scala vestibuli to the scala tympani and/or vice versa, so as to distribute the therapeutic substance within the cochlea. In an exemplary embodiment of this exemplary embodiment, the fluid exits the cochlea and then reenters the cochlea, while in other embodiments, the fluid never leaves the cochlea, at least with respect to a given circulation regime.

In at least some exemplary embodiments, the delivery system is configured to establish a circulation via the use of an implanted impeller or the like that is implanted into the cochlea that circulates the fluid, and thus the therapeutic substance, as just detailed. Also, in an exemplary embodiment, the impeller can be located in the middle ear, where, for example, fluid is removed from the cochlea from one of the vestibular duct or the tympanic duct, mixed with a therapeutic substance in the middle ear, and then reinserted into the cochlea at that same duct from which it was removed, where the system is configured to flow the fluid and thus the entrained therapeutic substance from the one duct to the other, or at least to the apical portion of the cochlea. In some embodiments, the delivery system is configured to flow the fluid from the other duct back to the original duct of entrance, and so on, and this can be repeated a number of times so as to distribute the therapeutic substance.

Moreover, in at least some exemplary embodiments, there is a method that includes a method action of establishing perilymph flow at least one of into or out of the cochlea and establishing perilymph flow the other of into or out of the cochlea at another location from the aforementioned first and second locations, thereby driving the effective amount of the therapeutic substance to the apical location. Also, in an exemplary method, there is a method action of establishing perilymph flow at least one of into or out of the cochlea at a first location and establishing perilymph flow the other of into or out of the cochlea at a second location away from the first location, thereby driving the effective amount of the therapeutic substance to the apical location. The first and second locations can be the same as the first and second locations detailed above or can be different. Also, in some embodiments of the methods herein, the method(s) are such that the established flow is established via an extra cochlea fluidic pump system that extends from the first location into the middle ear of the recipient back to the cochlea to the second location, wherein the pump system is located in the recipient for at least or for U hours, where U is 1, 2, 3, 4, 5, 6, 7, 8, 9, 10, 11, 12, 13, 14, 15, 16, 17, 18, 19, 20, 21, 22, 23, 24, 25, 26, 27, 20, 29, 30, 35, 40, 45, 50, 55, 60, 65, 70, 75, 80, 85, 90, 95, 100, 110, 120, 130, 140, 150, 160, 170, 180, 190, 200, 225, 250, or 275, 300, 350, 400, 450, 500, 550, 600, 650, 700, 800, 900, 1000, 1110, 1200, 1300, 1400, 1500, 1600, 1700, 1800, 1900, 2000, 2250, 2500, 2750, 3000, 3500, 4000, 4500, 5000, 6000, 7000, 8000, 9000, 10000, 15000, or 20000 or any value or range of values therebetween in 1 increment.

Moreover, in at least some exemplary embodiments of the methods detailed herein, the methods include the method action of artificially flowing perilymph within the cochlea from the scala tympani to the scala vestibuli and/or vice versa for at least or for U minutes in total, thereby driving the therapeutic substance to the apical location. In some embodiments, the aforementioned established flow is an artificial perilymph circulation from the scala tympani to the vestibuli, out of the cochlea and then back into the cochlea and/or visa-versa. In some embodiments, this circulation occurs for at least or for U hours in total.

In view of the above, it is to be understood that in at least some exemplary embodiments, there are methods of and devices for artificially distributing a therapeutic substance within the cochlea beyond that which results from diffusion distribution. In this regard, system 200 operates on the principle of diffusion distribution. In system 200, a therapeutic substance is delivered into the cochlea, and then permitted to diffuse within the perilymph, so as to treat tissue within the cochlea. In an exemplary embodiment, the diffusion is analogous to a die marker released by a swimmer the like in the ocean: it is the die that flows within the ocean water. Moreover, in some embodiments where the perilymph does not flow from one duct into the other duct, osmosis or the like through the structure of the cochlea, such as through the Reissner's membrane, are relied upon to treat other portions of the cochlea, such as tissue within a duct that the fluid flow does not directly flow therein. In contrast to this, by driving the fluid from one duct to the other and/or by driving the fluid from one end of the duct, such as the basal end, to a more apical portion of the duct, the therapeutic substance is distributed beyond only diffusion distribution. To be clear, in at least some exemplary embodiments, diffusion is relied upon to distribute the therapeutic substance within the fluid, which will at least partially results in the distribution of the therapeutic substance within a limited portion of the cochlea. By driving the fluid and otherwise inducing the circulation of the perilymph into and out of the cochlea and/or within the cochlea, that diffused therapeutic substance which is diffused into the fluid is driven to other locations of the cochlea that would otherwise not be visited by the therapeutic substance/fluid-therapeutic substance mixture.

Accordingly, in an exemplary embodiment, there is a therapeutic substance delivery device that is configured to deliver drug to the cochlea at least in part via a post introduction non-diffusion based delivery.

As noted above, some embodiments utilize a mixer reservoir. As will be understood, in at least some exemplary scenarios of use, the reservoir might become depleted of the therapeutic substance contained therein or otherwise reach a level where further efficacious distribution of therapeutic substance to the cochlea will not be utilitarian feasible. To recharge or otherwise refill the reservoir (or other component(s) of the given delivery system), any of the teachings detailed above vis-à-vis system 200 can be utilized in at least some exemplary embodiments. That said, any other system of recharging or otherwise refilling the reservoir or other component(s) of the delivery system can utilize in at least some exemplary embodiments.

Figure 34:
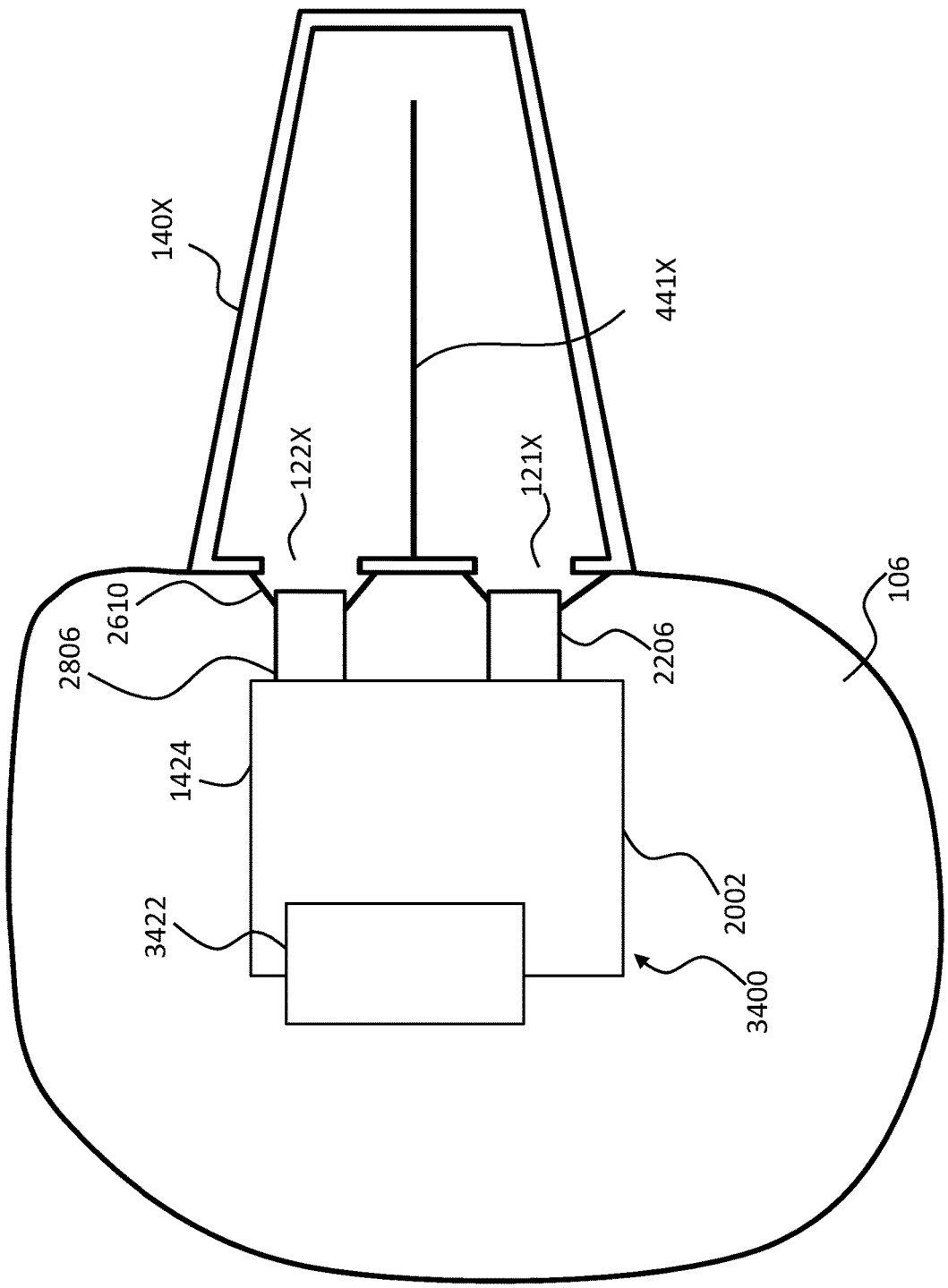

FIG. 34 represents an exemplary embodiment that has utilitarian value with respect to recharging or otherwise refilling the mixer reservoir. Here, delivery system 3400 includes a mixer reservoir 3422, which is exposed fluidically to the middle ear environment 106. In this regard, FIG. 34 conceptually depicts the inner boundaries of the middle ear. In an exemplary scenario, the reservoir 3422 is recharged or otherwise refill by placing the therapeutic substance adjacent the reservoir 3422 and permitting the therapeutic substance to enter the reservoir 3422 via some form of transfer mechanism, such as, for example, a controllably openable close the valve, a pump arrangement that sucks material from inside the middle ear cavity into the reservoir, and osmosis system or the like.

Figure 35:
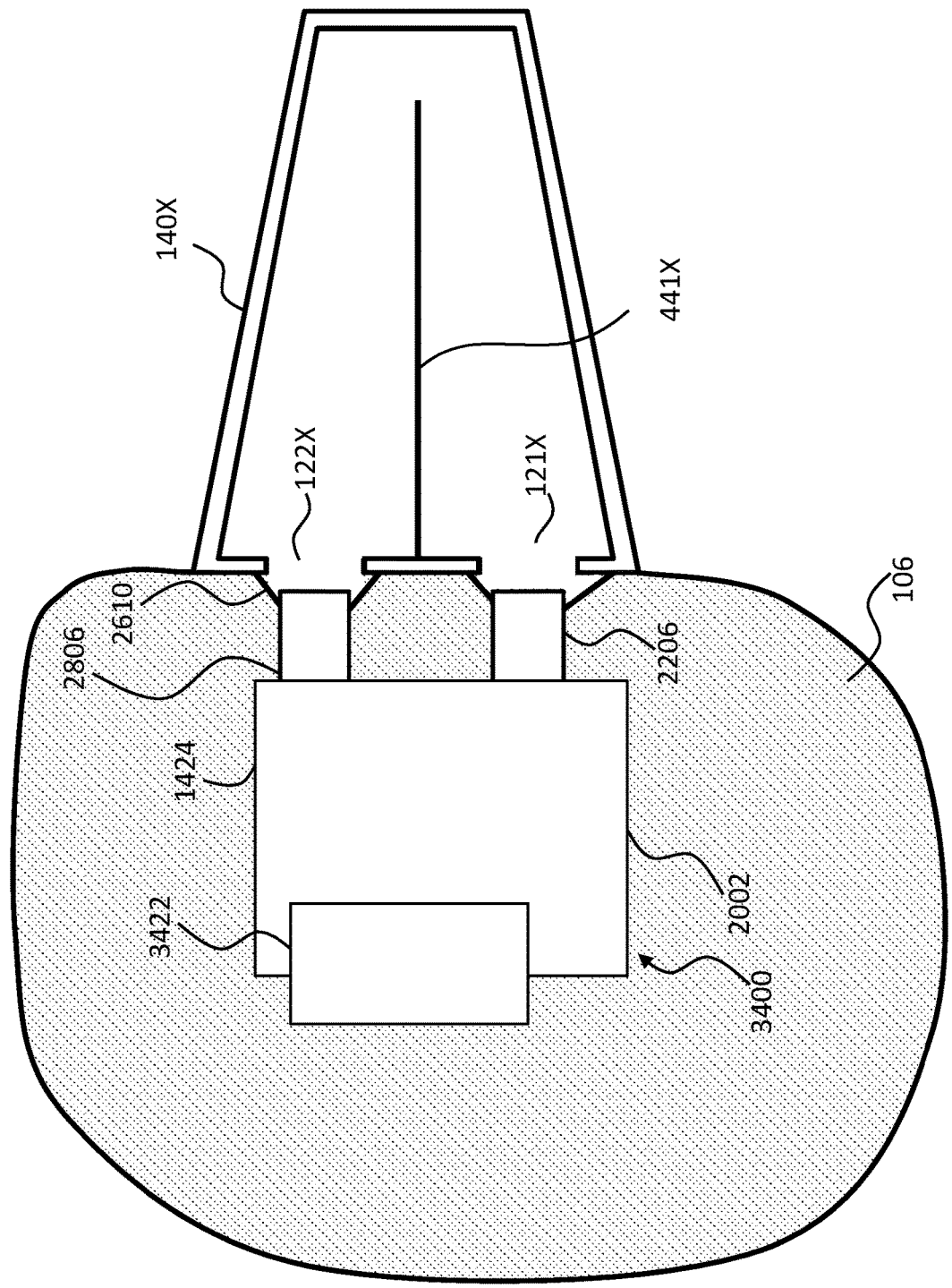
Figure 36:
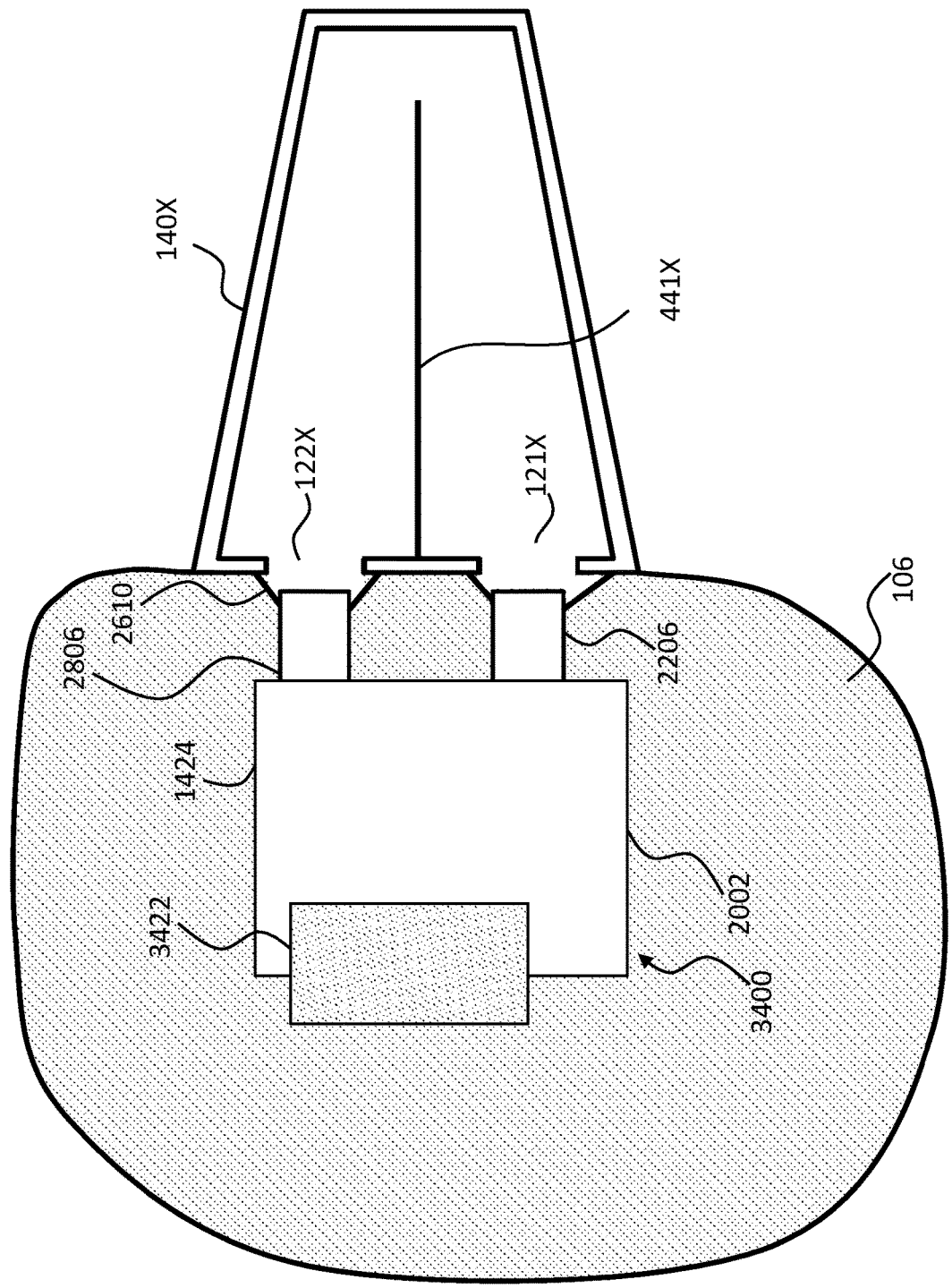

In an exemplary scenario, the therapeutic substance is delivered into the middle ear cavity, and the reservoir absorbs other rise up takes the therapeutic substance. FIG. 35 depicts an exemplary scenario where the middle ear cavity 106 is filled or substantially filled with a therapeutic substance, or, a carrier of the therapeutic substance, where the therapeutic substance is uptaken into the reservoir 3422. By way of example only and not by way of limitation, a gel or the like that supports or otherwise holds the therapeutic substance therewith can be inserted into the middle ear cavity so that the gel interfaces with the reservoir 3422. The reservoir 3422 or other component of the system 3400 uptakes the therapeutic substance (e.g., by utilization of an osmotic membrane that extracts the therapeutic substance from the gel, by electrolysis that extracts the therapeutic substance from the gel, etc.) and charges or otherwise refill the reservoir with the therapeutic substance. This is conceptually presented by way of example in FIG. 36.

Thus, in view of the above, it can be seen that in an exemplary embodiment, there is a method that can include the actions of attaching a therapeutic substance delivery device at a tapped location of the cochlea prior to inputting drug into the cochlea, subsequently depleting an amount of therapeutic substance of the delivery device, and then subsequently recharging the delivery device with more therapeutic substance via saturation of a local environment of the delivery device. In an exemplary embodiment, the saturation can be by a material that is purely the therapeutic substance, while in other embodiments, the saturation can be by a mixture of the therapeutic substance in some other carrier substance.

Figure 37:
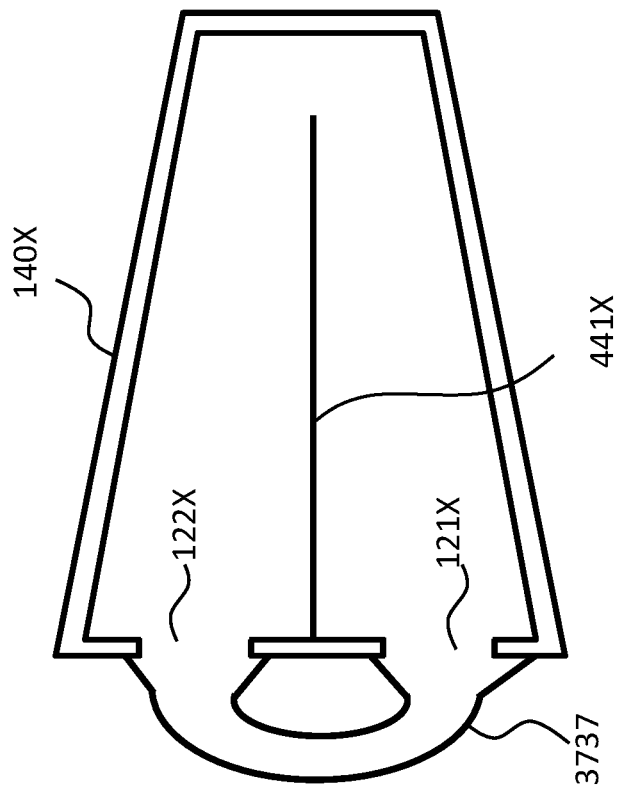
FIGS. 37-41B depict other exemplary embodiments.

FIG. 37 depicts another exemplary embodiment of a conduit system 3737 which places the tympanic duct and the vestibular duct into fluid communication with each other outside the cochlea. In an exemplary embodiment, owing to the dual paths for the two ducts to communicate with one another, natural circulation can occur into and out of the cochlea. In this regard, in an exemplary embodiment, the system is a passive system with respect to enabling circulation into and out of the cochlea. It is further noted that in an exemplary embodiment, the conduit system 3737 may not necessarily include or otherwise be directly associated with the therapeutic substance. In an exemplary scenario, a therapeutic substance is separately injected or otherwise inserted into the cochlea, and then subsequently, the conduit system 3737 is attached to the cochlea, and the natural circulation that occurs distributes the therapeutic substance within the cochlea. Still further, in an exemplary scenario, the conduit system 3737 is first attached to the cochlea, and then the therapeutic drug is inserted into the cochlea, or otherwise inserted into the now expanded volume of the perilymph containing fluid. In this regard, in an exemplary embodiment, the conduit system 3737 is made of a material that can be penetrated by a syringe or the like. In an exemplary scenario, a syringe is utilized to pierce or otherwise gain access to the interior of the conduit system 3737, whereby the syringe is utilized to inject the therapeutic substance into the conduit system 3737, where the circulation associated there with ultimately distribute therapeutic substance within the cochlea. That said, in an alternate embodiment, by way of example only and not by way of limitation, the conduit system 3737 can include a component that is specially configured to receive the syringe/needle of the syringe. By way of example only and not by way of limitation, an apparatus that is akin to the drug containing vials that have the pierceable container tops can be located at, for example, a base of the conduit system 3737.

Figure 38:
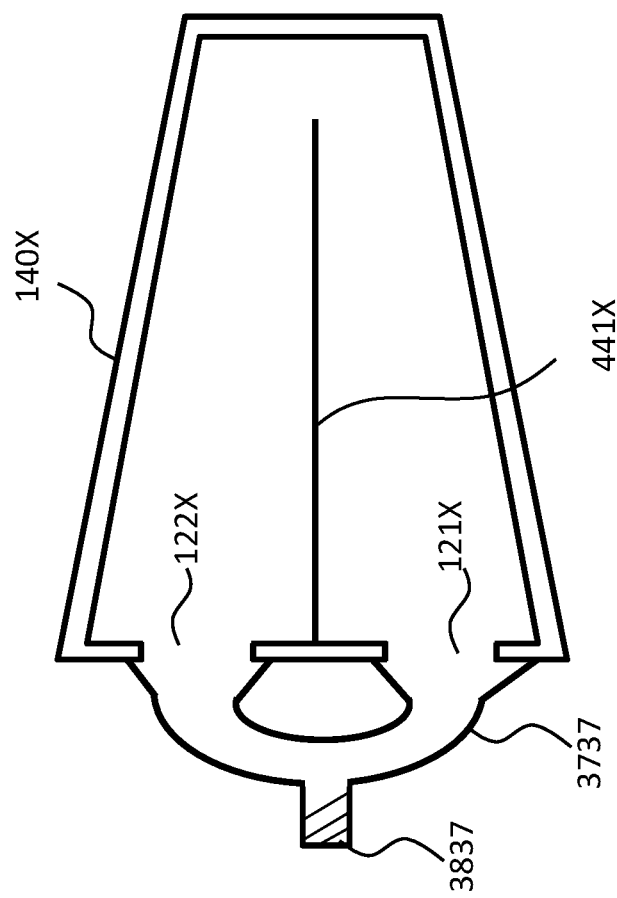

That said, in an alternate embodiment, the conduit system 3737 can have a tap or the like where the therapeutic containing substance can be attached so that the therapeutic substance can be inserted into the conduit system. In this regard, FIG. 38 presents an exemplary embodiment where tap 3837 is located at the geometric center of the conduit system 3737. Tap 3837 is threaded so as to receive mail threads of a syringe. In an exemplary embodiment, the syringe is screwed onto tap 3837, establishing a seal therebetween, and then the syringe is depressed to inject the therapeutic substance in the conduit 3737. In an exemplary embodiment, a male threaded cap (not shown) is subsequently screwed onto the tap 3837 to seal or otherwise closer the system. In an exemplary embodiment, on a determination that there is utilitarian value with respect to re-providing therapeutic substance, the aforementioned male threaded cap is unscrewed to obtain access to the interior of the conduit system 3737, and then a syringe is then subsequently screwed onto the mail threads of the tap 3837, and then the therapeutic substances then injected therethrough, and then the cap is replaced. Still, it is noted that in some alternate embodiments, element 3837 can instead be a membrane or the like that is pierceable by a needle and then subsequently closed in a hermetic or semi hermetic fashion or at least in a manner that resists leakage of the fluid therethrough.

While the embodiments detailed above relies on threads to secure the cap to the conduit system, in an alternate embodiment, a press fit or an interference fit or the like can be utilized to secure the cap to the conduit system and/or to secure the syringe to the conduit system. Any arrangement that can enable the transfer of therapeutic substance from the syringe to the conduit system and/or any arrangement that can seal the conduit system can utilize in at least some exemplary embodiments.

Figure 39:
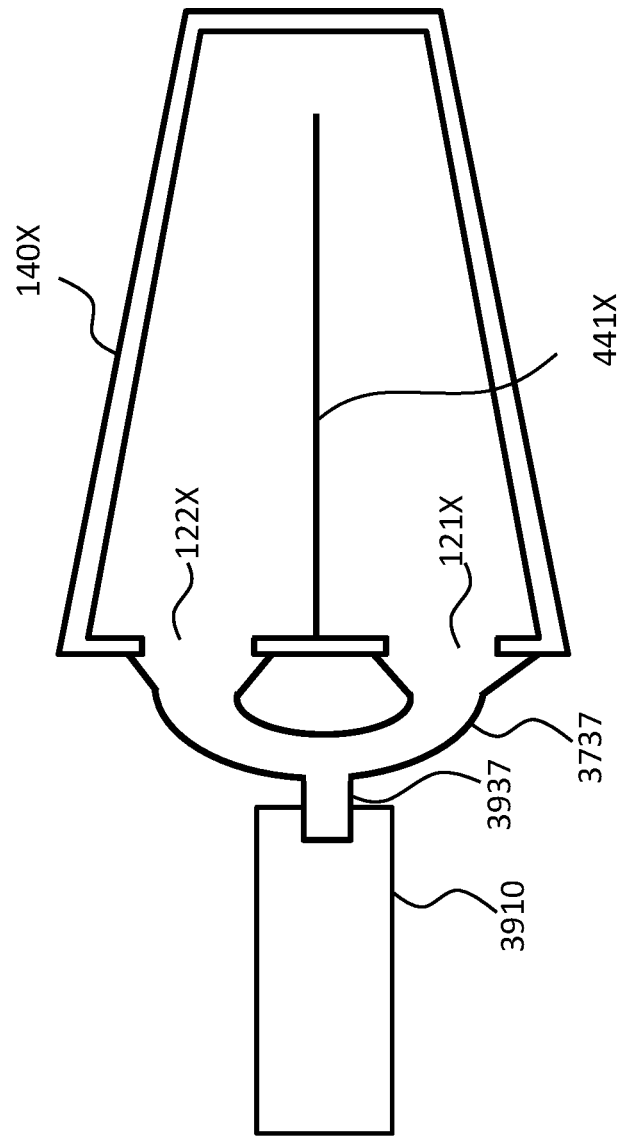
Figure 40:
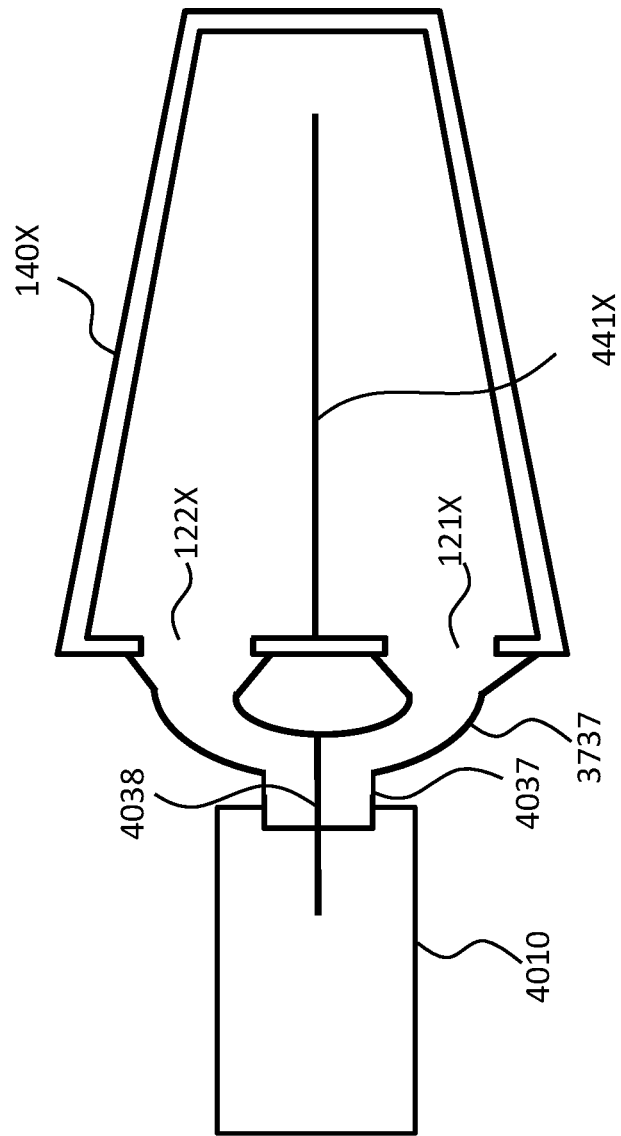

FIG. 39 depicts an exemplary embodiment where the reservoir is removably replaceable from the conduit system 3737. Here, tap 3937 is configured to interface with reservoir 3910. In an exemplary embodiment, reservoir 3910 is configured to be removably replaceable from 3937. In this embodiment, reservoir 3910 is configured to establish a seal around the outer circumference of 3937. In this embodiment, the therapeutic substance contained in reservoir 3910 is configured to defuse into the stream of fluid flowing through conduit system 3737 and passed the tap 3937. That said, FIG. 40 depicts an exemplary embodiment where the tap 4037 is configured with a barrier wall 4038 that directs the fluid flow into the reservoir 4010, and thus more affirmatively commingling the perilymph with the bioactive substance contained in the reservoir 4010. In an exemplary embodiment, the cap (not shown) is configured to accommodate the barrier 4038 such that there is a space between the end of the barrier 4038 and the cap so that fluid can travel there around. That said, in some embodiments, reservoir 4010 is a semi-permanent part of the system, and is removed and replaced when the therapeutic substance therein is been depleted.

In at least some exemplary embodiments, a replaceable bolus of therapeutic substance is utilized to charge the delivery system.

Conversely, in another embodiment, the barrier 4038 is part of the reservoir 4010, and is removed when the reservoir is removed.

Figure 41A:
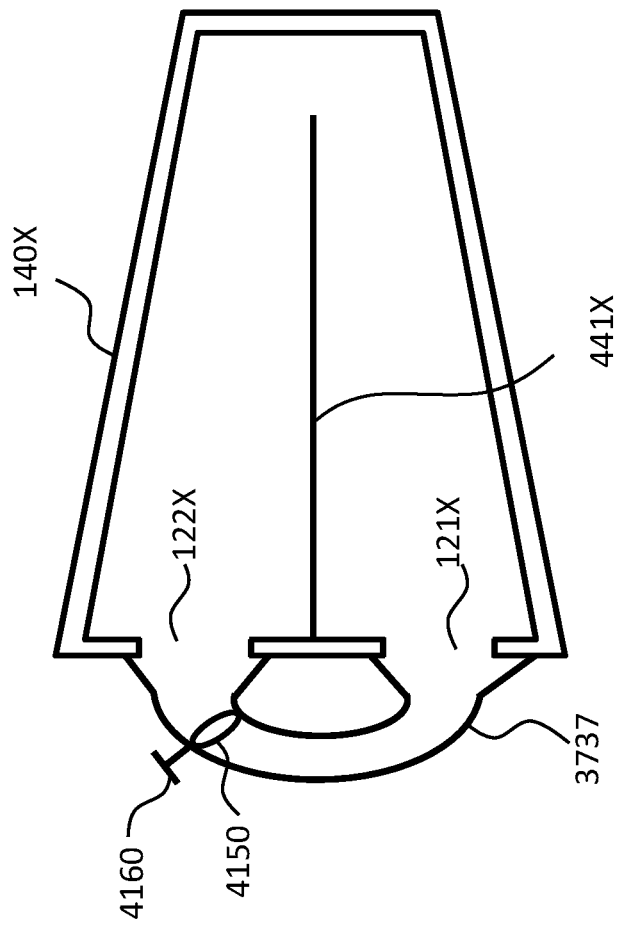

FIG. 41A depicts an exemplary embodiment that includes about 4150 that permits the controllably opening and closing of a fluid path from the scala tympani to the scala vestibuli and/or vice versa. In this exemplary embodiment, a knob 4160 is present that enables a surgeon or other healthcare professional to open and close the valve 4150. That said, in an alternate embodiment, a clamp or the like can be utilized to collapse the conduit 3737 and into on collapse the conduit 3737, thereby respectively preventing fluid flow and enabling fluid flow. Any device, system, and/or method of controllably opening and closing the fluid path from the respective ducts can be utilized at least some exemplary embodiments.

Figure 41B:
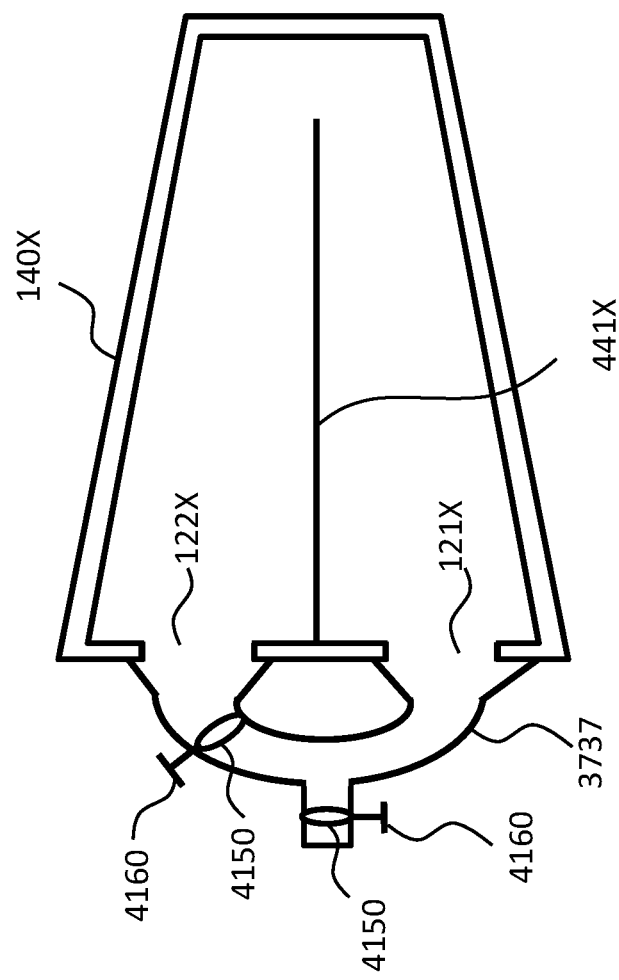

FIG. 41B depicts another exemplary embodiment parallel to the embodiment of FIG. 41A but includes a second valve at the reservoir port, as can be seen. Thus, in an exemplary embodiment, there is a means for distributing a therapeutic substance that includes a passageway extending from the scala vestibuli to the scala tympani that includes one or more valves to at least one of controllably open and close a fluid path from the scala tympani to the scala vestibuli and/or vice versa or permit a reservoir containing the therapeutic substance to be placed into and out of fluid communication with the passageway thereby enabling removal of a reservoir from the passageway while maintaining a closed fluidic system of the device.

In an exemplary embodiment, there is a system that includes one or more valves that open for delivery of drug, close for the replacement of drug loading, and then open again for subsequent delivery. It is noted that in some embodiments, the valves are part of the device that couples the ducts together, while in other embodiments, the valves are part of the reservoir/removable/replaceable device that contains the therapeutic substance.

Figure 42:
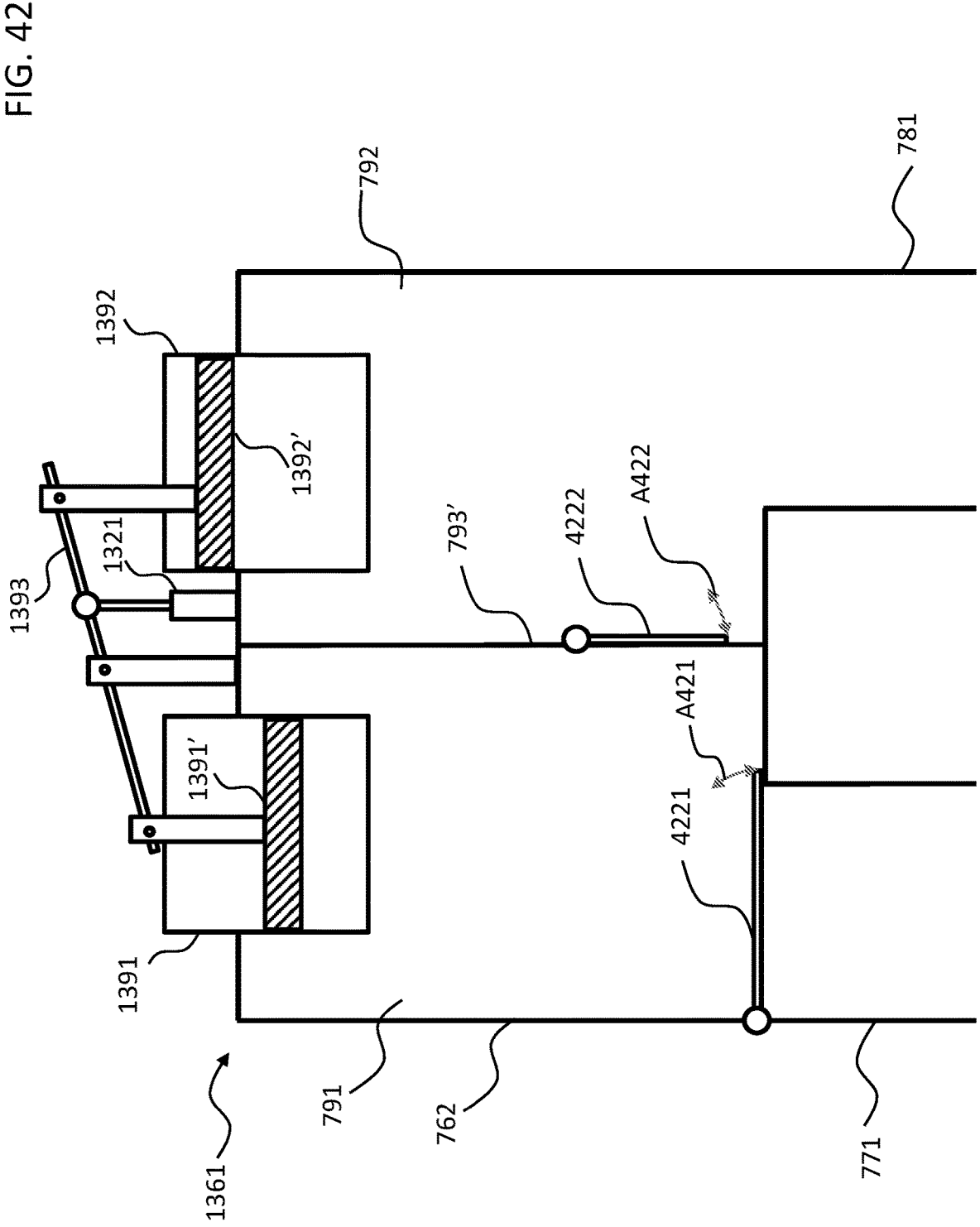
FIG. 42 depicts an exemplary pump that can utilitarian value with respect to some embodiments.

FIG. 42 depicts another embodiment of a device configured to circulate fluid. FIG. 42 depicts an actuator assembly 1361. Here, there is tube 771 that interfaces with one side of the cochlea and is in fluid communication with one of the ducts, which leads to chamber 791, which is separated from chamber 792 by barrier 793'. The actuator includes displacement cylinders 1391 and 1392. The cylinders include pistons 1391' and 1392' that move in an alternating manner in and out (or, more precisely, towards and away) from chambers 791 and 792 respectively, thus varying the total volume of those chambers. As can be seen, a lever arrangement 1393 is utilized, where a single actuator 1321 drives the movement of the pistons 1391' and 1392' in an equal but opposite manner. That said, in an alternate embodiment, two separate actuators can be utilized to independently drive the two pistons in an alternating manner. In this regard, a control circuit such as a programs computer chip that controls the actuation of the actuators can be utilized to control the actuation of the separate actuators so as to achieve the dual actuation. Note further, that while the embodiment depicted in FIG. 42 utilizes two separate pistons, in an alternate embodiment, a single piston can be utilized, where the piston is manifolded to the two chambers 791 and 792 such that movement of the piston in one direction displaces fluid into a given chamber while displacing fluid from the other chamber and vice versa. Any arrangement that can enable the fluidic teachings detailed herein and/or variations thereof to be practiced can be utilized in at least some embodiments. Also, as will be detailed below, embodiments also include non-fluidic embodiments, and thus any arrangement that can enable the principles of operations detailed herein and/or variations thereof to be practiced can be utilized in at least some exemplary embodiments.

In the embodiment of FIG. 42, the diameter of the piston is approximately the same as the diameters of the tubes 771 and 781, and thus there is no hydraulic amplification. That said, in alternative embodiments, the diameters can be larger or smaller to achieve hydraulic amplification and/or hydraulic deamplification.

Thus, in an exemplary embodiment, the actuator assembly is configured to respectively displace the fluids in the chambers 791 and 792 by controllably moving the pistons 1391' and 1392', thereby generating positive and negative pressure differentials within the chambers. As can be seen, flap valve 4221 is located at the end of tube 771, and is configured to move in the direction of arrow A421. Also, flap valve 4222 is located at the passageway between chamber 791 and 792 and is configured to move in the direction of arrow A422. With the device of FIG. 42, the fluid can be circulated into and out of the cochlea. Not shown is a fluidic coupling with a reservoir of drug or the like that can be utilized to inject drug into one of or both of the chambers (or in some embodiments, the pistons are utilized to suck the drug into the chambers).

In view of the above, it can be seen that in some embodiments, there is a device, such as a perilymph fluid shunt, etc., which can have couplings to locations of perilymph or endolymph which can allow or otherwise enable or assist flow between the two locations. In some embodiments, the perilymph can then be mixed with an active substance, which can be liquid, solid, encapsulated cells etc. In some embodiments, the flow between the two locations is driven as a result of an active device or the like or otherwise by a pump or the like. That said, in other embodiments, a semi-natural circulation can result owing to the fact that there are two routes from the tympanic duct to the vestibular duct and vice versa. Any device that can enable the artificial connection of the ducts, such as a cannula, a fluid shunt, a tube apparatus, etc., can be utilized in at least some exemplary embodiments.

Note also that in some embodiments, the active therapeutic substance can be embedded in the shunt that connects the two ducts. In an exemplary embodiment, the active therapeutic substance can exude into the fluid flow. By way of example only and not by way of limitation, the shunt can include a porous interior surface in which the therapeutic substance can be located. In an exemplary embodiment, the shunt or other apparatus that connects the respective ducts houses the therapeutic substance in a particular discreet area thereof, such as at an entrance and/or an exit of the shunt/other apparatus.

Figure 45:
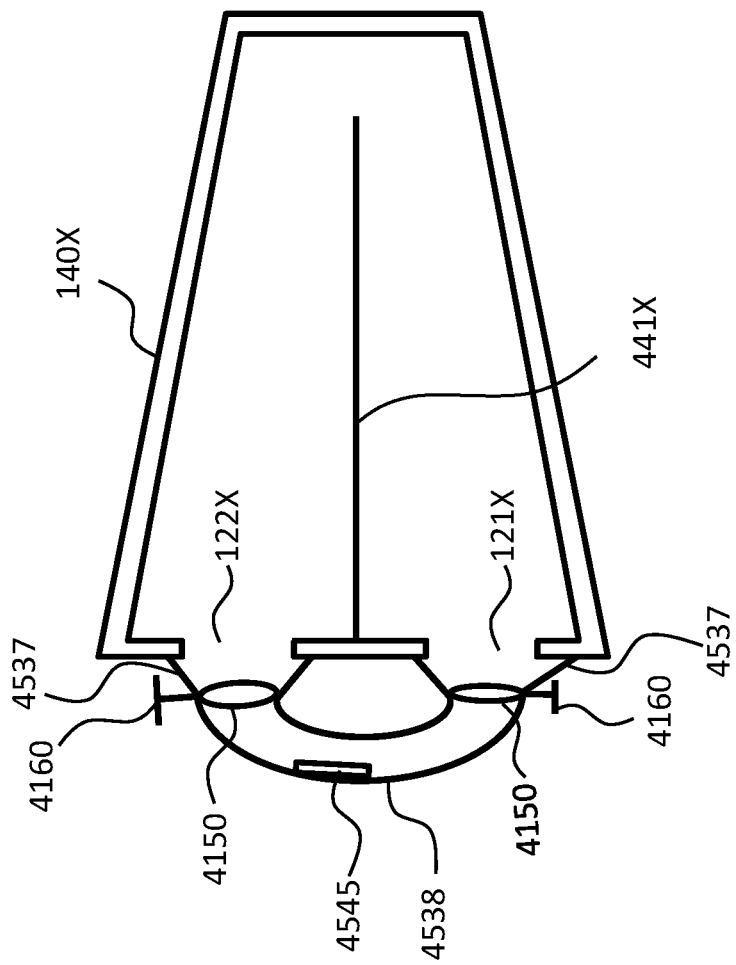

In an exemplary embodiment, the shunt or otherwise the delivery system is replaceable in its entirety or in part. By way of example only and not by way of limitation, with respect to a shunt system, where, for example, the drug is embedded into the shunt body, after a period of time, the shunt is removed, and replaced with a new shunt. In an exemplary embodiment, this can be done with respect to the artificial components in their entirety, or otherwise can be done with respect to only a subcomponent so as to not disturb the components that directly interface with the cochlea. In this regard, FIG. 45 depicts an exemplary embodiment where the components that mount directly to the cochlea, duct portions 4537, remain attached to the cochlea, and the removable subcomponent 4538 is removed along with drug containing body 4545 (if still present), and then replaced with another removable subcomponent 4538 that includes a new charge of the drug containing body. In an exemplary embodiment, valves 4150 are closed prior to removal of the removable subcomponent 4538. After a new subcomponent 4538 has been attached, the valves are opened again. This way, leakage of perilymph or otherwise flow of fluid in the cochlea can be prevented or otherwise limited while the replaceable component/removable component is replaced.

Still further, in an exemplary embodiment, the therapeutic substance can be a solid or a gel or the like that is connected to the interior surface of the shunt, where the solid or gel dissolves or otherwise is entrained into the fluid flow. The therapeutic substance containing perilymph is then redirected into a different part of the scala, whether that be at an apical location or a basal location. Of course, the perilymph can be extracted at an apical region, and redirected into the scale at a basal region. Note also, that apical regions can be utilized for both extraction and return. Thus, the shunt can contain the therapeutic substance.

In some embodiments, there is a shunt or other type of apparatus that connects the respective ducts, where the shunt or other type of apparatus is connected to a pump which can deliver drugs, biologics or fluids into the cochlea, either directly or into the shunt.

In some exemplary embodiments, the shunt or other type of apparatus can include otherwise contain a micropump, impeller, etc. to encourage fluid flow from one duct to the other and/or of the therapeutic substance into the shunt and/or into the cochlea.

In an exemplary embodiment, the shunt or other type of apparatus that connects the respective ducts is a pressure relief device, and thus there is a method of using a shunt or other type of apparatus to relieve intracochlear pressure. In an exemplary embodiment, the shunt is not utilized to deliver therapeutic substance, but instead is used solely and exclusively to relieve intracochlear pressure, and there are also apparatuses that are configured as such for sole use.

Figure 43:
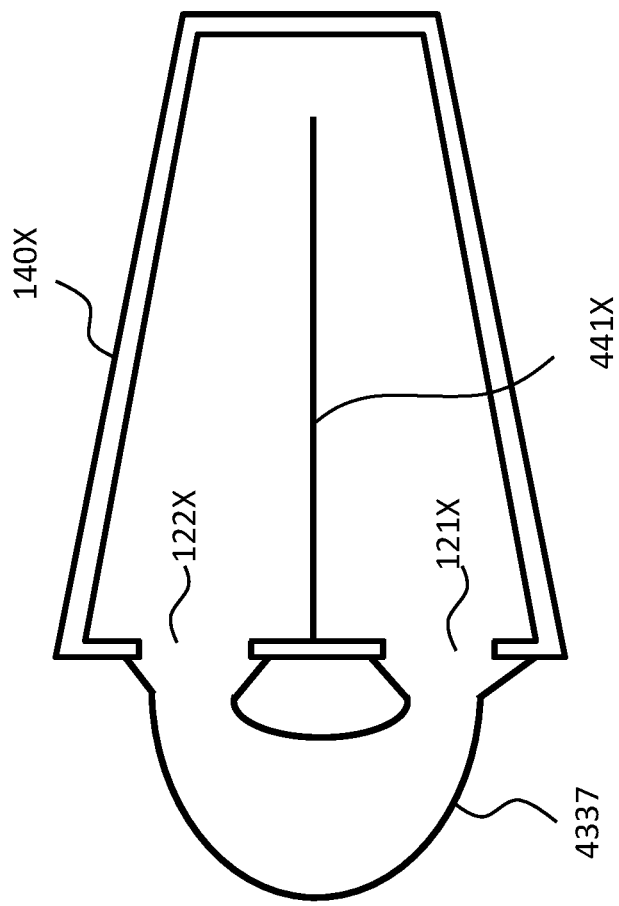
FIGS. 43-45 variously depict other exemplary embodiments.

FIG. 43 presents an exemplary embodiment of an exemplary apparatus that connects the ducts, apparatus 4337, that includes an expanded volume configured to relieve intracochlear pressure.

Figure 44:
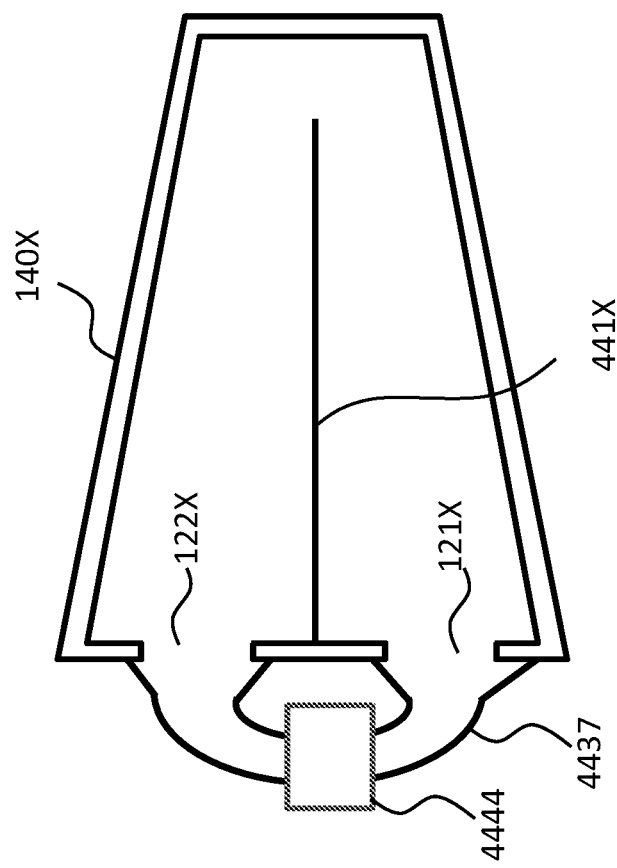

In an exemplary embodiment, the flow is achieved by a peristaltic manipulation of the passage between the ducts, as seen in FIG. 44. Particularly, apparatus 4437 includes a passageway that is surrounded by peristaltic pump 4444 that is configured to compress the passageway in a patterned manner or any other manner that will enable or otherwise induce fluid flow therethrough. In an exemplary embodiment, the shunt or other apparatus that connects the ducts is a discreet component/assembly, and the device(s) used to induce the fluid flow, such as the pumps, etc., are also discreet components/assemblies. In an exemplary embodiment, the pump is clamped around a shunt and manipulates the shunt to achieve flow.

While the embodiment of FIG. 44 presents an embodiment where the passageway is flexible and compressible, in some alternate embodiments, the passageway, such as the shunt, etc., is incompressible. In some embodiments, there is a device that places the ducts into fluid communication with one another, that is configured to vibrate the passageway between the two to achieve fluid movement. In an exemplary embodiment, element 4444 is instead a vibrator.

In an exemplary embodiment, flow in the shunt is achieved by a secondary fluid flow from an external pump (air/water/saline). As can be seen, the flow can be achieved by mechanical devices. In some other embodiments, electrical fields, magnetic fields, or heat transfer devices can be utilized. Any device, system, and/or method that can enable the inducement of fluid flow between the ducts can utilize in at least some exemplary embodiments.

It is noted that while at least some of the embodiments detailed above are presented in as having tubes/ducts, etc., that interface with the cochlea that have the same interior and exterior diameters respect to both ducts/locations. That said, in an alternate embodiments, the interfacing components can have different interior and exterior diameters. By way of example only and not by way of limitation, in an exemplary embodiment, a portion of the device that interfaces with the cochlea at the basal portion can have a larger diameter than the portion of the device that interfaces with the cochlea at the apical portion, or vice versa.

It is noted that in some exemplary embodiments, the access locations to the interior of the cochlear are created utilizing tools, such as drills the like. That said, in some alternate embodiments, the delivery system detailed herein and/or variations thereof can be configured such that they are self-accessing. By way of example only and not by way of limitation, in an exemplary embodiment, the delivery device can have a sharp portions at the end of the tubes that are configured to penetrate the round and oval windows, and can also include the aforementioned seals such that they sell seal when penetrating the round and oval windows. Still further, self-tapping components can be utilized on the components that interface with the cochlea. Note also, in an exemplary embodiment, there is a method where a partial cochleostomy is drilled into the cochlea, but it is not completely drilled into the cochlea, and the delivery device is utilized to "breakthrough" the remaining distance, thus preventing or otherwise limiting the amount of perilymph that escapes from the cochlea. Note also that in some exemplary embodiments, the tubes or otherwise tips of the delivery system can be configured to rotate and thus can be self-tapping.

While the embodiments detailed above have been described in terms of accessing perilymph containing bodies of the cochlea, in some alternate embodiments, the teachings detailed herein can be utilized to access the endolymph containing bodies of the cochlea, such as, for example, the cochlear duct. In an exemplary embodiment, the fluid is circulated into and out of the cochlear duct, and the delivery system can access the cochlea at the basil and/or the apical portions or other portions as detailed herein, except with respect to the cochlear duct instead of the other ducts.

It is noted that any reference herein to a therapeutic substance corresponds to a disclosure of an active substance such as an active drug or an active biologic etc., and any disclosure herein to an active substance such as an active drug or the phrase active substance in the generic manner corresponds to a disclosure of an active biologic or a therapeutic substance, etc. Any active pharmaceutical ingredient that can have utilitarian value can be a therapeutic substance. Proteins can be therapeutic substances as well. It is also noted that in an at least some exemplary embodiments, an inactive fluid can be a physiological saline, which can be utilized to convey the therapeutic substance into the cochlea.

in an exemplary embodiment, therapeutic substance include but are not limited to, any of those detailed above, and can include peptides, biologics, cells, drugs, neurotrophics, etc. Any substance that can have therapeutic features if introduced to the cochlea can be utilized in some embodiments.

It is noted that any disclosure of a device and/or system herein corresponds to a disclosure of a method of utilizing such device and/or system. It is further noted that any disclosure of a device and/or system herein corresponds to a disclosure of a method of manufacturing such device and/or system. It is further noted that any disclosure of a method action detailed herein corresponds to a disclosure of a device and/or system for executing that method action/a device and/or system having such functionality corresponding to the method action. It is also noted that any disclosure of a functionality of a device herein corresponds to a method including a method action corresponding to such functionality. Also, any disclosure of any manufacturing methods detailed herein corresponds to a disclosure of a device and/or system resulting from such manufacturing methods and/or a disclosure of a method of utilizing the resulting device and/or system.

Unless otherwise specified or otherwise not enabled by the art, any one or more teachings detailed herein with respect to one embodiment can be combined with one or more teachings of any other teaching detailed herein with respect to other embodiments, and this includes the duplication or repetition of any given teaching of one component with any like component.

While various embodiments of the present invention have been described above, it should be understood that they have been presented by way of example only, and not limitation. It will be apparent to persons skilled in the relevant art that various changes in form and detail can be made therein without departing from the scope of the invention.

What is claimed is:

1. An apparatus, comprising:
a drug delivery device configured to simultaneously interface with a scala tympani and a scala vestibuli of a cochlea of a recipient, wherein the drug delivery device includes a cochlea fluidic pump, wherein
the cochlea fluidic pump is configured to establish perilymph flow into and out of the cochlea, thereby driving an amount of a therapeutic substance deliverable by the drug delivery device to an apical region of the cochlea, and
the cochlea fluidic pump is configured to establish the perilymph flow after the cochlea fluidic pump has been located in a recipient for at least 168 hours.

2. The apparatus of claim 1, wherein:
the device is configured to induce complete circuit circulation from the scala tympani to the scala vestibuli and/or vice versa, thereby distributing the therapeutic substance within the cochlea.

3. The apparatus of claim 1, wherein:
the device includes a fluid inlet and a fluid outlet respectively configured to be placed into fluid communication with, respectively, the scala tympani and the scala vestibuli, and/or vice versa.

4. The apparatus of claim 3, further comprising:
a cochlear implant electrode array.

5. The apparatus of claim 3, wherein:
the drug delivery device contains a drug, the drug being the therapeutic substance; and
the drug delivery device is configured to deliver the drug to the cochlea.

6. The apparatus of claim 1, wherein:
the device is configured to establish, when simultaneously interfacing with the scala tympani and scala vestibuli, a complete fluid circuit made up of the scala tympani, the scala vestibuli, and the device.

7. The apparatus of claim 1, wherein;
the device is configured to permanently simultaneously interface with a scala tympani and a scala vestibuli of a cochlea so as to enable, respectively, ingress and egress and/or vice versa of perilymph from/to the cochlea during permanent interfacing.

8. The apparatus of claim 1, wherein:
the device is configured to extract perilymph from the cochlea, mix the therapeutic substance delivered by the drug delivery device with the extracted perilymph, and insert the mixture into the cochlea.

9. The apparatus of claim 1, wherein:
the device is configured to interface with at least one of the scala tympani or the scala vestibuli at a location at or above a second turn of the cochlea.

10. A device, comprising:
a prosthesis configured to distribute perilymph within a cochlea of a recipient, wherein the prosthesis includes a cochlea fluidic pump, wherein
the cochlea fluidic pump is configured to establish perilymph flow into and out of the cochlea, thereby driving an amount of a therapeutic substance deliverable by the prosthesis to an apical region of the cochlea, and
the cochlea fluidic pump is configured to establish the flow after the cochlea fluidic pump has been located in a recipient for at least 168 hours.

11. The device of claim 10, wherein:
the device is configured to be entirely located, collectively, in a middle ear and/or an inner ear of an adult human.

12. The device of claim 10, wherein:
the device is configured to be located, in part, in a middle ear and, in part, at a retroaurical position.

13. The device of claim 10, wherein:
the device is configured to extend from an outside of the cochlea to at least an interior of the cochlea and secure itself to the cochlea at a location proximate the location of extension to the at least an interior of the cochlea.

14. The device of claim 10, wherein:
the device is configured to move a non-perilymph substance from external to the cochlea to inside the cochlea via circulation, the non-perilymph substance corresponding to the therapeutic substance.

15. The device of claim 10, wherein:
the device is a therapeutic substance delivery device, and the device is configured to drive the therapeutic substance to a juncture of the scala tympani and the scala vestibuli.

16. The device of claim 10, wherein:
the device is configured to at least one of flow fluid into or out of the cochlea, and wherein the device includes a flow limiter to limit a volumetric flow rate to a safe level.

17. The device of claim 10, wherein:
the device is configured to at least one of flow fluid into or out of the cochlea, and wherein the device includes a flow controller to control volumetric flow rate to a utilitarian level.

18. The device of claim 10, wherein:
the device is configured to establish a fluid path from the scala vestibuli to the scala tympani of a human outside the cochlea in at least substantially the shortest path possible.

19. A device, comprising:
a means for interfacing with a cochlea; and
a means for distributing a therapeutic substance within the cochlea, wherein
the device includes a cochlea fluidic pump,
the cochlea fluidic pump is configured to establish perilymph flow into and out of the cochlea, thereby driving an amount of the therapeutic substance to an apical region of the cochlea, and
the cochlea fluidic pump is configured to establish the flow after the cochlea fluidic pump has been located in a recipient for at least 168 hours.

20. The device of claim 19, wherein:
the means for interfacing with the cochlea includes a means for establishing separate fluid communication between a scala tympani and an outside of the cochlea and a scala vestibuli and the outside of the cochlea.

21. The device of claim 19, wherein:
the means for distributing the therapeutic substance within the cochlea is also a means for distributing the therapeutic substance effectively equally within the cochlea.

22. The device of claim 19, wherein:
the device includes a shunt that establishes fluid communication from a scala tympani to a scala vestibuli of the cochlea.

23. The device of claim 19, wherein:
the device induces fluid flow from a scala tympani to a scala vestibuli, and/or vice versa, of the cochlea.

24. The device of claim 19, wherein:
the means for distributing the therapeutic substance within the cochlea is also a means for distributing the therapeutic substance so that an amount of therapeutic substance that reaches an area after a 120 degree turn of the cochlea with respect to a duct into which the therapeutic substance is delivered is 65% less than that which reaches tissue before the 120 degree turn of the cochlea.

25. A method, comprising:
driving an amount of a therapeutic substance to an apical region of the cochlea; and establishing perilymph flow into and out of the cochlea, thereby driving the amount of the therapeutic substance to the apical region, wherein
the established flow is established via a cochlea fluidic pump system that has been located in the recipient for at least 168 hours.

26. The method of claim 25, further comprising:
tapping a cochlea at a first location;
tapping the cochlea at a second location away from the first location;
inserting an electrode array into the cochlea at the first location;
at least one of inputting drug to the cochlea or removing drug out of the cochlea using fluid flow through the second location, the drug corresponding to the therapeutic substance.

27. The method of claim 26, wherein:
the tapped location where the drug is inputted and/or removed is a location away from a basil end of the cochlea.

28. The method of claim 26, further comprising:
prior to driving the amount of the therapeutic substance to the apical region of the cochlea, accessing the cochlea through skin of the human having the cochlea.

29. The method of claim 25,
wherein the amount that is driven is an effective amount.

30. The method of claim 25, wherein:
establishing perilymph flow into and out of the cochlea includes establishing perilymph flow into or out of the cochlea at a first location and establishing perilymph flow the other of into or out of the cochlea at a second location away from the first location, thereby driving the amount of the therapeutic substance to the apical region, wherein
the cochlea fluidic pump system is an extra cochlea fluidic pump system that extends from the first location into the middle ear of a recipient of the extra cochlea fluidic pump system back to the cochlea to the second location.

31. The method of claim 25, wherein establishing perilymph flow results in artificially flowing perilymph within the cochlea from a scala tympani to a scala vestibuli and/or vice versa so as to distribute the therapeutic substance within the cochlea beyond diffusion distribution.

32. The method of claim 31, wherein the amount that is driven is an effective amount.

33. The method of claim 25, wherein establishing perilymph flow results in artificially flowing perilymph within the cochlea from a scala tympani to a scala vestibuli and/or vice versa for at least 5 minutes in total, thereby driving the therapeutic substance to the apical region.

34. The method of claim 25, further comprising:
attaching a therapeutic substance delivery device at a tapped location of the cochlea prior to inputting drug into the cochlea, the therapeutic substance delivery device including the cochlea fluidic pump system, the drug corresponding to the therapeutic substance;
depleting an amount of therapeutic substance of the delivery device; and
recharging the delivery device with more therapeutic substance via saturation of a local environment of the delivery device.

35. The method of claim 25, wherein:
the established flow is an artificial perilymph circulation from the scala tympani to the vestibuli, out of the cochlea and then back into the cochlea and/or vice versa, and wherein the circulation occurs for at least 24 hours in total.

36. The method of claim 25, wherein establishing perilymph flow results in artificially flowing perilymph within the cochlea from the scala tympani to the scala vestibuli and then back from the scala vestibuli to the scala tympani and/or vice versa, so as to distribute the therapeutic substance within the cochlea beyond diffusion distribution.

37. The method of claim 25, wherein:
the action of driving the amount of the therapeutic substance to an apical region of the cochlea includes driving the therapeutic substance from a basial region of the cochlea to the apical region of the cochlea.

38. The method of claim 25, wherein the establishing of perilymph flow includes establishing perilymph flow into or out of the cochlea at a first location and establishing perilymph flow the other of into or out of the cochlea at a second location away from the first location, thereby driving the amount of the therapeutic substance to the apical region.

39. The method of claim 25, wherein:
the action of driving the amount of the therapeutic substance to an apical region of the cochlea is executed using a pump of the cochlea fluidic pump system in fluid communication with a basal region of the cochlea.

40. The method of claim 25, wherein:
the action of driving the amount of the therapeutic substance to an apical region of the cochlea is executed by a totally implantable medical device that includes the cochlea fluidic pump system.

41. The method of claim 25, wherein:
the action of driving the amount of the therapeutic substance to an apical region of the cochlea is executed totally within a human having the cochlea.

* * * * *